(12) United States Patent
Mori et al.

(10) Patent No.: US 7,193,033 B2
(45) Date of Patent: Mar. 20, 2007

(54) PEPTIDE HAVING APPETITE STIMULATING ACTIVITY

(75) Inventors: Masaaki Mori, Tsukuba (JP); Yukio Shimomura, Tsukuba (JP); Mioko Harada, Tsukuba (JP); Taiji Asami, Tsukuba (JP); Yoshio Matsumoto, Tsukuba (JP); Yuka Adachi, Tsukuba (JP); Tsukasa Sugo, Tsukuba (JP); Michiko Abe, Inashiki-gun (JP); Mika Goto, Nishinomiya (JP); Chieko Kitada, Sakai (JP); Takuya Watanabe, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 299 days.

(21) Appl. No.: 10/311,019

(22) PCT Filed: Jun. 20, 2001

(86) PCT No.: PCT/JP01/05257

§ 371 (c)(1),
(2), (4) Date: Dec. 11, 2003

(87) PCT Pub. No.: WO01/98494

PCT Pub. Date: Dec. 27, 2001

(65) Prior Publication Data

US 2005/0153391 A1    Jul. 14, 2005

(51) Int. Cl.
*C07K 14/435* (2006.01)
*A61K 38/17* (2006.01)
*C12P 21/02* (2006.01)

(52) U.S. Cl. .................... 530/300; 530/326; 514/2; 424/198.1; 536/23.5; 435/69.1

(58) Field of Classification Search ............ None
See application file for complete search history.

(56) References Cited

U.S. PATENT DOCUMENTS 5,350,836 A * 9/1994 Kopchick et al. .......... 530/399
5,591,602 A * 1/1997 O'Dowd .................. 435/69.1

FOREIGN PATENT DOCUMENTS

| JP | 09-121865 | 5/1997 |
| WO | WO 95/12670 | 5/1995 |
| WO | WO 00/22129 | 4/2000 |
| WO | WO 02/08417 A1 | 1/2002 |
| WO | WO 02/44368 | 6/2002 |
| WO | WO 02/093161 | 11/2002 |

OTHER PUBLICATIONS

Wells, J.A. (1990). Additivity of mutational effects in proteins. Biochemistry. 29(37):8509-8517.*
Ngo et al. (1994). Computational complexity, protein structure prediciton, and the Levinthal paradox. In Merz and Le Grand (Eds.) The Protein Folding Problem and Tertiary Structure Prediction. Birkhauser:Boston, pp. 492-495.*
Skolnick et al. (2000). From genes to protein structure and function: novel applications of computational approaches in the genomic era. Trends in Biotech. 18(1):34-39.*
Bork, A. (2000). Powers and pitfalls in sequence analysis: the 70% hurdle. Genome Res. 10:398-400.*
Doerks et al. (1998). Protein annotation: detective work for function prediction. Trends in Genetics. 14(6):248-250.*
Smith et al. (1997). The challenges of genome sequence annotation or The devil is in the details. Nature Biotech. 15:1222-1223.*
Brenner, S.E. (1999). Errors in genome function. Trends in Genetics. 15(4):132-133.*
Bork et al. (1996). Go hunting in sequence databases but watch out for the traps. Trends in Genetics. 12(10):425-427.*
O'Dowd et al. "The Cloning and Chromosomal Mapping of Two Novel Human Opioid-Somatostatin-like Receptor Genes, GPR7 and GPR8, Expressed in Discrete Areas of the Brain" Genomics 28:84-91 (1995).
Yukio Shimomura, et al., "Identification of Neuropeptide W as the Endogenous Ligand for Orphan G-protein-coupled Receptors GPR7 and GPR8", The Journal of Biological Chemistry, (2002), pp. 35826-35832, vol. 277, No. 39.
Database EMBL; EBI; Sep. 1998, "homosapiens chromosome 16, P1 clone 109-8C (LANL), complete sequence"; XP002309487; Database accession No. AC005606, Ricke et al.

* cited by examiner

*Primary Examiner*—Christine J. Saoud
*Assistant Examiner*—Jon M. Lockard
(74) *Attorney, Agent, or Firm*—David G. Conlin, Esq.; Jeffrey L. Kopacz, Esq.; Edwards Angell Palmer & Dodge, LLP.

(57) ABSTRACT

The present invention provides a ligand to GPR8, in particular polypeptides capable of binding to GPR8 or its amides or esters, or salts thereof, as well as DNA, encoding for such polypeptides. The ligand to GPR8 of the present invention is useful in developing a receptor-binding assay system with the use of a GPR8 expression system, for screening candidate compounds for drugs such as preventive/therapeutic agents for obesity, appetite stimulants, and prolactin production inhibitors.

9 Claims, 13 Drawing Sheets

Fig. 1

```
  1  atgcaggccgctgggcacccagagccccttgacagcaggggctccttctccctccccacg
     M  Q  A  A  G  H  P  E  P  L  D  S  R  G  S  F  S  L  P  T
 61  atgggtgccaacgtctctcaggacaatggcactggccacaatgccacttctccgagcca
     M  G  A  N  V  S  Q  D  N  G  T  G  H  N  A  T  F  S  E  P
121  ctgccgttcctctatgtgctcctgcccgccgtgtactccgggatctgtgctgtggggctg
     L  P  F  L  Y  V  L  L  P  A  V  Y  S  G  I  C  A  V  G  L
181  actggcaacacggccgtcatccttgtaatcctaagggcgcccaagatgaagacggtgacc
     T  G  N  T  A  V  I  L  V  I  L  R  A  P  K  M  K  T  V  T
241  aacgtgttcatcctgaacctggccgtcgccgacgggctcttcacgctggtactgcccgtc
     N  V  F  I  L  N  L  A  V  A  D  G  L  F  T  L  V  L  P  V
301  aacatcgcggagcacctgctgcagtactggcccttcggggagctgctctgcaagctggtg
     N  I  A  E  H  L  L  Q  Y  W  P  F  G  E  L  L  C  K  L  V
361  ctggccgtcgaccactacaacatcttctccagcatctacttcctagccgtgatgagcgtg
     L  A  V  D  H  Y  N  I  F  S  S  I  Y  F  L  A  V  M  S  V
421  gaccgatacctggtggtgctggccaccgtgaggtcccgccacatgccctggcgcacctac
     D  R  Y  L  V  V  L  A  T  V  R  S  R  H  M  P  W  R  T  Y
481  cgggggggcgaaggtcgccagcctgtgtgtctggctgggcgtcacggtcctggttctgccc
     R  G  A  K  V  A  S  L  C  V  W  L  G  V  T  V  L  V  L  P
541  ttcttctctttcgctggcgtctacagcaacgagctgcaggtcccaagctgtgggctgagc
     F  F  S  F  A  G  V  Y  S  N  E  L  Q  V  P  S  C  G  L  S
601  ttcccgtggccccgagcgggtctggttcaaggccagccgtgtctacactttggtcctgggc
     F  P  W  P  E  R  V  W  F  K  A  S  R  V  Y  T  L  V  L  G
661  ttcgtgctgcccgtgtgcaccatctgtgtgctctacacagacctcctgcgcaggctgcgg
     F  V  L  P  V  C  T  I  C  V  L  Y  T  D  L  L  R  R  L  R
721  gccgtgcggctccgctctggagccaaggctctaggcaaggccaggcggaaggtgaccgtc
     A  V  R  L  R  S  G  A  K  A  L  G  K  A  R  R  K  V  T  V
781  ctggtcctcgtcgtgctggccgtgtgcctcctctgctggacgcccttccacctggcctct
     L  V  L  V  V  L  A  V  C  L  L  C  W  T  P  F  H  L  A  S
841  gtcgtggccctgaccacggacctgccccagaccccactggtcatcagtatgtcctacgtc
     V  V  A  L  T  T  D  L  P  Q  T  P  L  V  I  S  M  S  Y  V
901  atcaccagcctcacgtacgccaactcgtgcctgaaccccttcctctacgcctttctagat
     I  T  S  L  T  Y  A  N  S  C  L  N  P  F  L  Y  A  F  L  D
961  gacaacttccggaagaacttccgcagcatattgcggtgctga
     D  N  F  R  K  N  F  R  S  I  L  R  C
```

Fig. 8

```
                        GGC GGG GCC ACC GAG CGG TTA TAG CTG GGC CTG CAG GGG ACC    42
CAC GGC TCG CCT CCA GCC TCC TGC GCT CCG GTA CCT GGG CGT CCC AAC TCC ACT GCG CGC   102
CCA AAC CCA GCC GAG CCG GTT CGT GGC CCG CCC CGC CGG GCG GCC GTC GAC GCG AGC GCC   162

CTG GCG TGG CGC CCA GGG GAG CGG GGG GCT CCC GCG AGC CGG CCG CGG CTG GCA CTG CTG   222
Leu Ala Trp Arg Pro Gly Glu Arg Gly Ala Pro Ala Ser Arg Pro Arg Leu Ala Leu Leu    20

CTG CTT CTG CTC CTG CTG CCG CTG CCC TCC GGC GCG TGG TAC AAG CAC GTG GCG AGT CCC   282
Leu Leu Leu Leu Leu Leu Pro Leu Pro Ser Gly Ala Trp Tyr Lys His Val Ala Ser Pro    40

CGC TAC CAC ACG GTG GGC CGC GCC GCT GGC CTG CTC ATG GGG CTG CGT CGC TCA CCC TAT   342
Arg Tyr His Thr Val Gly Arg Ala Ala Gly Leu Leu Met Gly Leu Arg Arg Ser Pro Tyr    60

CTG TGG CGC CGC GCG CTG CGC GCG GCC GCC GGG CCC CTG GCC AGG GAC ACC CTC TCC CCC   402
Leu Trp Arg Arg Ala Leu Arg Ala Ala Ala Gly Pro Leu Ala Arg Asp Thr Leu Ser Pro    80

GAA CCC GCA GCC CGC GAG GCT CCT CTC CTG CTG CCC TCG TGG GTT CAG GAG CTG TGG GAG   462
Glu Pro Ala Ala Arg Glu Ala Pro Leu Leu Leu Pro Ser Trp Val Gln Glu Leu Trp Glu   100

ACG CGA CGC AGG AGC TCC CAG GCA GGG ATC CCC GTC CGT GCG CCC CGG AGC CCG CGC GCC   522
Thr Arg Arg Arg Ser Ser Gln Ala Gly Ile Pro Val Arg Ala Pro Arg Ser Pro Arg Ala   120

CCA GAG CCT GCG CTG GAA CCG GAG TCC CTG GAC TTC AGC GGA GCT GGC CAG AGA CTT CGG   582
Pro Glu Pro Ala Leu Glu Pro Glu Ser Leu Asp Phe Ser Gly Ala Gly Gln Arg Leu Arg   140

AGA GAC GTC TCC CGC CCA GCG GTG GAC CCC GCA GCA AAC CGC CTT GGC CTG CCC TGC CTG   642
Arg Asp Val Ser Arg Pro Ala Val Asp Pro Ala Ala Asn Arg Leu Gly Leu Pro Cys Leu   160

GCC CCC GGA CCG TTC TGA CAG CGT CCC CCG CCC GCC CGT GGC GCC TCC GCG CCT GAC CCA   702
Ala Pro Gly Pro Phe ***                                                            165

GGA GGA GTG GCC GCG CG                                                             719
```

Fig. 9

```
                             CC TCC GGA GCC AGT TCC TGG TCC GCC CCG CCG GGA GCC GTC AGC    44

ATG AAC CCC CGG GCA CGC GGC ATG GGA GCG CGG GGC CCG GGA CCG GGG GCC ACT GCG AGG   104
Met Asn Pro Arg Ala Arg Gly Met Gly Ala Arg Gly Pro Gly Pro Gly Ala Thr Ala Arg    20

CGC CGG CTG CTG GCA TTG CTG TTA CTG CTG CTG CTG CTG CCG CTG CCC GCC CGT GCC TGG   164
Arg Arg Leu Leu Ala Leu Leu Leu Leu Leu Leu Leu Leu Pro Leu Pro Ala Arg Ala Trp    40

TAC AAG CAC ACG GCG AGT CCC CGC TAC CAC ACG GTG GGC CGC GCC GCG GGC CTG CTC ATG   224
Tyr Lys His Thr Ala Ser Pro Arg Tyr His Thr Val Gly Arg Ala Ala Gly Leu Leu Met    60

GGG CTG CGC CGC TCG CCC TAC ATG TGG CGC CGC GCG CTG CGC CCG GCG GCC GGG CCC CTG   284
Gly Leu Arg Arg Ser Pro Tyr Met Trp Arg Arg Ala Leu Arg Pro Ala Ala Gly Pro Leu    80

GCC TGG GAC ACT TTC GGC CAG GAC GTG CCC CCT CGG GGA CCC TCC GCC AGG AAC GCC CTC   344
Ala Trp Asp Thr Phe Gly Gln Asp Val Pro Pro Arg Gly Pro Ser Ala Arg Asn Ala Leu   100

TCT CCG GGG CCC GCC CCT CGC GAC GCT CCG CTG CTT CCC CCC GGG GTT CAG ACA CTG TGG   404
Ser Pro Gly Pro Ala Pro Arg Asp Ala Pro Leu Leu Pro Pro Gly Val Gln Thr Leu Trp   120

CAG GTC CGA CGC GGA AGC TTC CGC TCC GGG ATC CCG GTC AGT GCG CCC CGC AGC CCG CGC   464
Gln Val Arg Arg Gly Ser Phe Arg Ser Gly Ile Pro Val Ser Aal Pro Arg Ser Pro Arg   140

GCC CGG GGG TCC GAG CCG CAA CCG GAA TTG GGC GCC TCT TCC TGG ACC TCG GCG GAG TAG   524
Ala Arg Gly Ser Glu Pro Gln Pro Glu Leu Gly Ala Ser Ser Trp Thr Ser Ala Glu ***   159

ACC AGA GCC TTC GGA GAG TCT TCA GCT CAG CGG TGG TCT GC                            565
```

Fig. 10

```
                                      TGT AGT CGC ACC AAC TGA CTA GTC TCT TCC ATC CTC   36
CGG AGC TCC GAC GTT CTC GGG GAC ATA AAC CCT GTT CTT GTC CTA ACC CGC CAA GGG GCC   96

ATG GAC TTG AGC GCG CTG GCG TCG AGC AGA GAA GTA CGG GGC CCT GGG CCC GGG GCT CCG   156
Met Asp Leu Ser Ala Leu Ala Ser Ser Arg Glu Val Arg Gly Pro Gly Pro Gly Ala Pro    20

GTG AAC CGG CCC CTG CTA CCG CTA CTG CTG CTT CTG CTC TTG CTA CCT CTG CCC GCC AGC   216
Val Asn Arg Pro Leu Leu Pro Leu Leu Leu Leu Leu Leu Leu Pro Leu Pro Ala Ser       40

GCC TGG TAC AAG CAC GTG GCG AGC CCT CGC TAT CAC ACA GTG GGT CGT GCC TCC GGG CTG   276
Ala Trp Tyr Lys His Val Ala Ser Pro Arg Tyr His Thr Val Gly Arg Ala Ser Gly Leu    60

CTC ATG GGG CTG CGC CGC TCG CCC TAC CTG TGG CGC CGT GCC TTG GGT GGG GCC GCT GGA   336
Leu Met Gly Leu Arg Arg Ser Pro Tyr Leu Trp Arg Arg Ala Leu Gly Gly Ala Ala Gly    80

CCG CTC GTG GGG CTC CCG GGA CAG ATG GCC CGC AGC GCT CTC CTG CTT CCT TCC CCC GGG   396
Pro Leu Val Gly Leu Pro Gly Gln Met Ala Arg Ser Ala Leu Leu Leu Pro Ser Pro Gly   100

CAG GAG CTG TGG GAG GTA CGA AGC AGG AGT TCA CCG GCA GGA CTT CCC GTG CAT GCA ACC   456
Gln Glu Leu Trp Glu Val Arg Ser Arg Ser Ser Pro Ala Gly Leu Pro Val His Ala Thr   120

CGG AGT CTG CGG GAC CTG GAG GGA GCC GGC CAA CCT GAG CAG TCG CTA AGC TTT CAG TCC   516
Arg Ser Leu Arg Asp Leu Glu Gly Ala Gle Gln Pro Glu Gln Ser Leu Ser Phe Gln Ser   140

TGG ACT TCA GCA GAG CCC GCT GCT AGA GCC TTC GGT GAG ACG CTT CGT GCC CAG CCA TGG   576
Trp Thr Ser Ala Glu Pro Ala Ala Arg Ala Phe Gly Glu Thr Leu Arg Ala Gln Pro Trp   160

TTC CTG CAG CAA ATC ATC TTT GCC GAT CCT GTC AGG CTC GAC GAC CGT CTC AAG AAC CGA   636
Phe Leu Gln Gln Ile Ile Phe Ala Asp Pro Val Arg Leu Asp Asp Arg Leu Lys Asn Arg   180

TGG CGC CCC CGT GCT TGA CCT AAG CAG GAG CAC AGC TTG TAG CTC CAG                   684
Trp Arg Pro Arg Ala ***                                                           185
```

Fig. 11

```
                    TGA CTG GTC TCC ATC CTC TGG AGC TCC GAC GTG CTC GTT   39
CTC GGA GAC ATA AAC CCA GTT CTT GTC CTA ACC CTC CAA GGG GCA ATT GAC GTG AGC GCG   99

CTG GCG TCT AAC AGA GAA GTA CGG GGC CCT GGG CCC GGG ACT CCC AGG AAC CGG CCC CTG  159
Leu Ala Ser Asn Arg Glu Val Arg Gly Pro Gly Pro Gly Thr Pro Arg Asn Arg Pro Leu   20

CTG CCC CTG CTG CTG CTT CTG CTC TTG CTA CCG CTG CCC GCC AGC GCC TGG TAT AAG CAC  219
Leu Pro Leu Leu Leu Leu Leu Leu Leu Pro Leu Pro Ala Ser Ala Trp Tyr Lys His    40

GTG GCG AGT CCC CGC TAT CAC ACA GTG GGT CGT GCC TCC GGG CTG CTC ATG GGG CTG CGC  279
Val Ala Ser Pro Arg Tyr His Thr Val Gly Arg Ala Ser Gly Leu Leu Met Gly Leu Arg   60

CGC TCG CCC TAC CAG TGG CGC CGT GCC CTG GGC GGG GCT GCT GGA CCC CTC TCC CGG CTC  339
Arg Ser Pro Tyr Gln Trp Arg Arg Ala Leu Gly Gly Ala Ala Gly Pro Leu Ser Arg Leu   80

CCA GGA CCG GTC GCC CGC GGC GCT CTC CTG CTT CCT TCC TCA GGG CAG GAG CTG TGG GAG  399
Pro Gly Pro Val Ala Arg Gly Ala Leu Leu Leu Pro Ser Ser Gly Gln Glu Leu Trp Glu  100

GTA CGA AGC AGG AGC TCA CCT GCA GGG CTT CCC GTC CAT GCA CCC TGG AGT CCG CGG GAC  459
Val Arg Ser Arg Ser Ser Pro Ala Gly Leu Pro Val His Ala Pro Trp Ser Pro Arg Asp  120

CTG GAG GGA GTC CGC CAA CCG GAG CAG TCG CTA AGC CTT CAC TCC TGG ATC TCA GAG GAG  519
Leu Glu Gly Val Arg Gln Pro Glu Gln Ser Leu Ser Leu His Ser Trp Ile Ser Glu Glu  140

CCC GCT GCT AGA GCC TTC GGA GAG ACG CTT CGT GCC CAG CCA TGG TTC CTG CAG CAA GTC  579
Pro Ala Ala Arg Ala Phe Gly Glu Thr Leu Arg Ala Gln Pro Trp Phe Leu Gln Gln Val  160

ATC TTT GCC GAT CCT GTC AGG CCC AAG AAC CGA TGG CGC CCC CAT GCT TGA CCT AGG CAG  639
Ile Phe Ala Asp Pro Val Arg Pro Lys Asn Arg Trp Arg Pro His Ala ***               176
GAG CAC ACC TTC AAG CTC CA                                                        659
```

PEPTIDE HAVING APPETITE STIMULATING ACTIVITY

This application is the National Phase filing of International Patent Application No. PCT/JP01/05257, filed 20 Jun. 2001.

1. Field of Invention

The present invention relates to a novel brain-derived polypeptide and a DNA encoding the same, as well as a method of screening drugs using the novel polypeptide, preferably a method of screening drugs (appetite (eating) stimulants, antiobesity drugs, etc.) using both GPR8 (O'Dowd, B. F., et al., Genomics, 28, 84–91, 1995), which is a receptor of the novel polypeptide of the present invention, and the novel polypeptide of the present invention, compounds obtained by such screening, and the like.

2. Background Art

Important biological functions including maintenance of homeostasis in vivo, reproduction, development of individuals, metabolism, growth, control of the nervous, circulatory, immune, digestive or metabolic system, sensory adaptation, etc. are regulated by cells that receive endogenous factors such as various hormones and neurotransmitters or sensory stimulation like light or odor, via specific receptors present on cell membranes reserved for these factors or stimulation and interact with them. Many of these receptors for hormones or neurotransmitters by such functional regulation are coupled to guanine nucleotide-binding proteins (hereinafter, sometimes merely referred to as G proteins), and are characterized by developing a variety of functions through mediation of intracellular signal transduction via activation of the G proteins. In addition, these receptor proteins possess common seven transmembrane domains. Based on the foregoing, these receptors are thus collectively referred to as G protein-coupled receptors or seven transmembrane receptors. As such it is known that various hormones or neurotransmitters and their receptor proteins are present and interact with each other to play important roles for regulating the biological functions. However, it often remains unclear if there are any other unknown substances (hormones, neurotransmitters, etc.) and receptors to these substances.

In recent years, accumulated sequence information of human genome DNA or various human tissue-derived cDNA by random sequencing and rapid progress in gene analysis technology have been accelerating the investigation of human genome. Based on this, it has been clarified that there are many genes supposed to encode proteins with unknown functions. G protein-coupled receptors not only have seven transmembrane domains but many common sequences are present their nucleic acids or amino acids. Thus, they can be clearly identified to be G protein-coupled receptors in such proteins. On the other hand, these G protein-coupled receptor genes are obtained by polymerase chain reaction (hereinafter abbreviated as PCR) utilizing such a structural similarity. In these G protein-coupled receptors thus obtained so far, ligands to some receptors that are subtypes having high homology in structure to known receptors may be readily predictable but in most cases, their endogenous ligands are unpredictable so that ligands corresponding to these receptors are hardly found. For this reason, these receptors are termed orphan receptors. It is likely that unidentified endogenous ligands to such orphan receptors would take part in biological phenomena poorly analyzed because the ligands were unknown. When such ligands are associated with important physiological effects or pathologic conditions, it is expected that development of these receptor agonists or antagonists will result in breakthrough new drugs (Stadel, J. et al., TiPS, 18, 430–437, 1997; Marchese, A. et al., TiPS, 20, 370–375, 1999; Civelli, O. et al., Brain Res., 848, 63–65, 1999). Until now, however, there are few examples to actually identify ligands to orphan G protein-coupled receptors.

Recently, some groups attempted to investigate ligands to these orphan receptors and reported isolation/structural determination of ligands which are novel physiologically active peptides. Independently Reinsheid et al. and Meunier et al. introduced cDNA encoding orphan G protein-coupled receptor LC132 or ORL1 into animal cells to express a receptor, isolated a novel peptide from swine brain or rat brain extract, which was named orphanin FQ or nociceptin with reference to its response, and determined its sequence (Reinsheid, R. K. et al., Science, 270, 792–794, 1995; Meunier, J.-C. et al., Nature, 377, 532–535, 1995). This peptide was reported to be associated with pain. Further research on the receptor in knockout mouse reveals that the peptide takes part in memory (Manabe, T. et al., Nature, 394, 577–581, 1998).

Subsequently, novel peptides such as PrRP (prolactin releasing peptide), orexin, apelin, ghrelin and GALP (galanin-like peptide), etc. were isolated as ligands to orphan G protein-coupled receptors (Hinuma, S. et al., Nature, 393, 272–276, 1998; Sakurai, T. et al., Cell, 92, 573–585, 1998; Tatemoto, K. et al., Biohem. Biophys. Res. Commun., 251, 471–476, 1998; Kojima, M. et al., Nature, 402, 656–660, 1999; Ohtaki, T. et al., J. Biol. Chem., 274, 37041–37045, 1999). On the other hand, some receptors to physiologically active peptides, which were hitherto unknown, were clarified. It was revealed that a receptor to motilin associated with contraction of intestinal tracts was GPR38 (Feighner, S. D. et al., Science, 284, 2184–2188, 1999). Furthermore, SLC-1 was identified to be a receptor to MCH (Chambers, J. et al., Nature, 400, 261–265, 1999; Saito, Y. et al., Nature, 400, 265–269, 1999; Shimomura, Y. et al., Biochem. Biophys. Res. Commun., 261, 622–626, 1999; Lembo, P. M. C. et al., Nature Cell Biol., 1, 267–271, 1999; Bachner, D. et al., FEBS Lett., 457, 522–524, 1999). Also, GPR14 (SENR) was reported to be a receptor to urotensin II (Ames, R. S. et al., Nature, 401, 282–286, 1999; Mori, M. et al., Biochem. Biophys. Res. Commun., 265, 123–129, 1999; Nothacker, H. P. et al., Nature Cell Biol., 1, 383–385, 1999, Liu, Q. et al., Biochem. Biophys. Res. Commun., 266, 174–178, 1999). It was shown that MCH took part in obesity since its knockout mice showed the reduced body weight and lean phenotype (Shimada, M. et al., Nature, 396, 670–674, 1998), and because its receptor was revealed, it became possible to explore a receptor antagonist likely to be an antiobesity agent. It is further reported that urotensin II shows a potent action on the cardiocirculatory system, since it induces heart ischemia by intravenous injection to monkey (Ames, R. S. et al., Nature, 401, 282–286, 1999).

As described above, orphan receptors and ligands thereto often take part in a new physiological activity, and it is expected that their clarification will lead to development of new drugs. However, it is known that research on ligands to orphan receptors is accompanied by many difficulties. For example, it is generally unknown what secondary signal transduction system will take place after orphan receptors expressed on cells responded to ligands, and various response system should be examined. Moreover, tissues where ligands are present are not readily predictable so that various tissue extracts should be prepared. Furthermore, since an amount of ligand required to stimulate its receptor is sufficient even in an extremely low concentration when the ligand is a peptide, the amount of such a ligand present in vivo is a trace amount in many cases. In addition, a peptide is digested by peptidase to lose its activity, or undergoes non-specific adsorption so that its recovery becomes poor during purification. Thus, it is normally extremely difficult to extract such a ligand from the living body and isolate an amount of the ligand necessary for determination of its structure. The presence of many orphan receptors was unraveled, but only a very small part of ligands to these receptors were discovered so far due to the foregoing problems.

DISCLOSURE OF THE INVENTION

GPR8 is one of the reported orphan G protein-coupled receptors (O'Dowd, B. F. et al., Genomics, 28, 84–91, 1995). GPR8 has a low homology to somatostatin receptor (SSTR3) and opioid receptors (δ, κ and μ) but it was yet unknown what its ligand was.

It was thus desired to find an endogenous ligand to GPR8 and make direct use of the ligand or make use of a drug screening system using the ligand (preferably in combination with GPR8) to develop pharmaceuticals with quite a new mechanism unknown so far.

The present inventors have made extensive studies to solve the foregoing problems, and as a result, found an endogenous ligand capable of binding to GPR8 in the extract from porcine hypothalamus and successfully purified the same. Furthermore, the inventors have succeeded in cloning of a human homologue of the ligand and found that the ligand has an appetite (eating) stimulating activity and that GPR8 agonist and GPR8 antagonist can be used as an appetite (eating) stimulant and a preventive/therapeutic agent for obesity (antiobesity drug/agent), respectively. Based on these findings, the present invention has come to be accomplished.

That is, the present invention relates to the following features:

(1) A polypeptide capable of binding to a protein or its salt containing the same or substantially the same amino acid sequence as the amino acid sequence represented by SEQ ID NO:4, or its amide or ester, or a salt thereof;

(2) The polypeptide or its amide or ester, or a salt thereof, according to (1), which contains the same or substantially the same amino acid sequence as the amino acid sequence represented by SEQ ID NO:16;

(3) The polypeptide or its amide or ester, or a salt thereof, according to (2), which contains the amino acid sequence represented by SEQ ID NO:16;

(4) The polypeptide or its amide or ester, or a salt thereof, according to (2), wherein substantially the same amino acid sequence is the amino acid sequence represented by SEQ ID NO:6, SEQ ID NO:17, SEQ ID NO:20, SEQ ID NO:21, SEQ ID NO:22, SEQ ID NO:23, SEQ ID NO:24, SEQ ID NO:25, SEQ ID NO:56, SEQ ID NO:57, SEQ ID NO:73, SEQ ID NO:74, SEQ ID NO:91, SEQ ID NO:92, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112 or SEQ ID NO:113;

(5) The polypeptide or its amide or ester, or a salt thereof, according to (1), which contains the amino acid sequence represented by SEQ ID NO:15, SEQ ID NO:42, SEQ ID NO:55, SEQ ID NO:72 or SEQ ID NO:90;

(6) A DNA containing a DNA encoding the polypeptide according to (1);

(7) The DNA according to (6), having the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125;

(8) The DNA according to (6), having the base sequence represented by SEQ ID NO:14, SEQ ID NO:41, SEQ ID NO:54, SEQ ID NO:71 or SEQ ID NO:89;

(9) A recombinant vector containing the DNA according to (6);

(10) A transformant transformed with the recombinant vector according to (9);

(11) A method of manufacturing the polypeptide or its amide or ester, or a salt thereof, according to (1), which comprises culturing the transformant of (10) and producing/accumulating the polypeptide according to (1);

(12) An antibody to the polypeptide or its amide or ester, or a salt thereof, according to (1);

(13) A diagnostic product comprising the DNA according to (6) or the antibody according to (12);

(14) An antisense DNA having a complementary or substantially complementary base sequence to the DNA according to (6) and capable of suppressing expression of said DNA;

(15) A composition comprising the polypeptide or its amide or ester, or a salt thereof, according to (1) (e.g., pharmaceuticals, animal drugs, agricultural chemicals, foodstuff, etc.);

(16) A pharmaceutical composition comprising the polypeptide or its amide or ester, or a salt thereof, according to (1);

(17) An appetite stimulant comprising the polypeptide or its amide or ester, or a salt thereof, according to (1);

(18) A prolactin production promoting agent comprising the polypeptide or its amide or ester, or a salt thereof, according to (1);

(19) A method of screening a compound or its salt that promotes or inhibits the activity of the polypeptide or its amide or ester, or a salt thereof, according to (1), which comprises using the polypeptide or its amide or ester, or a salt thereof, according to (1);

(20) The method of screening according to (19), wherein labeled form of the polypeptide or its amide or ester, or a salt thereof, according to (1) is used;

(21) The method of screening according to (19), wherein a protein containing the same or substantially the same amino acid sequence as the amino acid sequence represented by SEQ ID NO:4 or a salt thereof, or a partial peptide of the protein, its amide or ester, or a salt thereof is further used;

(22) A kit for screening a compound that promotes or inhibits the activity of the polypeptide or its amide or ester, or a salt thereof, according to (1), comprising the polypeptide or its amide or ester, or a salt thereof, according to (1);

(23) A kit for screening according to (22), further comprising a protein containing the same or substantially the same amino acid sequence as the amino acid sequence represented by SEQ ID NO:4 or a salt thereof, or a partial peptide of the protein, its amide or ester, or a salt thereof;

(24) A compound that promotes or inhibits the activity of said polypeptide, or its amide or ester, or a salt thereof, according to (1), which is obtainable using the screening method according to (19) or the screening kit according to (22);

(25) A pharmaceutical composition comprising a compound that promotes or inhibits the activity of said polypeptide, or its amide or ester, or a salt thereof, according to (1), which is obtainable using the screening method according to (19) or the screening kit according to (22);

(26) An antiobesity agent which is obtainable using the screening method according to (19) or the screening kit according to (22);

(27) An appetite stimulant which is obtainable using the screening method according to (19) or the screening kit according to (22);

(28) A prolactin production inhibitor which is obtainable using the screening method according to (19) or the screening kit according to (22);

(29) A method of stimulating appetite which comprises administering to a mammal an effective dose of the polypeptide, its amide or ester, or a salt thereof, according to (1);

(30) A method of preventing/treating obesity which comprises administering to a mammal an effective dose of a compound or its salt that inhibits the activity of the polypeptide, its amide or ester, or a salt thereof, according to (1), which is obtainable using the screening method according to (19) or the screening kit according to (22);

(31) Use of the polypeptide, its amide or ester, or a salt thereof, according to (1), for manufacturing an appetite stimulant;

(32) Use of a compound or its salt that inhibits the activity of the polypeptide, its amide or ester, or a salt thereof, according to (1), for manufacturing an antiobesity agent, which compound is obtainable using the screening method according to (19) or the screening kit according to (22);

(33) A transgenic animal wherein the DNA according to (6) is used;

(34) The transgenic animal according to (33), into which the recombinant vector according to (9) is introduced;

(35) The transgenic animal according to (33) wherein said animal is a non-human mammal;

(36) A knockout animal wherein the DNA according to (6) is inactivated;

(37) The knockout animal according to (36), wherein the DNA according to (6) is inactivated by introduction of other gene;

(38) The knockout animal according to (37) wherein other gene is a reporter gene;

(39) The knockout animal according to (36) wherein the animal is a non-human mammal; and,

(40) A method of screening a compound or its salt having an effect on a disease caused by deficiency/damage of the DNA according to (6), which comprises using the animal according to (33) or (36); etc.

The present invention further provides the following:

(41) The polypeptide, its amide or ester, or a salt thereof, according to (1), wherein substantially the same amino acid sequence as the amino acid sequence represented by SEQ ID NO:16 is an amino acid sequence having at least about 90% homology, preferably at least about 95% homology, and more preferably at least about 98% homology, to the amino acid sequence represented by SEQ ID NO:16;

(42) The polypeptide, its amide or ester, or a salt thereof, according to (1), wherein substantially the same amino acid sequence as the amino acid sequence represented by SEQ ID NO:16 is (i) an amino acid sequence represented by SEQ ID NO:16, of which 1 to 5 (preferably 1 to 3, more preferably 1 or 2, and most preferably 1) amino acids are deleted; (ii) an amino acid sequence represented by SEQ ID NO:16, to which 1 to 5 (preferably 1 to 3, more preferably 1 or 2, and most preferably 1) amino acids are added; (iii) an amino acid sequence represented by SEQ ID NO:16, in which 1 to 5 (preferably 1 to 3, more preferably 1 or 2, and most preferably 1) amino acids are inserted; (iv) an amino acid sequence represented by SEQ ID NO:16, in which 1 to 5 (preferably 1 to 3, more preferably 1 or 2, and most preferably 1) amino acids are substituted with other amino acids; and (v) a combination of the above amino acid sequences; and,

(43) A polypeptide capable of specifically binding to a protein or a salt thereof containing the same or substantially the same amino acid sequence as the amino acid sequence represented by SEQ ID NO:4, or its amide or ester, or a salt thereof; and so on.

BRIEF DESCRIPTION OF THE DRAWINGS

FIG 1 shows the entire base sequence of human GPR8 receptor protein cDNA (SEQ ID NO: 32) and the whole amino acid sequence of human GPR8 receptor protein (SEQ NO: 4) translated therefrom.

FIG. 8 shows the entire base sequence of human homologue precursor protein cDNA of GPR8 ligand peptide (SEQ NO: 41) and the entire amino acid sequence of human homologue precursor receptor protein of GPR8 ligand peptide (SEQ NO: 42) translated therefrom, wherein a putative GPR8 ligand human homologue peptide composed of 23 residues is enclosed in a box.

FIG. 9 shows the entire base sequence of porcine homologue precursor protein cDNA of GPR8 ligand peptide (SEQ ID NO: 54) and the entire amino acid sequence of a porcine homologue precursor receptor protein of GPR8 ligand peptide (SEQ ID NO: 55) translated therefrom, wherein a putative GPR8 ligand porcine homologue peptide composed of 23 residues is enclosed in a box.

FIG. 10 shows the entire base sequence of rat homologue precursor protein cDNA of GPR8 ligand peptide (SEQ ID NO: 71) and the entire amino acid sequence of rat homologue precursor receptor protein of GPR8 ligand peptide (SEQ ID NO: 72) translated therefrom, wherein a putative GPR8 ligand rat homologue peptide composed of 23 residues is enclosed in a box.

FIG. 11 shows the entire base sequence of mouse homologue precursor protein cDNA of GPR8 ligand peptide (SEQ ID NO: 89) and the entire amino acid sequence of mouse homologue precursor receptor protein of GPR8 ligand peptide (SEQ ID NO: 90) translated therefrom, wherein a putative GPR8 ligand human homologue peptide composed of 23 residues is enclosed in a box.

EMBODIMENT FOR CARRYING OUT THE INVENTION

Figure 2:
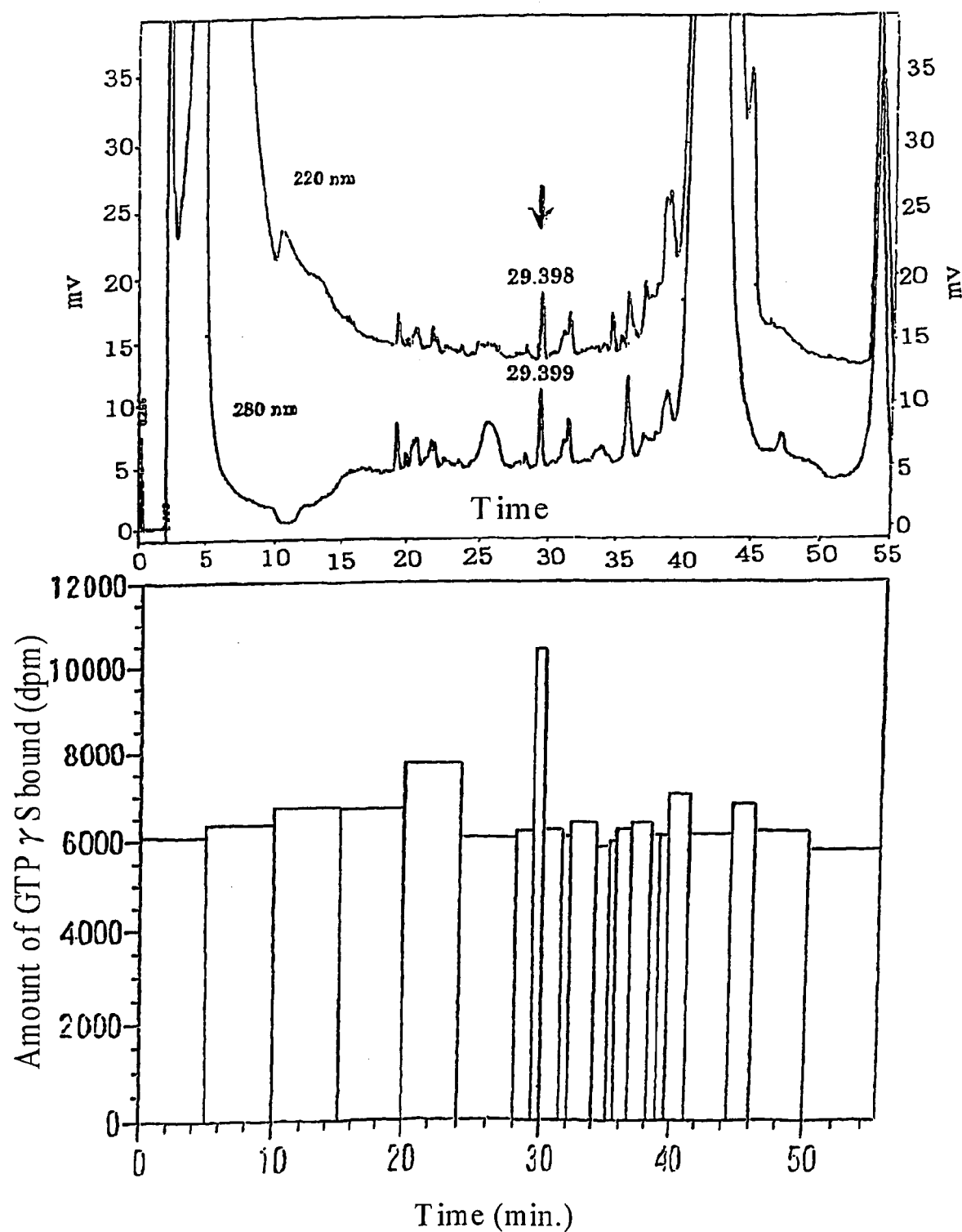
FIG. 2 shows UV absorption of GPR8 ligand in the final stage purification by HPLC using Wakosil-II 3C18HG column and the GTPγ S activity of each peak. The activity was recovered in the peak shown by arrow.

Examples of the "polypeptide capable of binding to a protein or its salt containing the same or substantially the same amino acid sequence as the amino acid sequence represented by SEQ ID NO:4, or its amide or ester, or a salt thereof" of the present invention include a polypeptide or its amide or ester, or a salt thereof, having a dissociation constant in binding to a protein or its salt containing the same or substantially the same amino acid sequence as the amino acid sequence represented by SEQ ID NO:4 of 1 nM or less, preferably not greater than 200 pM, more preferably not greater than 100 pM, much more preferably not greater than 80 pM, and most preferably not greater than 50 pM, and the like.

The polypeptide of the present invention having the same or substantially the same amino acid sequence as the amino acid sequence shown by SEQ ID NO:16 (hereinafter sometimes referred to as the polypeptide of the present invention) may be any polypeptide derived from any cells of human and other warm-blooded animals (e.g. guinea pig, rat, mouse, chicken, rabbit, swine, sheep, bovine, monkey, etc.) (for example, retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), hypothalamus, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; polypeptides derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); the polypeptides may also be synthetic polypeptides.

Substantially the same amino acid sequence as the amino acid sequence represented by SEQ ID NO:16 includes an amino acid sequence having at least about 90% homology, preferably at least about 95% homology, and more preferably at least about 98% homology, to the amino acid sequence represented by SEQ ID NO:16.

Specifically, substantially the same amino acid sequence as the amino acid sequence represented by SEQ ID NO:16 includes, in addition to the amino acid sequences described above:

(i) the amino acid sequence represented by SEQ ID NO:16, of which 1 to 5 (preferably 1 to 3, more preferably 1 or 2, and most preferably 1) amino acids are deleted;

(ii) the amino acid sequence represented by SEQ ID NO:16, to which 1 to 5 (preferably 1 to 3, more preferably 1 or 2, and most preferably 1) amino acids are added;

(iii) the amino acid sequence represented by SEQ ID NO:16, in which 1 to 5 (preferably 1 to 3, more preferably 1 or 2, and most preferably 1) amino acids are inserted;

(iv) the amino acid sequence represented by SEQ ID NO:16, in which 1 to 5 (preferably 1 to 3, more preferably 1 or 2, and most preferably 1) amino acids are substituted with other amino acids; and, (v) a combination of the amino acid sequences (i) through (iv) described above, etc.

Examples of the polypeptide which has substantially the same amino acid sequence as the amino acid sequence shown by SEQ ID NO:16 include a polypeptide containing substantially the same amino acid sequence as the amino acid sequence shown by SEQ ID NO:16 and having an activity substantially equivalent to that of the amino acid sequence represented by SEQ ID NO:16, and the like.

The substantially equivalent activity refers to, e.g., activities possessed by the polypeptide of the present invention, for example, the preventive/therapeutic activities later described, the binding activity to receptors, the cell-stimulating activity on receptor-expressed cells (e.g., the activity that promotes arachidonic acid release, acetylcholine release, intracellular Ca$^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.), and the like.

The term "substantially equivalent activity" is used to mean that these activities are equivalent in nature (for example, biochemically or pharmacologically).

Specific examples of substantially the same amino acid sequence as the amino acid sequence represented by SEQ ID NO:16 are amino acid sequences represented by SEQ ID NO:6, SEQ ID NO:17, SEQ ID NO:20, SEQ ID NO:21, SEQ ID NO:22, SEQ ID NO:23, SEQ ID NO:24, SEQ ID NO:25, SEQ ID NO:56, SEQ ID NO:57, SEQ ID NO:73, SEQ ID NO:74, SEQ ID NO:91, SEQ ID NO:92, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112 or SEQ ID NO:113, and the like.

Specific examples of the polypeptide of the present invention are polypeptides capable of specifically binding to GPR8, including a polypeptide having the amino acid sequence represented by SEQ ID NO:16, a polypeptide having the amino acid sequence represented by SEQ ID NO:6, a polypeptide having the amino acid sequence represented by SEQ ID NO:17, a polypeptide having the amino acid sequence represented by SEQ ID NO:20, a polypeptide having the amino acid sequence represented by SEQ ID NO:21, a polypeptide having the amino acid sequence represented by SEQ ID NO:22, a polypeptide having the amino acid sequence represented by SEQ ID NO:23, a polypeptide having the amino acid sequence represented by SEQ ID NO:24, a polypeptide having the amino acid sequence represented by SEQ ID NO:25, a polypeptide having the amino acid sequence represented by SEQ ID NO:56, a polypeptide having the amino acid sequence represented by SEQ ID NO:57, a polypeptide having the amino acid sequence represented by SEQ ID NO:73, a polypeptide having the amino acid sequence represented by SEQ ID NO:74, a polypeptide having the amino acid sequence represented by SEQ ID NO:91, a polypeptide having the amino acid sequence represented by SEQ ID NO:92, a polypeptide having the amino acid sequence represented by SEQ ID NO:95, a polypeptide having the amino acid sequence represented by SEQ ID NO:96, a polypeptide having the amino acid sequence represented by SEQ ID NO:97, a polypeptide having the amino acid sequence represented by SEQ ID NO:98, a polypeptide having the amino acid sequence represented by SEQ ID NO:99, a polypeptide having the amino acid sequence represented by SEQ ID NO:100, a polypeptide having the amino acid sequence represented by SEQ ID NO:101, a polypeptide having the amino acid sequence represented by SEQ ID NO:102, a polypeptide having the amino acid sequence represented by SEQ ID NO:103, a polypeptide having the amino acid sequence represented by SEQ ID NO:104, a polypeptide having the amino acid sequence represented by SEQ ID NO:105, a polypeptide having the amino acid sequence represented by SEQ ID NO:106, a polypeptide having the amino acid sequence represented by SEQ ID NO:107, a polypeptide having the amino acid sequence represented by SEQ ID NO:108, a polypeptide having the amino acid sequence represented by SEQ ID NO:109, a polypeptide having the amino acid sequence represented by SEQ ID NO:110, a polypeptide having the amino acid sequence represented by SEQ ID NO:111, a polypeptide having the amino acid sequence represented by SEQ ID NO:112 or a polypeptide having the amino acid sequence represented by SEQ ID NO:113, etc.

The polypeptide of the present invention is used to mean that the polypeptide not only includes polypeptides having the activity of binding to the receptor (GPR8) of the present invention later described, the cell-stimulating activity on cells where the receptor of the present invention is expressed (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.), etc., but also includes precursor polypeptides of the polypeptides having those binding activity or cell-stimulating activity.

Specific examples of the precursor polypeptides of the polypeptides having such a binding activity or cell-stimulating activity are polypeptides characterized by containing the same or substantially the same amino acid sequence as the amino acid sequence represented by SEQ ID NO:15, etc.

More specifically, substantially the same amino acid sequence as the amino acid sequence represented by SEQ ID NO:15 refers to amino acid sequences having at least about 80% homology, preferably at least about 90% homology, and more preferably at least about 95% homology, to the amino acid sequence represented by SEQ ID NO:15, etc.

In particular, substantially the same amino acid sequences as the amino acid sequence represented by SEQ ID NO:15 include, in addition to the amino acid sequences described above:

(i) the amino acid sequence represented by SEQ ID NO:15, of which 1 to 15 (preferably 1 to 10, more preferably 1 or 5, and most preferably 1 to 3) amino acids are deleted;

(ii) the amino acid sequence represented by SEQ ID NO:15, to which 1 to 100 (preferably 1 to 50, more preferably 1 or 5, and most preferably 1 to 3) amino acids are added;

(iii) the amino acid sequence represented by SEQ ID NO:15, in which 1 to 15 (preferably 1 to 10, more preferably 1 or 5, and most preferably 1 to 3) amino acids are inserted;

(iv) the amino acid sequence represented by SEQ ID NO:15, in which 1 to 15 (preferably 1 to 10, more preferably 1 or 5, and most preferably 1 to 3) amino acids are substituted with other amino acids; and, (v) a combination of the amino acid sequences (i) through (iv) described above, etc.

Specific examples of substantially the same amino acid sequence as the amino acid sequence represented by SEQ ID NO:15 include an amino acid sequence represented by SEQ ID NO:42, SEQ ID NO:55, SEQ ID NO:72 or SEQ ID NO:90.

Specific examples of the precursor polypeptide described above are a polypeptide having the amino acid sequence represented by SEQ ID NO:15, a polypeptide having the amino acid sequence represented by SEQ ID NO:42, a polypeptide having the amino acid sequence represented by SEQ ID NO:55, a polypeptide having the amino acid sequence represented by SEQ ID NO:72 or a polypeptide having the amino acid sequence represented by SEQ ID NO:90, and the like.

In various receptors, the receptors to the polypeptide of the present invention are used to mean those that have the activity binding to the polypeptide of the present invention and the cell-stimulating activity of the receptor-expressed cells (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.) is observed by the polypeptide of the present invention, and the like.

Specifically, the receptors include GPR8 (O'Dowd, B. F. et al., Genomics, 28, 84–91, 1995; a protein composed of the amino acid sequence represented by SEQ ID NO:4), which is an orphan G protein-coupled receptor, a protein containing the amino acid sequence substantially the same as GPR8, namely, an amino acid sequence substantially the same as the amino acid sequence represented by SEQ ID NO:4, etc.

The protein of the present invention having the same or substantially the same amino acid sequence as the amino acid sequence represented by SEQ ID NO:4 (hereinafter sometimes collectively referred to as the receptor of the present invention) may be any protein derived from any cells of human and other warm-blooded animals (e.g. guinea pig, rat, mouse, chicken, rabbit, swine, sheep, bovine, monkey, etc.) (for example, retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), hypothalamus, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; proteins derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); the proteins may also be synthetic proteins.

The amino acid sequence substantially the same as the amino acid sequence represented by SEQ ID NO:4 includes amino acid sequences having at least about 70% homology, preferably at least about 80% homology, and more preferably at least about 90% homology, to the amino acid sequence represented by SEQ ID NO:4, etc.

In particular, the amino acid sequences substantially the same as the amino acid sequence represented by SEQ ID NO:4 include, in addition to the amino acid sequences described above:

(i) the amino acid sequence represented by SEQ ID NO:4, of which 1 to 15 (preferably 1 to 10, more preferably 1 or 5, and most preferably 1 to 3) amino acids are deleted;

(ii) the amino acid sequence represented by SEQ ID NO:4, to which 1 to 15 (preferably 1 to 10, more preferably 1 or 5, and most preferably 1 to 3) amino acids are added;

(iii) the amino acid sequence represented by SEQ ID NO:4, in which 1 to 15 (preferably 1 to 10, more preferably 1 or 5, and most preferably 1 to 3) amino acids are inserted;

(iv) the amino acid sequence represented by SEQ ID NO:4, in which 1 to 15 (preferably 1 to 10, more preferably 1 or 5, and most preferably 1 to 3) amino acids are substituted with other amino acids; and, (v) a combination of the amino acid sequences (i) through (iv) described above, etc.

Any partial peptide can be used as the partial peptide of the receptor to the polypeptide of the present invention (hereinafter sometimes referred to as the partial peptide of the present invention), as long as it is a partial peptide available for the method of screening drugs, etc. later described. Preferably, there may be employed partial peptides capable of binding to the polypeptide of the present invention, partial peptides containing an amino acid sequence corresponding to the extracellular region, and the like.

Specifically, the partial peptide includes a partial peptide containing 1 or more partial amino acid sequences selected from the partial amino acid sequences of 1 (Met)–123 (Phe), 301 (Asn)–358 (Lys), 548 (Tyr)–593 (Arg) and 843 (Ala) –895 (Ile) in the amino acid sequence represented by SEQ ID NO:4; etc.

The polypeptides, receptors or partial peptides of the present invention are represented in accordance with the conventional way of describing peptides, that is, the N-terminus (amino terminus) at the left hand and the C-terminus (carboxyl terminus) at the right hand. In the polypeptides of the present invention including the polypeptides containing the amino acid sequence shown by SEQ ID NO:1, the C-terminus is usually in the form of a carboxyl group (—COOH) or a carboxylate (—COO⁻) but the C-terminus may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; an aralkyl having 7 to 14 carbon atoms such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like, which is used widely as an ester for oral administration may also be used.

Where the polypeptides, receptors or partial peptides of the present invention contain a carboxyl group (or a carboxylate) at a position other than the C-terminus, it may be amidated or esterified and such an amide or ester is also included within the polypeptide of the present invention. In this case, the ester group may be the C-terminal esters, etc. described above.

The polypeptides, receptors or partial peptides of the present invention further include those wherein the amino group at the N-terminal amino acid residues (e.g., methionine residue) is protected with a protecting group (e.g., a $C_{1-6}$ acyl group, e.g., a $C_{1-6}$ alkanoyl group such as formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ acyl group, e.g., a $C_{1-6}$ alkanoyl group such as formyl group, acetyl group, etc.), or conjugated proteins such as so-called glycoproteins having sugar chains, and the like.

As salts of the polypeptides, receptors or partial peptides of the present invention, there are salts with physiologically acceptable acids (e.g., inorganic acids, organic acids) or bases (e.g., alkali metal bases), etc., with particular preference in the form of physiologically acceptable acid addition salts. Examples of such salts are salts with inorganic acids (e.g., hydrochloric acid, phosphoric acid, hydrobromic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptides, receptors or partial peptides of the present invention may be manufactured by a publicly known method used to purify polypeptides from human or other mammalian cells or tissues described above, or may also be manufactured by culturing a transformant containing a DNA encoding the polypeptide, as will be later described. Furthermore, the polypeptides, receptors or partial peptides may also be manufactured by protein synthesis, which will be described hereinafter, or by its modifications.

Where the polypeptides, receptors or partial peptides are manufactured from human or mammalian tissues or cells, human or mammalian tissues or cells are homogenized and extracted with an acid or the like, and the extract is purified and isolated by a combination of chromatography techniques such as reversed phase chromatography, ion exchange chromatography, and the like.

To synthesize the polypeptides, receptors or partial peptides of the present invention or salts thereof, or amides thereof, commercially available resins that are used for polypeptide synthesis may normally be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl- Fmoc-aminoethyl) phenoxy resin, etc. Using these resins, amino acids, in which α-amino groups and functional groups on the side chains are appropriately protected, are condensed on the resin in the order of the sequences of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptides, receptors or partial peptides, or amides thereof.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$—Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group for the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptides, receptors or partial peptides of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group of the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to obtain the desired crude polypeptide. This crude polypeptide is purified by various known purification means. Lyophilization of the major fraction gives the amide of the desired polypeptides, receptors or partial peptides thereof.

To prepare the esterified polypeptides, receptors or partial peptides thereof, for example, the α-carboxyl group of the carboxy terminal amino acid is condensed with a desired alcohol to prepare the amino acid ester, which is followed by procedure similar to the preparation of the amidated protein above to give the desired esterified polypeptides, receptors or partial peptides thereof.

The polypeptides, receptors or partial peptides of the present invention can be manufactured by publicly known methods for peptide synthesis; or the partial peptides of the receptors may be manufactured by cleaving the receptors with an appropriate peptidase. For the peptide synthesis, for example, either solid phase synthesis or liquid phase synthesis may be used. That is, the partial peptides or amino acids that can construct the polypeptides, receptors or partial peptides of the present invention are condensed with the remaining part. Where the product contains protecting groups, these protecting groups are removed to give the desired peptide. Publicly known methods for condensation and elimination of the protecting groups are described in 1)–5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography, recrystallization, etc. to give the polypeptides, receptors or partial peptides of the present invention. When the polypeptides, receptors or partial peptides of the present invention obtained by the above methods is in a free form, they may be converted into appropriate salts by publicly known methods or modifications thereof; when they are obtained in a salt form, they may be converted into their free form or in the form of different salts by publicly known methods or modifications thereof.

For the DNA encoding the polypeptides, receptors or partial peptides of the present invention, any DNA can be used so long as it contains the base sequence encoding the polypeptides, receptors or partial peptides of the present invention described above. The DNA may be any of genomic DNA, genomic DNA library, cDNA derived from the cells/tissues described above, cDNA library derived from the cells/tissues described above, and synthetic DNA. The vector to be used for the library may be any of bacteriophage, plasmid, cosmid, phagemid, and the like. In addition, the DNA can be directly amplified by reverse transcriptase polymerase chain reaction (hereinafter abbreviated as RT-PCR) with total RNA or mRNA fraction prepared from the above-described cells or tissues.

The DNA encoding the polypeptide of the present invention may be any DNA, so long as it is, for example, (1) a DNA containing the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125, (2) a DNA having a base sequence hybridizable under high stringent conditions to the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125 and encoding a polypeptide which has the activity substantially equivalent to that of the polypeptide of the present invention, (3) a DNA containing the base sequence represented by SEQ ID NO:14, SEQ ID NO:41, SEQ ID NO:54, SEQ ID NO:71 or SEQ ID NO:89, or (4) a DNA containing a base sequence hybridizable to the base sequence represented by SEQ ID NO:14, SEQ ID NO:41, SEQ ID NO:54, SEQ ID NO:71 or SEQ ID NO:89 under high stringent conditions; etc.

Specific examples of the DNA that is hybridizable under high stringent conditions to the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125, or to the base sequence represented by SEQ ID NO:14, SEQ ID NO:41, SEQ ID NO:54, SEQ ID NO:71 or SEQ ID NO:89 are DNAs containing base sequences having at least about 70% homology, preferably at least about 80% homology, more preferably at least about 90% homology and most preferably at least about 95% homology, to the base sequence represented by SEQ ID NO:18, SEQ ID NO:19, SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:75, SEQ ID NO:76, SEQ ID NO:93, SEQ ID NO:94, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124 or SEQ ID NO:125, or by SEQ ID NO:14, SEQ ID NO:41, SEQ ID NO:54, SEQ ID NO:71 or SEQ ID NO:89; and the like.

The hybridization can be carried out by publicly known methods or by modifications thereof, for example, according to the method described in Molecular Cloning, 2nd Ed., J. Sambrook et al., Cold Spring Harbor Lab. Press, 1989, etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically;

(i) a DNA containing the base sequence represented by SEQ ID NO:18 or the like is used as the DNA encoding the polypeptide containing the amino acid sequence represented by SEQ ID NO:16;

(ii) a DNA containing the base sequence represented by SEQ ID NO:19 or the like is used as the DNA encoding the polypeptide containing the amino acid sequence represented by SEQ ID NO:17;

(iii) a DNA containing the base sequence represented by SEQ ID NO:26 or the like is used as the DNA encoding the polypeptide containing the amino acid sequence represented by SEQ ID NO:20;

(iv) a DNA containing the base sequence represented by SEQ ID NO:27 or the like is used as the DNA encoding the polypeptide containing the amino acid sequence represented by SEQ ID NO:21;

(v) a DNA containing the base sequence represented by SEQ ID NO:28 or the like is used as the DNA encoding the polypeptide containing the amino acid sequence represented by SEQ ID NO:22;

(vi) a DNA containing the base sequence represented by SEQ ID NO:29 or the like is used as the DNA encoding the polypeptide containing the amino acid sequence represented by SEQ ID NO:23;

(vii) a DNA containing the base sequence represented by SEQ ID NO:30 or the like is used as the DNA encoding the polypeptide containing the amino acid sequence represented by SEQ ID NO:24;

(viii) a DNA containing the base sequence represented by SEQ ID NO:31 or the like is used as the DNA encoding the polypeptide containing the amino acid sequence represented by SEQ ID NO:25;

(ix) a DNA containing the base sequence represented by SEQ ID NO:58 or the like is used as the DNA encoding the polypeptide containing the amino acid sequence represented by SEQ ID NO:56;

(x) a DNA containing the base sequence represented by SEQ ID NO:59 or the like is used as the DNA encoding the polypeptide containing the amino acid sequence represented by SEQ ID NO:57;

(xi) a DNA containing the base sequence represented by SEQ ID NO:75 or the like is used as the DNA encoding the polypeptide containing the amino acid sequence represented by SEQ ID NO:73;

(xii) a DNA containing the base sequence represented by SEQ ID NO:76 or the like is used as the DNA encoding the polypeptide containing the amino acid sequence represented by SEQ ID NO:74;

(xiii) a DNA containing the base sequence represented by SEQ ID NO:93 or the like is used as the DNA encoding the polypeptide containing the amino acid sequence represented by SEQ ID NO:91;

(xiv) a DNA containing the base sequence represented by SEQ ID NO:94 or the like is used as the DNA encoding the polypeptide containing the amino acid sequence represented by SEQ ID NO:92;

(xv) a DNA containing the base sequence represented by SEQ ID NO:18 or the like is used as the DNA encoding the polypeptide containing the amino acid sequence represented by SEQ ID NO:95;

(xvi) a DNA containing the base sequence represented by SEQ ID NO:114 or the like is used as the DNA encoding the polypeptide containing the amino acid sequence represented by SEQ ID NO:96;

(xvii) a DNA containing the base sequence represented by SEQ ID NO:115 or the like is used as the DNA encoding the polypeptide containing the amino acid sequence represented by SEQ ID NO:97;

(xviii) a DNA containing the base sequence represented by SEQ ID NO:116 or the like is used as the DNA encoding the polypeptide containing the amino acid sequence represented by SEQ ID NO:98;

(xix) a DNA containing the base sequence represented by SEQ ID NO:117 or the like is used as the DNA encoding the polypeptide containing the amino acid sequence represented by SEQ ID NO:99;

(xx) a DNA containing the base sequence represented by SEQ ID NO:118 or the like is used as the DNA encoding the polypeptide containing the amino acid sequence represented by SEQ ID NO:100;

(xxi) a DNA containing the base sequence represented by SEQ ID NO:119 or the like is used as the DNA encoding the polypeptide containing the amino acid sequence represented by SEQ ID NO:101;

(xxii) a DNA containing the base sequence represented by SEQ ID NO:120 or the like is used as the DNA encoding the polypeptide containing the amino acid sequence represented by SEQ ID NO:102;

(xxiii) a DNA containing the base sequence represented by SEQ ID NO:58 or the like is used as the DNA encoding the polypeptide containing the amino acid sequence represented by SEQ ID NO:103;

(xxiv) a DNA containing the base sequence represented by SEQ ID NO:75 or the like is used as the DNA encoding the polypeptide containing the amino acid sequence represented by SEQ ID NO:104;

(xxv) a DNA containing the base sequence represented by SEQ ID NO:18 or the like is used as the DNA encoding the polypeptide containing the amino acid sequence represented by SEQ ID NO:105;

(xxvi) a DNA containing the base sequence represented by SEQ ID NO:18 or the like is used as the DNA encoding the polypeptide containing the amino acid sequence represented by SEQ ID NO:106;

(xxvii) a DNA containing the base sequence represented by SEQ ID NO:121 or the like is used as the DNA encoding the polypeptide containing the amino acid sequence represented by SEQ ID NO:107;

(xxviii) a DNA containing the base sequence represented by SEQ ID NO:122 or the like is used as the DNA encoding the polypeptide containing the amino acid sequence represented by SEQ ID NO:108;

(xxix) a DNA containing the base sequence represented by SEQ ID NO:123 or the like is used as the DNA encoding the polypeptide containing the amino acid sequence represented by SEQ ID NO:109;

(xxx) a DNA containing the base sequence represented by SEQ ID NO:124 or the like is used as the DNA encoding the polypeptide containing the amino acid sequence represented by SEQ ID NO:110;

(xxxi) a DNA containing the base sequence represented by SEQ ID NO:125 or the like is used as the DNA encoding the polypeptide containing the amino acid sequence represented by SEQ ID NO:6;

(xxxii) a DNA containing the base sequence represented by SEQ ID NO:121 or the like is used as the DNA encoding the polypeptide containing the amino acid sequence represented by SEQ ID NO:111;

(xxxiii) a DNA containing the base sequence represented by SEQ ID NO:18 or the like is used as the DNA encoding the polypeptide containing the amino acid sequence represented by SEQ ID NO:112;

(xxxiv) a DNA containing the base sequence represented by SEQ ID NO:121 or the like is used as the DNA encoding the polypeptide containing the amino acid sequence represented by SEQ ID NO:113; and the like.

The DNA encoding the receptor of the present invention includes, for example, a DNA having the base sequence represented by SEQ ID NO: 32, or a DNA having a base sequence hybridizable to the base sequence represented by SEQ ID NO: 32 under high stringent conditions and encoding a polypeptide having an activity substantially equivalent to that of the receptor of the present invention, and the like. Any of such DNAs may be employed.

Examples of the DNA that is hybridizable to the base sequence represented by SEQ ID NO: 32 include a DNA containing a base sequence having at least about 70% homology, preferably at least about 80% homology, more preferably at least about 90% homology and most preferably at least about 95% homology, to the base sequence represented by SEQ ID NO: 32, and the like.

The hybridization can be carried out by publicly known methods or by modifications thereof, for example, according to the method described in Molecular Cloning, 2nd Ed., J. Sambrook et al., Cold Spring Harbor Lab. Press, 1989, etc. A commercially available library may also be used according to the instructions of the attached manufacturer's protocol. The hybridization can be carried out preferably under high stringent conditions.

The high stringent conditions used herein are, for example, those in a sodium concentration at approximately 19 to 40 mM, preferably approximately 19 to 20 mM at a temperature of approximately 50 to 70° C., preferably approximately 60 to 65° C. In particular, hybridization conditions in a sodium concentration at about 19 mM at a temperature of about 65° C. are most preferred.

More specifically, a DNA containing the base sequence represented by SEQ ID NO:32, or the like is used as the DNA encoding the polypeptide containing the amino acid sequence represented by SEQ ID NO:4.

For the DNA encoding the partial peptide of the receptor of the present invention, any DNA can be used, so far as it contains a base sequence encoding the partial peptide of the receptor of the present invention described above. The DNA may be any of genomic DNA, genomic DNA library, cDNA derived from the cells/tissues described above, cDNA library derived from the cells/tissues described above, and synthetic DNA.

The DNA encoding the partial peptide of the receptor of the present invention includes, for example, a DNA having a partial base sequence of DNA containing the base sequence represented by SEQ ID NO:32, or a DNA having a base sequence hybridizable to the base sequence represented by SEQ ID NO:32 under high stringent conditions and having a partial base sequence of DNA encoding a polypeptide having an activity substantially equivalent to that of the receptor of the present invention, and the like.

The DNA that is hybridizable to the base sequence represented by SEQ ID NO:32 has the same significance as described above.

For the methods for hybridization and high stringent conditions, those described above are similarly used.

More specifically, examples of the DNA encoding the partial peptide of the receptor of the present invention are a DNA containing a DNA having a base sequence encoding a partial peptide containing 1 or more partial amino acid sequences selected from the partial amino acid sequences of 1 (Met)–123 (Phe), 301 (Asn)–358 (Lys), 548 (Tyr)–593 (Arg) and 843 (Ala)–895 (Ile) in the amino acid sequence represented by SEQ ID NO:4, or a DNA containing a DNA having a base sequence hybridizable to such a DNA under high stringent conditions; and the like.

The DNA encoding the polypeptide, receptor or partial peptide of the present invention may be labeled by publicly known methods. Specific examples include those labeled with an isotope, those labeled with fluorescence (labeling with, e.g., fluorescein, etc.), those biotinated, those labeled with enzyme, etc.

For cloning of the DNA that completely encodes the polypeptide, receptor or partial peptide of the present invention (hereinafter the polypeptides or the like are sometimes merely referred to as the polypeptide of the present invention in the following description of cloning and expression of the DNA encoding these polypeptides or the like), the DNA may be either amplified by publicly known PCR using synthetic DNA primers containing a part of the base sequence of the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989), etc. The hybridization may also be performed using commercially available library in accordance with the protocol described in the attached instructions.

Conversion of the base sequence of DNA can be made by publicly known methods such as the ODA-LA PCR method, the Gapped duplex method or the Kunkel method, or modifications thereof, by using a publicly known kit available as MUTAN™-super Express Km, a kit for site-directed mutagenesis using the ODA (Oligonucleotide-directed Dual Amber) method (manufactured by Takara Shuzo Co., Ltd., trademark), MUTAN™-K, a kit for site-directed mutagenesis using the Kunkel method (manufactured by Takara Shuzo Co., Ltd., trademark), etc.

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1–11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV•LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, λPL promoter, lpp promoter, T7 promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as Neo, G418 resistance), etc. In particular, when dhfr gene is employed as the selection marker using dhfr gene-deficient Chinese hamster cells, selection can also be made on thymidine free media.

If necessary, a signal sequence that matches with a host is added to the N-terminus of the polypeptide of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the polypeptide of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207–21 [Journal of Biochemistry, 95, 87 (1984)], etc.

Examples of yeast include *Saccharomyces cereviseae* AH22, $AH22R^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, HIGH FIVE™ (BTI-Tn-5B1-4) cell derived from egg of *Trichoplusia ni*, cells derived from *Mamestra. brassicae*, cells derived from *Estigmena acrea*, etc.; and for the virus BmNPV, *Bombyx mori* N cell (BmN cell), etc. is used. Examples of the Sf cell which can be used me Sf9 cell (ATCC CRL1711), Sf21 cell (both cells are described in Vaughn, J. L. et at, In Vivo, 13, 213–217 (1977)), etc.

As the insect, for example, a larva of *Bombyx mori*, etc. can be used [Maeda et al., Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as $CHO(dhfr^-)$ cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55 (1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263–267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary and desired, a chemical such as 3β-indolylacrylic acid can be added to the medium thereby to activate the promoter efficiently.

Where the bacteria belonging to the genus *Escherichia* are used as the host, the transformant is usually cultivated at approximately 15 to 43° C. for approximately 3 to 24 hours. If necessary, the culture may be aerated or agitated.

Where the bacteria belonging to the genus *Bacillus* are used as the host, the transformant is cultivated generally at approximately 30 to 40° C. for approximately 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505

(1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at approximately 20 to 35° C. for approximately 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the polypeptide of the present invention can be produced in the inside, cell membrane or outside of the transformant, etc.

The polypeptide of the present invention can be separated and purified from the culture described above, e.g., by the following procedures.

When the polypeptide of the present invention is extracted from the culture or cells, after cultivation the transformant or cell is collected by a publicly known method and suspended in an appropriate buffer. The transformant or cell is then disrupted by publicly known methods such as ultrasonication, a treatment with lysozyme and/or freeze-thaw cycling, followed by centrifugation, filtration etc. Thus, the crude extract of the polypeptide of the present invention can be obtained. The buffer used for the procedures may contain a protein modifier such as urea or guanidine hypochloride, or a surfactant such as TRITON X-100™ (polyoxylene (10) Octylphenyl Ether), etc. When the polypeptide of the present invention is secreted in the culture broth, alter completion of the cultivation the supernatant can be separated from the transformant or cell to collect the supernatant by a publicly known method.

The supernatant or the polypeptide of the present invention contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reversed phase high performance liquid chromatography, etc.; a method utilizing difference in isoelectric point such as isoelectrofocusing electrophoresis; and the like.

When the polypeptide of the present invention thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide of the present invention produced by the recombinant can be treated, prior to or after the purification, with an appropriate protein modifying enzyme so that the protein or partial peptide can be appropriately modified to partially remove a polypeptide. Examples of the protein-modifying enzyme include trypsin, chymotrypsin, arginyl endopeptidase, protein kinase, glycosidase and the like.

Antibodies to the polypeptide of the present invention (hereinafter sometimes simply referred to as the antibody (ies) of the present invention) may be any of polyclonal antibodies and monoclonal antibodies, as long as they are capable of recognizing antibodies to the polypeptide of the present invention, or esters or amides, or salts thereof.

The antibodies to the polypeptide of the present invention may be manufactured by publicly known methods for manufacturing antibodies or antisera, using as antigens the polypeptide of the present invention.

[Production of Monoclonal Antibody]

(a) Production of Monoclonal Antibody-producing Cells

The polypeptide of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495 (1975)]. Examples of the fusion promoter are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate)

adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like can be used for the selection and growth medium. The cultivation is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above. (b) Purification of Monoclonal Antibody Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Production of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and a warm-blooded animal is immunized with the complex in a manner similar to the method described above for the manufacture of monoclonal antibodies. The product containing the antibody to the polypeptide of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin, hemocyanin or the like is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once approximately every 2 to 6 weeks and approximately 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense DNAs (hereinafter these DNAs are sometimes merely referred to as the antisense DNA) having a complementary or substantially complementary base sequence to the DNA encoding the polypeptide, receptor or its partial peptide of the present invention (hereinafter these DNAs are sometimes merely referred to as the DNA of the present invention) can be any antisense DNA, so long as they possess a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the polypeptide of the present invention (e.g., the base sequence around the initiation codon). These antisense DNAs can be synthesized using a publicly known DNA synthesizer, etc.

Hereinafter there are explained the utilities of (1) the polypeptide of the present invention, (2) the DNA of the present invention, (3) the antibody of the present invention, and (4) the antisense DNA.

(1) Therapeutic/Preventive Agent for Diseases with Which the Polypeptide of the Present Invention is Associated As shown in EXAMPLES 5 though 8, 20 through 23, 64, etc., which will be described hereinafter, the polypeptide of the present invention has the cell stimulating activity (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, $GTP\gamma S$ binding activity, etc.) on GPR8 (the receptor of the present invention)-expressed cells, and is an endogenous ligand to GPR8 (the receptor of the present invention).

Therefore, when the polypeptide of the present invention of the DNA of the present invention involves any abnormality or deficiency, or when the receptor of the present invention or the DNA encoding the receptor involves any abnormality or deficiency, it is highly likely to cause various diseases, including anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder [e.g., prolactin secretion disorder (e.g., hypoovarianism, spermatic underdevelopment, menopausal symptoms, hypothyroidism, etc.)], pollakiuria, uremia, neurodegenerative disease (especially anorexia, etc.), or the like.

Therefore, the polypeptide of the present invention and the DNA of the present invention can be used as pharmaceuticals (in particular, appetite (eating) stimulants, etc.) for the treatment/prevention of various diseases as described above (especially anorexia).

When a patient has a reduced level of, or deficient in the polypeptide of the present invention in his or her body, the polypeptide of the present invention and the DNA of the present invention can provide the role of the polypeptide of the present invention sufficiently or properly for the patient, (a) by administering the DNA of the present invention to the patient to express the polypeptide of the present invention in the body, (b) by inserting the DNA of the present invention into a cell, expressing the polypeptide of the present invention and then transplanting the cell to the patient, or (c) by administering the polypeptide of the present invention to the patient, or the like.

When the DNA of the present invention is used as the preventive/therapeutic agents described above, the DNA is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as naked DNA, or with adjuvants to assist its uptake by gene gun or through a catheter such as a catheter with a hydrogel.

Where the polypeptide of the present invention is used as the aforesaid therapeutic/preventive agents, the polypeptide is advantageously used on a purity level of at least 90%, preferably at least 95%, more preferably at least 98% and most preferably at least 99%.

The polypeptide of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline end an isotonic solution containing glucose and other auxiliary agents (e.g., D-sorbitol, D-mannitol, sodium chloride, etc.) and may be used in combination with an appropriate dissolution aid such as an alchohol (e.g., ethanol or the like), a polyalcohol (e.g. propylene glycol and polyethylene glycol), a nonionic surfactant (e.g. POLYSORBATE 80™ (Polyoxyethylene(20) Sorbitan Monooleate) and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, chicken, sheep, swine, bovine, horse, cat, dog, monkey, etc.).

The dose of the polypeptide of the present invention varies depending on target disease, subject to be administered, route for administration, etc.; for example, in oral administration for the treatment of anorexia, the dose is normally about 0.1 mg to about 100 mg, preferably about 1.0 to about 50 mg, and more preferably about 1.0 to about 20 mg per day for adult (as 60 kg body weight). In parenteral administration, the single dose varies depending on subject to be administered, target disease, etc. but it is advantageous for the treatment of anorexia to administer the active ingredient intravenously at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(2) Screening of Drug Candidate Compounds for Disease

Since the polypeptide of the present invention has the function to act as the ligand to GPR8, the compounds or salts thereof that promote the function of the polypeptide of the present invention can be used as drugs for the treatment/prevention of diseases such as anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, Helicobacter pylori bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder [e.g., prolactin secretion disorder (e.g., hypoovarianism, spermatic underdevelopment, menopausal symptoms, hypothyroidism, etc.)], pollakiuria, uremia, neurodegenerative disease (especially anorexia, etc.), or the like.

On the other hand, the compounds or salts thereof that inhibit the function of the polypeptide of the present invention are useful as safe and low-toxic drugs for the treatment/prevention of, e.g., obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.; as safe and low-toxic drugs for the treatment/prevention (prolactin production suppressing agents) of pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma or Sheehan's syndrome, spermatogenesis disorder, etc., especially, obesity, hyperphagia, etc.

By using the polypeptide of the present invention, or by constructing the expression system of recombinant polypeptide of the present invention and using the receptor-binding assay system via the expression system, screening can be performed efficiently on the compound or salts thereof that alter the binding property between the polypeptide of the present invention and the receptor (e.g., peptide, protein, a non-peptide compound, a synthetic compound, fermentation product, etc.). Such compounds include compounds (i.e., the receptor agonist of the polypeptide of the present invention) that have the cell-stimulating activity (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.) mediated by the receptors to the polypeptide of the present invention; compounds that do not have the cell-stimulating activity (i.e., the receptor antagonist of the polypeptide of the present invention); and the like. The term "alters the binding property to the ligand" is used to include both cases where binding to the ligand is inhibited and binding to the ligand is promoted.

Thus, the present invention provides a method of screening a compound or its salt that promotes or inhibits the activity of the polypeptide of the present invention, which comprises using the polypeptide of the present invention, more specifically, a method of screening a compound that alters the binding property between the polypeptide of the present invention and the receptor of the present invention (a compound that promotes or inhibits the activity of the polypeptide of the present invention) or its salt, which comprises comparing (i) the case wherein the polypeptide of the present invention is brought in contact with the receptor of the present invention or its partial peptide (hereinafter they are sometimes merely referred to as the receptor of the present invention) and (ii) the case wherein the polypeptide of the present invention and a test compound are brought in contact with the receptor of the present invention.

According to the screening method of the present invention, the method comprises assaying, for example, the binding amount of the ligand to the receptor of the present invention, the cell-stimulating activity, or the like, (i) when the polypeptide of the present invention is brought in contact with the receptor of the present invention described above and (ii) when the polypeptide of the present invention and a test compound are brought in contact with the receptor of the present invention described above, and comparing (i) and (ii).

Specifically, the screening method of the present invention includes:

(1) a method of screening a compound that alters the binding property between the polypeptide of the present invention and the receptor of the present invention (a compound that promotes or inhibits the activity of the polypeptide of the present invention) or its salt, which comprises assaying the binding amount of a labeled form of the polypeptide of the present invention to the receptor of the present invention, (i) in the case wherein a labeled form of the polypeptide of the present invention is brought in contact with the receptor of the present invention above and (ii) in the case wherein a labeled form of the polypeptide of the present invention and a test compound are brought in contact with the receptor of the present invention, and comparing (i) and (ii);

(2) a method of screening a compound that alters the binding property between the polypeptide of the present invention and the receptor of the present invention (a compound that promotes or inhibits the activity of the polypeptide of the present invention) or its salt, which comprises assaying the binding amount of a labeled form of the polypeptide of the present invention to a cell containing the receptor of the present invention or its cell membrane, (i) in the case wherein a labeled form of the polypeptide of the present invention is brought in contact with the cell containing the receptor of the present invention or its cell membrane and (ii) in the case wherein a labeled form of the polypeptide of the present invention and a test compound are brought in contact with the cell containing the receptor of the present invention or its cell membrane, and comparing (i) and (ii);

(3) a method of screening a compound that alters the binding property between the polypeptide of the present invention and the receptor of the present invention (a compound that promotes or inhibits the activity of the polypeptide of the present invention) or its salt, which comprises assaying the binding amount of a labeled form of the polypeptide of the present invention to the receptor of the present invention, (i) in the case wherein a labeled form of the polypeptide of the present invention is brought in contact with the receptor of the present invention expressed on a cell membrane by culturing a transformant containing a DNA encoding the receptor of the present invention and (ii) in the case wherein a labeled form of the polypeptide of the present invention and a test compound are brought in contact with the receptor of the present invention expressed on a cell membrane by culturing a transformant containing a DNA encoding the receptor of the present invention, and comparing (i) and (ii);

(4) a method of screening a compound that alters the binding property between the polypeptide of the present invention and the receptor of the present invention (a compound that promotes or inhibits the activity of the polypeptide of the present invention) or its salt, which comprises assaying the cell-stimulating activity mediated by the receptor of the present invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.), when a compound that activates the receptor of the present invention (e.g., the polypeptide of the present invention) is brought in contact with a cell containing the receptor of the present invention and when the compound that activates the receptor of the present invention and a test compound are brought in contact with a cell containing the receptor of the present invention, and comparing the activity; and, (5) a method of screening a compound that alters the binding property between the polypeptide of the present invention and the receptor of the present invention (a compound that promotes or inhibits the activity of the polypeptide of the present invention) or its salt, which comprises assaying the cell-stimulating activity mediated by the receptor of the present invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.), when a compound that activates the receptor of the present invention (e.g., the polypeptide of the present invention, etc.) is brought in contact with the receptor of the present invention expressed on a cell membrane by culturing a transformant containing a DNA encoding the receptor of the present invention and when the compound that activates the receptor of the present invention and a test compound are brought in contact with the receptor of the present invention expressed on a cell membrane by culturing a transformant containing a DNA encoding the receptor of the present invention, and comparing the activity; etc.

The screening method of the present invention will be described below more specifically.

First, the receptor of the present invention, which is used for the screening method of the present invention, may be any protein, so long as it recognizes the polypeptide of the present invention as a ligand, and membrane fractions from human or other warm-blooded animal organs are preferably employed. However, it is very difficult to obtain human-derived organs especially, and the receptor of the present invention, etc. expressed abundantly by use of recombinants are suitable for use in the screening.

In the manufacture of the receptor of the present invention, the methods of manufacturing the polypeptide of the present invention, etc. described above may be used.

Where the cell containing the receptor of the present invention or its cell membrane fraction is used in the screening method of the present invention, the procedures later described apply to the method.

When the cell containing the receptor of the present invention is used in the screening method of the present invention, the cell may be fixed with glutaraldehyde, formalin, etc. The fixation may be carried out by a publicly known method.

The cell containing the receptor of the present invention refers to a host cell expressing the receptor of the present invention. Examples of such a host cell include *Escherichia coli, Bacillus subtilis*, yeast, insect cells, animal cells, etc. Host cells in which the receptor of the present invention is expressed may be prepared in a manner similar to the above-stated method for manufacturing transformants transformed by expression vectors containing the polypeptide of the present invention.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or POLYTRON (manufactured by Kinematica Inc.), disruption by ultrasonication, disruption by cell spraying via a thin nozzle under increasing pressure using a French press, etc. and the like. Cell membranes are fractionated mainly by fractionation using a centrifugal force such as for example fractionation centrifugation, density gradient centrifugation, etc. For example, cell disruption fluid is centrifuged at low rate (500 rpm to 3,000 rpm) for a short period of time (normally about 1 minute to 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in the receptor expressed and membrane components such as cell-derived phospholipids, membrane proteins and the like.

The amount of the receptor of the present invention contained in the cells containing the receptor of the present invention or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) for screening the compound that alters the binding property between the polypeptide of the present invention and the receptor of the present invention (the compound that promotes or inhibits the activity of the polypeptide of the present invention), an appropriate fraction of the receptor of the present invention and a labeled form of the polypeptide of the present invention, etc. are required. The fraction of the receptor of the present invention is preferably a fraction of a naturally occurring form of the receptor of the present invention or a fraction of a recombinant type of the receptor of the present invention having an equivalent activity. Herein, the term equivalent activity is intended to mean a ligand binding activity, etc. that is equivalent to the activity possessed by naturally occurring receptors. As the labeled ligand, there may be used a labeled ligand, a labeled ligand analog compound, etc. For example, there may be used ligands that are labeled with $[^3H]$, $[^{125}I]$, $[^{14}C]$, $[^{35}S]$, etc. Of these, $[^{125}I]$-labeled ligand is preferred.

More specifically, the compound that alters the binding property between the polypeptide of the present invention and the receptor of the present invention is screened by the following procedures. First, a receptor preparation is prepared by suspending cells containing the receptor of the present invention or the membrane fraction thereof in a buffer appropriate for use in the screening method. Any buffer can be used so long as it does not interfere with the ligand-receptor binding, including a phosphate buffer or a Tris-HCl buffer, having pH of 4 to 10 (preferably pH of 6 to 8), etc. For the purpose of minimizing non-specific binding, a surfactant such as CHAPS, TWEEN-80™ (Polyoxyethylene (20) Sorbitain Monooleate) (Kao-Atlas Inc.), digitonin, deoxycholate, etc., may optionally be added to the buffer. Further for the purpose of suppressing the degredation of the receptor of the present invention or the polypeptide of the present invention with a protease, a protease inhibitor such as PMSF, leupeptin, E-64 (manufactured by Peptide Institute, Inc.), pepstatin etc. may also be added. A given amount (5,000 cpm to 500,000 cpm) of the labeled polypeptide of the present invention is added to 0.01 ml to 10 ml of the receptor solution, in which $10^{-10}M$ to $10^{-7}M$ of a test compound is co-present. To determine the amount of non-specific binding (NSB), a reaction tube charged with an unlabeled form of the polypeptide of the present invention in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound.

The method (4) or (5) above for screening the compound that alters the binding property between the polypeptide of the present invention and the receptor of the present invention (the compound that promotes or inhibits the activity of the polypeptide of the present invention) can be performed as follows. For example, the cell stimulating activity mediated by the receptor of the present invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.) may be determined by a publicly known method, or using an assay kit commercially available. Specifically, the cells containing the receptor of the present invention are first cultured on a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to a degrading enzyme contained in the cells, an inhibitor against such as a degrading enzyme may be added prior to the assay. For detecting the activity such as the cAMP production suppression, the baseline production in the cells is increased by forskolin or the like and the suppressing effect on the increased baseline production can be detected.

For screening through the assay of the cell stimulating activity, appropriate cells, in which the receptor of the present invention is expressed, are required. Preferred cells, in which the receptor of the present invention is expressed, are the aforesaid cell line in which the receptor of the present invention is expressed, etc.

Examples of the test compounds include peptides, proteins, non-peptide compounds, synthetic compounds, fermentation products, cell extracts, plant extracts, animal tissue extracts, etc.

A kit for screening the compound or a salt thereof that alters the binding property between the polypeptide of the present invention (the compound that promotes or inhibits the activity of the polypeptide of the present invention) and the receptor of the present invention comprises the receptor of the present invention or its salt, a partial peptide of the receptor of the present invention or its salt, cells containing the receptor of the present invention or a membrane fraction of the cells containing the receptor of the present invention, and the polypeptide of the present invention.

Examples of the screening kit of the present invention are given below:

1. Reagent for Screening (1) Assay Buffer and Wash Buffer

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Preparation of the Receptor of the Present Invention

CHO cells on which the receptor of the present invention has been expressed are subcultured in a 12-well plate at the rate of $5 \times 10^5$ cells/well and then cultured at 37° C. under 5% $CO_2$ and 95% air for 2 days.

(3) Labeled Ligand

The polypeptide of the present invention labeled with commercially available [$^3$H], [$^{125}$I], [$^{14}$C], [$^{35}$S], etc. is dissolved in a suitable solvent or buffer. The solution is stored at 4° C. or −20° C., which is diluted to 1 μM with an assay buffer at use.

(4) Standard Ligand Solution

The polypeptide of the present invention is dissolved in PBS supplemented with 0.1% bovine serum albumin (manufactured by Sigma, Inc.) in a concentration of 1 mM, and the solution is stored at −20° C.

2. Assay Method (1) Cells are cultured in a 12-well tissue culture plate to express the receptor of the present invention. After washing the cells twice with 1 ml of the assay buffer, 490 μl of the assay buffer is added to each well.

(2) After 5 μl of a test compound solution of $10^{-3}$ to $10^{-10}$ M is added, 5 μl of a labeled form of the peptide of the present invention is added to the system followed by reacting at room temperature for an hour. To determine the amount of the non-specific binding, the polypeptide of the present invention of $10^{-3}$ M is added in an amount of 5 μl, instead of the test compound.

(3) The reaction mixture is removed and washed 3 times with 1 ml each of the wash buffer. The labeled polypeptide of the present invention bound to the cells is dissolved in 0.2N NaOH-1% SDS and mixed with 4 ml of a liquid scintillator A (manufactured by Wako Pure Chemical Industries, Ltd.).

(4) Radioactivity is measured using a liquid scintillation counter (manufactured by Beckmann) and PMB (percent of the maximum binding) is calculated in accordance with the following equation 1:

$$PMB = [(B - NSB)/(B_0 - NSB)] \times 100$$

wherein:
PMB: percent of the maximum binding
B: value when a sample is added
NSB: non-specific binding
$B_0$: maximum binding The compound or its salt obtainable by the screening method or the screening kit of the present invention is the compound that alters the binding property between the polypeptide of the present invention and the receptor of the present invention (the compound that promotes or inhibits the activity of the polypeptide of the present invention). Specifically, these compounds are compounds or salts thereof that exhibit the cell stimulating activity mediated by the receptor of the present invention (so-called the receptor agonist of the present invention), or compounds that do not exhibit the cell stimulating activity (so-called the receptor antagonist of the present invention). Examples of such compounds include peptides, proteins, non-peptide compounds, synthetic compounds and fermentation products. These compounds may be either novel or publicly known compounds.

In order to evaluate whether the compound is the receptor agonist or antagonist of the present invention described above, it is determined by (i) or (ii) below.

(i) According to the screening methods (1) to (3), binding assay is carried out to obtain the compound that alters the binding property between the polypeptide of the present invention and the receptor of the present invention (especially, the compound that inhibits the binding). It is then determined if the compound has the above cell-stimulating activity mediated by the receptor of the present invention. The compound having the cell-stimulating activity or its salt is the receptor agonist of the present invention, whereas the compound having no such an activity or its salt is the receptor antagonist of the present invention.

(ii) (a) A test compound is brought in contact with a cell containing the receptor of the present invention, whereby the aforesaid cell-stimulating activity mediated by the receptor of the present invention is assayed. The compound having the cell-stimulating activity or its salt is the receptor agonist of the present invention.

(b) The cell-stimulating activity mediated by the receptor of the present invention is assayed in the case where a compound that activates the receptor of the present invention (e.g., the polypeptide of the present invention or the receptor agonist of the present invention, etc.) is brought in contact with cells containing the receptor of the present invention and in the case where the compound that activates the receptor of the present invention and a test compound are brought in contact with cells containing the receptor of the present invention, and compared therebetween. The compound or its salt that can reduce the cell-stimulating activity induced by the compound that activates the receptor of the present invention is the receptor antagonist of the present invention.

The receptor agonists of the present invention exhibit similar physiological activity of the polypeptide of the present invention on the receptor of the present invention, and are thus safe and low-toxic drugs (e.g., preventive/therapeutic drugs for anorexia, appetite (eating) stimulants, preventive/therapeutic drugs for pituitary hormone secretion disorders [e.g., prolactin secretion disorder (e.g., hypoovarianism, spermatic underdevelopment, menopausal symptoms, hypothyroidism, etc.)].

In contrast, the receptor antagonist of the present invention can suppress the physiological activity that the polypeptide of the present invention has on the receptor of the present invention, and are thus useful as safe and low-toxic drugs for the treatment/prevention of, e.g., obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.; as safe and low-toxic drugs for the treatment/prevention (prolactin production suppressing agents) of pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma or Sheehan's syndrome, spermatogenesis disorder, etc.; preferably as safe and low-toxic preventive/therapeutic agents for obesity, hyperphagia, etc.

The compound or its salt, which is obtainable using the screening method or the screening kit of the present invention, is selected from, e.g., peptides, proteins, non-peptide compounds, synthetic compounds, fermentation products, cell extracts, plant extracts, animal tissue extracts, plasma, etc., and is the compound that promotes or inhibits the function of the polypeptide of the present invention.

As salts of the compound, there may be used those similar to the salts of the polypeptide of the present invention described above.

When the compound obtained by the screening method or screening kit of the present invention is used as the prophylactic/therapeutic agent described above, the compound can be prepared into pharmaceutical preparations in a conventional manner. For example, the compound may be prepared in the form of tablets, capsules, elixir, microcapsule, a sterile solution, a suspension, etc., as in the aforesaid drugs containing the polypeptide of the present invention.

Since the thus obtained pharmaceutical preparation is safe and low toxic, the preparation may be administered to human or other warm-blooded animal (e.g., mouse, rat, rabbit, sheep, swine, bovine, horse, chicken, cat, dog, monkey, chimpanzee, etc.).

The dose of the compound or its salt varies depending on its activity, target disease, subject to be administered, route for administration, etc.; for example, where the compound that promotes the function of the polypeptide of the present invention is orally administered for the treatment of anorexia, the dose is normally about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. When the compound that promotes the function of the polypeptide of the present invention is administered to adult (as 60 kg body weight) in the form of injection for the treatment of anorexia, it is advantageous to administer intravenously to adult the compound generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

Also, when the compound that inhibits the function of the polypeptide of the present invention is orally administered to adult (per 60 kg body weight) for the treatment of obesity, a daily dose to be administered is generally approximately 0.1 to 100 mg, preferably approximately 1.0 to 50 mg, and more preferably approximately 1.0 to 20 mg. In parenteral administration, a single dose of the compound varies depending on subject to be administered, target disease, etc. For example, when the compound that inhibits the function of the polypeptide of the present invention is administered to adult (as 60 kg body weight) in the form of injection for the treatment of obesity, it is advantageous to administer intravenously to adult (per 60 kg body weight) the compound generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

(3) Quantification of the Polypeptide of the Present Invention

The antibody to the polypeptide of the present invention (hereinafter sometimes simply referred to as the antibody (ies) of the present invention) is capable of specifically recognizing the polypeptide of the present invention, and can thus be used for quantification of the polypeptide of the present invention in a sample fluid, in particular, for quantification by sandwich immunoassay.

That is, the present invention provides:

(i) a method for quantification of the polypeptide of the present invention in a sample fluid, which comprises competitively reacting the antibody of the present invention with a sample fluid and a labeled form of the polypeptide of the present invention, and measuring the ratio of the labeled polypeptide of the present invention bound to said antibody; and, (ii) a method for quantification of the polypeptide of the present invention in a sample fluid, which comprises simultaneously or continuously reacting the sample fluid with the antibody of the present invention and a labeled form of another antibody of the present invention immobilized on an insoluble carrier, and measuring the activity of the labeling agent on the immobilized carrier.

In the method (ii) described above, it is preferred that one antibody is capable of recognizing the N-terminal region of the polypeptide of the present invention, while another antibody is capable of recognizing the C-terminal region of the polypeptide of the present invention.

The monoclonal antibody to the polypeptide of the present invention may be used to quantify the polypeptide of the present invention. Moreover, the polypeptide of the present invention may also be detected by means of a tissue staining, etc. For these purposes, the antibody molecule per se may be used, or $F(ab')_2$, Fab' or Fab fractions of the antibody molecule may be used as well.

The method of quantifying the polypeptide of the present invention using the antibody of the present invention is not particularly limited, and any method may be used so far as it relates to a method, in which the amount of an antibody, antigen or antibody-antigen complex can be detected by a chemical or a physical means, depending on or corresponding to the amount of antigen (e.g., the amount of polypeptide) in a sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same, are radioisotopes, enzymes, fluorescent substances, luminescent substances, etc. Examples of radioisotopes are [$^{125}$I], [$^{131}$I], [$^{3}$H], [$^{14}$C], etc. Preferred examples of enzymes are those that are stable and have a high specific activity, which include β-galactosidase, β-glucosidase, alkaline phosphatase, peroxidase, malate dehydrogenase, etc. Examples of fluorescent substances are fluorescamine, fluorescein isothiocyanate, etc. Examples of luminescent substances are luminol, a luminol derivative, luciferin, lucigenin, etc. Furthermore, a biotin-avidin system may be used as well for binding an antibody or antigen to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, a sample fluid is reacted with an immobilized form of the monoclonal antibody of the present invention (primary reaction), then reacted with a labeled form of the monoclonal antibody of the present invention (secondary reaction) and the activity of the labeling agent on the insoluble carrier is assayed; thus, the amount of polypeptide of the present invention in a sample fluid can be determined. The primary and secondary reactions may be carried out in a reversed order, simultaneously or sequentially with intervals. The type of the labeling agent and the method of immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the assay sensitivity, etc.

In the method of assaying the polypeptide of the present invention by the sandwich method according to the present invention, preferred monoclonal antibodies of the present invention used for the primary and the secondary reactions are antibodies, which binding sites to the polypeptide of the present invention are different from each other. Thus, the antibodies used in the primary and secondary reactions are those wherein, when the antibody used in the secondary reaction recognizes the C-terminal region of the polypeptide of the present invention, the antibody recognizing the site other than the C-terminal regions, e.g., recognizing the N-terminal region, is preferably used in the primary reaction.

The monoclonal antibody of the present invention may be used in an assay system other than the sandwich method, such as the competitive method, the immunometric method or the nephrometry.

In the competitive method, an antigen in a sample fluid and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the sample fluid. In the reactions for such a method, there are a liquid phase method in which a soluble antibody is used as the antibody and the B/F separation is effected by polyethylene glycol, while a second antibody to the antibody is used, and a solid phase method in which an immobilized antibody is used as the first antibody or a soluble antibody is used as the first antibody, while an immobilized antibody is used as the second antibody.

In the immunometric method, an antigen in a sample fluid and an immobilized antigen are competitively reacted with a given amount of a labeled antibody followed by separating the solid phase from the liquid phase; or an antigen in a sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the sample fluid.

In the nephrometry, the amount of insoluble sediment, which is produced as a result of the antigen-antibody reaction in a gel or in a solution, is measured. Even when the amount of an antigen in a sample fluid is small and only a small amount of the sediment is obtained, a laser nephrometry utilizing laser scattering can be suitably used.

In applying each of those immunoassays to the assay method of the present invention, any special conditions, operations, etc. are not required. The assay system for the polypeptide of the present invention may be constructed in addition to conditions or operations conventionally used for each of the methods, taking technical consideration by one skilled in the art into account. For the details of such conventional technical means, a variety of reviews, reference books, etc. may be referred to:

for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.

As described above, the polypeptide of the present invention can be quantified with high sensitivity, using the antibody of the present invention.

Furthermore when a reduced level of the polypeptide of the present invention is detected by quantifying a level of the polypeptide of the present invention using the antibody of the present invention, it can be diagnosed that one suffers from, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicella-zoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder [e.g., prolactin secretion disorder (e.g., hypoovarianism, spermatic underdevelopment, menopausal symptoms, hypothyroidism, etc.)], pollakiuria, uremia, neurodegenerative disease (especially, anorexia or the like) etc.; or it is highly likely for one to suffer from these disease in the future.

When an increased level of the polypeptide of the present invention is detected, it can be diagnosed that one suffers from, e.g., obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma, Sheehan's syndrome, spermatogenesis disorder (especially, obesity or the like), etc.; or it is highly likely for one to suffer from these disease in the future.

The antibody to the polypeptide of the present invention may also be employed to detect the polypeptide of the present invention present in a sample fluid such as body fluids, tissues, etc. The antibody may further be used for the preparation of an antibody column used to purify the polypeptide of the present invention, detect the polypeptide of the present invention in each fraction upon purification, analysis of the behavior of the polypeptide of the present invention in the cells under investigation.

(4) Gene Diagnostic Agent

By using the DNA of the present invention, e.g., as a probe, abnormality (gene abnormality) of the DNA or mRNA encoding the polypeptide of the present invention in human or other warm-blooded animal (e.g., rat, mouse, guinea pig, rabbit, chicken, sheep, swine, bovine, horse, cat, dog, monkey, etc.) can be detected. Thus, the DNA of the present invention is useful as a gene diagnostic agent for the damage to the DNA or mRNA, mutation, a decreased expression or an increased expression, or overexpression of the DNA or mRNA.

The gene diagnosis described above using the DNA of the present invention can be performed by, for example, the publicly known Northern hybridization assay or the PCR-SSCP assay (Genomics, 5, 874–879 (1989); Proceedings of the National Academy of Sciences of the United States of America, 86, 2766–2770 (1989)).

When a decreased expression is detected, e.g., by the Northern hybridization, it can be diagnosed that one is likely to suffer from, for example, anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder [e.g., prolactin secretion disorder (e.g., hypoovarianism, spermatic underdevelopment, menopausal symptoms, hypothyroidism, etc.)], pollakiuria, uremia, neurodegenerative disease (especially anorexia or the like) etc.; or it is highly likely for one to suffer from diseases in the future.

When overexpression is detected by the Northern hybridization, it can be diagnosed that one is likely to suffer from, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.; as safe and low-toxic drugs for the treatment/prevention (prolactin production suppressing agents) of pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma or Sheehan's syndrome, spermatogenesis disorder, etc. (especially, obesity or the like); or it is highly likely for one to suffer from diseases in the future.

(5) Pharmaceutical Composition Comprising Antisense DNA

Antisense DNA that binds complementarily to the DNA of the present invention to inhibit expression of the DNA can be used as preventive/therapeutic agents for diseases, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.; as safe and low-toxic drugs for the treatment/prevention (prolactin production suppressing agents) of pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma or Sheehan's syndrome, spermatogenesis disorder, etc. (especially, obesity or the like), etc.

When the antisense DNA is used, the antisense DNA may be administered directly, or the DNA is inserted into an appropriate vector such as retrovirus vector, adenovirus vector, adenovirus-associated virus vector, etc. and then administered in a conventional manner. The antisense DNA may also be administered as intact DNA, or with adjuvants to assist its uptake by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

(6) Pharmaceutical Composition Comprising the Antibody of the Present Invention

The antibody of the present invention having the effect to neutralize the polypeptide of the present invention can be used as drugs for the prevention/treatment of diseases, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.; as safe and low-toxic drugs for the treatment/prevention (prolactin production suppressing agents) of pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma or Sheehan's syndrome, spermatogenesis disorder, etc. (especially, obesity or the like), etc.

The therapeutic/preventive agents for diseases described above comprising the antibody of the present invention can be administered to human or other warm-blooded animal (e.g., rat, rabbit, sheep, swine, bovine, cat, dog, monkey, etc.) orally or parenterally directly as a liquid preparation, or as a pharmaceutical composition in an appropriate preparation form. The dose varies depending on subject to be administered, target disease, conditions, route for administration, etc.; when it is used for the treatment/prevention of the adult patient with, e.g., obesity, the agent is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), nonionic surfactant [e.g., polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(7) DNA Transgenic Animal

The present invention provides a non-human mammal bearing an exogenous DNA encoding the polypeptide of the present invention (hereinafter merely referred to as the exogenous DNA of the present invention) or its variant DNA (sometimes simply referred to as the exogenous variant DNA of the present invention).

Thus, the present invention provides:

(1) a non-human mammal bearing the exogenous DNA or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57BL/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of creating model animals for human disease.

"Mammals" in a recombinant vector that can be expressed in the mammals include the aforesaid non-human mammals and human.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the abnormal polypeptide of the present invention and exemplified by the DNA that expresses a polypeptide to suppress the functions of the normal polypeptide of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters, which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for the DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among others them, cytomegalovirus promoters, human polypeptide elongation factor 1α (EF-1α) promoters, human and chicken β actin promoters etc., which protein can highly express in the whole body are preferred.

It is preferred that the vectors described above have a sequence for terminating the transcription of the desired messenger RNA in the DNA transgenic animal (generally called a terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal polypeptide of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. Also, an exogenous abnormal DNA can produce a translational region, which is obtained by point mutagenesis variation of the translational region for a normal polypeptide obtained from the cells or tissues described above.

The said translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the exogenous DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the polypeptide of the present invention by promoting the function of endogenous normal DNA. Therefore, the animal can be utilized as a pathologic model animal for such a disease. Specifically, using the normal DNA transgenic animal of the present invention, it is possible to elucidate the mechanism of the hyperfunction of the polypeptide of the present invention and the pathological mechanism of the disease associated with the polypeptide of the present invention and to determine how to treat the disease.

Furthermore, since a mammal transfected the exogenous normal DNA of the present invention exhibits an increasing symptom of the polypeptide of the present invention librated, the animal is usable for screening therapeutic agents for the disease associated with the polypeptide of the present invention.

On the other hand, non-human mammal having the exogenous abnormal DNA of the present invention can be passaged under normal breeding conditions as the DNA-bearing animal by confirming the stable retaining of the exogenous DNA via crossing. Further, the exogenous DNA to be subjected can be utilized as a starting material by inserting the DNA into the plasmid described above. The DNA construct with promoter can be prepared by conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bled to have the DNA.

Since non-human mammal having the abnormal DNA of the present invention may express the abnormal DNA of the present invention at a high level, the animal may be the function inactivation type inadaptability of the polypeptide of the present invention by inhibiting the function of the endogenous normal DNA and can be utilized as its disease model animal. For example, using the abnormal DNA-transferred animal of the present invention, it is possible to elucidate the mechanism of inadaptability of the polypeptide of the present invention and to perform to study a method for treatment of this disease.

More specifically, the transgenic animal of the present invention expressing the abnormal DNA of the present invention to a high level is also expected to serve as an experimental model for the elucidation of the mechanism of the functional inhibition (dominant negative effect) of normal polypeptide by the abnormal polypeptide of the present invention in the function inactive type inadaptability of the polypeptide of the present invention.

A mammal bearing the abnormal exogenous DNA of the present invention is also expected to serve for screening a candidate drug for the treatment of the function inactive type inadaptability of the polypeptide of the present invention or the receptor protein of the present invention, since the polypeptide of the present invention or the receptor protein of the present invention is increased in such an animal in its free form.

Other potential applications of two kinds of the transgenic animals described above include:

(1) use as a cell source for tissue culture;

(2) elucidation of the relation to a polypeptide that is specifically expressed or activated by the polypeptide of the present invention, by direct analysis of DNA or RNA in tissue of the DNA transgenic animal of the present invention or by analysis of the polypeptide tissue expressed by the DNA;

(3) research in the function of cells derived from tissues that are cultured usually only with difficulty, using cells of tissue bearing the DNA cultured by a standard tissue culture technique;

(4) screening of a drug that enhances the functions of cells using the cells described in (3) above; and, (5) isolation and purification of the variant polypeptide of the present invention and preparation of an antibody thereto.

Furthermore, clinical conditions of a disease associated wit the polypeptide of the present invention, including the function inactive type inadaptability of the polypeptide of the polypeptide of the present invention can be determined using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the polypeptide of the present invention, and as studies on association with apoptosis, differentiation or propagation or on the mechanism of signal transduction in these properties to inspect any abnormality therein. Thus the DNA transgenic animal of the present invention can provide an effective research material for the polypeptide of the present invention and for elucidating the function and effect thereof.

To develop a therapeutic drug for the treatment of diseases associated with the polypeptide of the present invention, including the function inactive type inadaptability of the polypeptide of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human embryonic stem cell in which the DNA of the present invention is inactivated;

(2) an embryonic stem cell according to (1), wherein the DNA is inactivated by introducing a reporter gene (e.g., β-galactosidase gene derived from *Escherichia coli*);

(3) an embryonic stem cell according to (1), which is resistant to neomycin;

(4) an embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA of the present invention is inactivated;

(7) a non-human mammal according to (5), wherein the DNA is inactivated by inserting a reporter gene (e.g., β-galactosidase derived from *Escherichia coli*) therein and the reporter gene is capable of being expressed under control of a promoter for the DNA of the present invention;

(8) a non-human mammal according to (6), which is a rodent;

(9) a non-human mammal according to (8), wherein the rodent is mouse; and,

(10) a method for screening a compound or its salt that promotes or inhibits the promoter activity for the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide of the present invention (hereinafter sometimes referred to as the knockout DNA of the present invention) by substantially inactivating the activity of the polypeptide of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons, thus inhibiting the synthesis of complete messenger RNA to eventually destroy the gene (hereinafter simply referred to as targeting vector). The thus obtained ES cells are subjected to Southern hybridization analysis using a DNA sequence on or near the DNA of the present invention as a probe, or to PCR analysis using a DNA sequence on the targeting vector and another DNA sequence near the DNA of the present invention, which is not included in the targeting vector as primers, thereby to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1–10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention are useful for studying the polypeptide of the present invention or the receptor protein of the present invention from an aspect of cell biology.

The non-human mammal deficient in expression of the DNA of the present invention can be identified from a normal animal by measuring the mRNA amount in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The cells with the DNA of the present invention knockout can be identified by the Southern hybridization analysis using a DNA sequence on or near the DNA of the present invention as a probe, or by PCR analysis using as primers a DNA sequence on the targeting vector and another DNA sequence, which is not included in the targeting vector. When non-human mammalian embryonic stem cells are used, a cell line wherein the DNA of the present invention is inactivated by homologous recombination is cloned; the resulting cloned cell line is injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the polypeptide of the present invention. The individuals deficient in homozygous expression of the polypeptide of the present invention or the receptor protein of the present invention can be obtained from offspring of the intercross between the heterozygotes of the polypeptide of the present invention or the receptor protein of the present invention.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the polypeptide of the present invention or the receptor of the present invention, such an animal can be a disease model suspected of inactivated biological activities of the polypeptide of the present invention or the receptor of the present invention and thus, offers an effective study to investigate causes for and therapy for these diseases.

(8a) Method of Screening Compounds Having Therapeutic/Preventive Effects on Diseases Caused by Deficiency, Damages, etc. of the DNA of the Present Invention The non-human mammal deficient in expression of the DNA of the present invention can be employed for screening of compounds having therapeutic/prophylactic effects on diseases caused by deficiency, damages, etc. of the DNA of the present invention.

That is, the present invention provides a method for screening of a compound having therapeutic/prophylactic effects for diseases caused by deficiency, damages, etc. of the DNA of the present invention, which comprises administering a test compound to the non-human mammal deficient in expression of the DNA of the present invention and observing and measuring a change occurred in the animal.

As the non-human mammal deficient in expression of the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be test with a test compound, for example, oral administration, intravenous injection, etc. are applied and the treatment is appropriately selected depending upon conditions of the test animal, properties of the test compound, etc. Furthermore, a dose of n amount of test compound to be administered can be appropriately chosen depending on method for administration, nature of test compound, etc.

In screening compounds having the therapeutic/preventive effect on, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder [e.g., prolactin secretion disorder (e.g., hypoovarianism, spermatic underdevelopment, menopausal symptoms, hypothyroidism, etc.)], pollakiuria, uremia, neurodegenerative disease, etc. (especially, anorexia or the like), the non-human mammal deficient in expression of the DNA of the present invention is subjected to a sugar loading treatment, a test compound is administered before or after the sugar loading treatment and, blood sugar level, body weight change, etc. of the animal is measured with passage of time.

In the screening method described above, when a test compound is administered to a test animal and found to reduce the blood sugar level of the animal to at least about 10%, preferably at least about 30% and more preferably at least about 50%, the test compound can be selected to be a compound having a therapeutic and prophylactic effect for the diseases above.

The compound obtained using the screening method above is a compound selected from the test compounds described above and exhibits a therapeutic and prophylactic effect for the diseases caused by deficiencies, damages, etc. of the polypeptide of the present invention. Therefore, the compound can be employed as a safe and low toxic drug for the treatment and prevention of these diseases. Furthermore, compounds derived from such a compound obtained by the screening described above can be similarly employed.

The compound obtained by the screening method above may be in the form of salts. As such salts, there may be used salts with physiologically acceptable acids (e.g., inorganic acids, organic acids, etc.) or bases (e.g., alkali metal salts, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical composition comprising the compound obtained by the above screening method or salts thereof may be manufactured in a manner similar to the method for preparing the pharmaceutical composition comprising the polypeptide of the present invention described hereinabove.

Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

A dose of the compound or its salt to be administered varies depending upon particular disease, subject to be administered, route of administration, etc., and in oral administration to an adult patient with anorexia (as 60 kg body weight), the compound is administered generally in a dose of approximately 0.1 to 100 mg, preferably approximately 1.0 to 50 mg, more preferably approximately 1.0 to 20 mg per day. For parenteral administration to an adult patient with anorexia (as 60 kg body weight), it is advantageous to administer the compound intravenously in the form of an injectable preparation in a dose of approximately 0.01 to 30 mg, preferably approximately 0.1 to 20 mg, more preferably approximately 0.1 to 10 mg per day, though the single dosage varies depending upon particular subject, particular disease, etc. For other animals, the compound can be administered in the corresponding dose with converting it into that for the 60 kg body weight.

(8b) Method for Screening a Compound that Promotes or Inhibits the Activities of a Promoter to the DNA of the Present Invention The present invention provides a method of screening a compound or its salt that promotes or inhibits the activity of a promoter to the DNA of the present invention or salts thereof, which comprises administering a test compound to a non-human mammal deficient in expression of the DNA of the present invention and detecting expression of the reporter gene.

In the screening method supra, the non-human mammal deficient in expression of the DNA of the present invention is selected from the aforesaid non-human mammal deficient in expression of the DNA of the present invention, as an animal in which the DNA of the present invention is inactivated by introducing a reporter gene and the reporter gene is expressed under control of a promoter to the DNA of the present invention.

The same examples of the test compound apply to specific compounds used for the screening.

As the reporter gene, the same specific examples apply to this screening method. Preferably employed are β-galactosidase (lacZ), soluble alkaline phosphatase gene, luciferase gene and the like.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing expression of a substance encoded by the reporter gene.

When a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, instead of the polypeptide or receptor protein of the present invention. Thus, the state of expression condition of the polypeptide or the receptor protein of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the polypeptide of the present invention, or its tissue slice section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the aforesaid screening method are compounds that are selected from the test compounds described above and the compounds that promote or inhibit the promoter activity to the DNA of the present invention.

The compound obtained by the screening method above may form salts. As salts of the compound, there may be used salts with physiologically acceptable acids (e.g., inorganic acids, etc.) or bases (e.g., organic acids, etc.), and especially preferred are physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that promotes the promoter activity to the DNA of the present invention can promote expression of the polypeptide of the present invention thereby to promote the function of the polypeptide. Thus, these compounds are useful as drugs for diseases, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicella-zoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease; malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder [e.g., prolactin secretion disorder (e.g., hypoovarianism, spermatic underdevelopment, menopausal symptoms, hypothyroidism, etc.)], pollakiuria, uremia, neurodegenerative disease, etc. (especially, anorexia or the like), especially as safe and low toxic therapeutic/preventive agents (especially, appetite (eating) stimulant).

The compound or its salt that inhibits the promoter activity to the DNA of the present invention can inhibit expression of the polypeptide of the present invention thereby to inhibit the function of the polypeptide. Thus, these compounds are useful as drugs, including preventive/therapeutic drugs (prolactin production inhibitors) for diseases, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, etc.; as safe and low-toxic drugs for the treatment/prevention (prolactin production suppressing agents) of pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, breast cancer lymphoma or Sheehan's syndrome, spermatogenesis disorder, etc. (especially, obesity or the like), etc.; preferably as preventive/therapeutic agents for obesity, hyperphagia, etc.

Furthermore, compounds derived from the compounds obtained by the screening described above may also be used similarly.

The pharmaceuticals comprising the compound obtained by the screening method or its salt may be manufactured as in the aforesaid pharmaceuticals comprising the polypeptide of the present invention or its salt.

Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

A dose of the compound or its salt to be administered varies depending upon target disease, subject to be administered, route of administration, etc., and in oral administration to an adult patient with anorexia (as 60 kg body weight), the compound is administered generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that promotes the promoter activity to the DNA of the present invention is administered to an adult patient with anorexia (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg body weight.

On the other hand, when a compound that inhibits the promoter activity to the DNA of the present invention is orally administered, the compound is orally administered to an adult patient with anorexia (as 60 kg body weight) generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that inhibits the promoter activity to the DNA of the present invention is administered to an adult patient with anorexia (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg body weight.

As described above, the non-human mammal deficient in expressing the DNA of the present invention is extremely useful for screening a compound or its salt that promotes or inhibits the activity of promoter to the DNA of the present invention, and can thus greatly contribute to investigations of causes for various diseases caused by failure to express the DNA of the present invention or to development of preventive/therapeutic agents for these diseases.

Moreover, when a so-called transgenic animal (gene-transfected animal) is prepared by using a DNA containing the promoter region of the polypeptide of the present invention, ligating genes encoding various proteins downstream the same and injecting the genes into animal oocyte, the polypeptide can be specifically synthesized by the animal so that it becomes possible to investigate the activity in vivo. Furthermore, when an appropriate reporter gene is ligated to the promoter region described above to establish a cell line so as to express the gene, such can be used as a survey system of low molecular weight compounds that specifically promotes or suppresses the ability of producing the polypeptide itself of the present invention in vivo.

In the specification and drawings, the codes of bases and amino acids are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
I: inosine
R: adenine (A) or guanine (G)
Y: thymine (T) or cytosine (C)
M: adenine (A) or cytosine (C)
K: guanine (G) or thymine (T)
S: guanine (G) or cytosine (C)
W: adenine (A) or thymine (T)
B: guanine (G), guanine (G) or thymine (T)
D: adenine (A), guanine (G) or thymine (T)
V: adenine (A), guanine (G) or cytosine (C)
N: adenine (A), guanine (G), cytosine (C) or thymine (T), or unknown or other base
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
BHA: benzhydrylamine
pMBHA: p-methyobenzhydrylamine
Tos: p-toluenesulfonyl
Bzl: benzyl
Bom: benzyloxymethyl
Boc: t-butyloxycarbonyl
DCM: dichloromethane
HOBt: 1-hydroxybenztriazole
DCC: N,N'-dicyclohexylcarbodiimide
TFA: trifluoroacetic acid
DEA: diisopropylethylamine
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gin or Q: glutamine
pGlu: pyroglutamic acid
Tyr (I): 3-iodotyrosine
DMF: N,N-dimethylformamide
Fmoc: N-9-fluorenylmethoxycarbonyl
Trt: trityl
Pbf: 2,2,4,6,7-pentamethyldihydrobenzofuran-5-sulfonyl
Clt: 2-chlorotrityl
Bu$^t$: t-butyl
Met (O): methionine sulfoxide The sequence identification numbers in the sequence listing of the specification indicates the following sequences, respectively.

[SEQ ID NO: 1]
This shows a synthetic DNA used for screening of cDNA encoding human GPR8 protein.

[SEQ ID NO: 2]
This shows a synthetic DNA used for screening of cDNA encoding human GPR8 protein.

[SEQ ID NO: 3]
This shows the entire base sequence of human GPR8 protein cDNA, to which the base sequence recognized by restriction enzyme ClaI is added at the 5' end and the base sequence recognized by restriction enzyme SpeI is added at the 3' end.

[SEQ ID NO: 4]
This shows the entire amino acid sequence of human GPR8 protein.

[SEQ ID NO: 5]
This shows the sequence of riboprobe used to determine the expression level of GPR8 receptor protein mRNA in each clone of GPR8-expressed CHO cell line.

[SEQ ID NO: 6]
This shows the amino acid sequence obtained as a result of the amino terminal amino acid sequencing of ligand peptide to GPR8 purified from porcine hypothalamus.

[SEQ ID NO: 7]
This shows an EST sequence (Accession No. AW007531), which complementary strand is supposed to encode a part of the precursor protein of a human homologue to GPR8 ligand peptide.

[SEQ ID NO: 8]
This shows an EST sequence (Accession No. AI500303), which complementary strand is supposed to encode a part of the precursor protein of a human homologue to GPR8 ligand peptide.

[SEQ ID NO: 9]
This shows an EST sequence (Accession No. AI990964), which complementary strand is supposed to encode a part of the precursor protein of a human homologue to GPR8 ligand peptide.

[SEQ ID NO: 10]
This shows an EST sequence (Accession No. AA744804), which complementary strand is supposed to encode a part of the precursor protein of a human homologue to GPR8 ligand peptide.

[SEQ ID NO: 11]
This shows an EST sequence (Accession No. H31598) supposed to encode a part of the precursor protein of a rat homologue to GPR8 ligand peptide.

[SEQ ID NO: 12]
This shows a synthetic DNA used for screening cDNA encoding a part of the precursor protein of a human homologue of the ligand peptide to GPR8.

[SEQ ID NO: 13]
This shows a synthetic DNA used for screening cDNA encoding a part of the precursor protein of a human homologue of the ligand peptide to GPR8.

[SEQ ID NO: 14]
This shows the DNA sequence encoding a part of the precursor protein of a human homologue of the ligand peptide to GPR8 amplified from human brain-derived cDNA.

[SEQ ID NO: 15]
This shows the amino acid sequence for a part of the precursor protein of a human homologue of the ligand peptide to GPR8.

[SEQ ID NO: 16]
This shows the amino acid sequence of a human homologue of the ligand peptide to GPR8 deduced from SEQ ID NO: 15.

[SEQ ID NO: 17]
This shows the amino acid sequence of a human homologue of the ligand peptide to GPR8 deduced from SEQ ID NO:15.

[SEQ ID NO: 18]
This shows the base sequence encoding the amino acid sequence represented by SEQ ID NO:16.

[SEQ ID NO: 19]
This shows the base sequence encoding the amino acid sequence represented by SEQ ID NO:17.

[SEQ ID NO: 20]
This shows the amino acid sequence of human GPR ligand (1–29) synthesized in EXAMPLE 14 described hereinafter.

[SEQ ID NO: 21]
This shows the amino acid sequence of human GPR ligand (1–28) synthesized in EXAMPLE 15 described hereinafter.

[SEQ ID NO: 22]
This shows the amino acid sequence of human GPR ligand (1–27) synthesized in EXAMPLE 16 described hereinafter.

[SEQ ID NO: 23]
This shows the amino acid sequence of human GPR ligand (1–26) synthesized in EXAMPLE 17 described hereinafter.

[SEQ ID NO: 24]
This shows the amino acid sequence of human GPR ligand (1–25) synthesized in EXAMPLE 18 described hereinafter.

[SEQ ID NO: 25]
This shows the amino acid sequence of human GPR ligand (1–24) synthesized in EXAMPLE 19 described hereinafter.

[SEQ ID NO: 26]
This shows the base sequence encoding the amino acid sequence represented by SEQ ID NO: 20.

[SEQ ID NO: 27]
This shows the base sequence encoding the amino acid sequence represented by SEQ ID NO: 21.

[SEQ ID NO: 28]
This shows the base sequence encoding the amino acid sequence represented by SEQ ID NO: 22.

[SEQ ID NO: 29]
This shows the base sequence encoding the amino acid sequence represented by SEQ ID NO: 23.

[SEQ ID NO: 30]
This shows the base sequence encoding the amino acid sequence represented by SEQ ID NO: 24.

[SEQ ID NO: 31]
This shows the base sequence encoding the amino acid sequence represented by SEQ ID NO: 25.

[SEQ ID NO: 32]
This shows the base sequence encoding the amino acid sequence represented by SEQ ID NO: 4.

[SEQ ID NO: 33]
This shows a synthetic DNA used to acquire the 5' upstream sequence of cDNA encoding the precursor protein of a human homologue of the ligand peptide to GPR8.

[SEQ ID NO: 34]
This shows a synthetic DNA used to acquire the 5' upstream sequence of cDNA encoding the precursor protein of a human homologue of the ligand peptide to GPR8.

[SEQ ID NO: 35]
This shows the DNA sequence at the 5' upstream side of cDNA encoding the precursor protein of a human homologue of the ligand peptide to GPR8.

[SEQ ID NO: 36]
This shows a synthetic DNA used to acquire the 3' downstream sequence of cDNA encoding the precursor protein of a human homologue of the ligand peptide to GPR8.

[SEQ ID NO: 37]
This shows a synthetic DNA used to acquire the 3' downstream sequence of cDNA encoding the precursor protein of a human homologue of the ligand peptide to GPR8.

[SEQ ID NO: 38]
This shows the DNA sequence at the 3' downstream side of cDNA encoding the precursor protein of a human homologue of the ligand peptide to GPR8.

[SEQ ID NO: 39]
This shows a synthetic DNA used to acquire cDNA encoding the precursor protein of a human homologue of the ligand peptide to GPR8.

[SEQ ID NO: 40]
This shows a synthetic DNA used to acquire cDNA encoding the precursor protein of a human homologue of the ligand peptide to GPR8.

[SEQ ID NO: 41]
This shows the sequence of cDNA encoding the precursor protein of a human homologue of the ligand peptide to GPR8.

[SEQ ID NO: 42]
This shows the amino acid sequence of the precursor protein of a human homologue of the ligand peptide to GPR8.

[SEQ ID NO: 43]
This shows a synthetic DNA used to acquire the 5' upstream sequence of cDNA encoding the precursor protein of a porcine homologue of the ligand peptide to GPR8.

[SEQ ID NO: 44]
This shows a synthetic DNA used to acquire the 5' upstream sequence of cDNA encoding the precursor protein of a porcine homologue of the ligand peptide to GPR8.

[SEQ ID NO: 45]
This shows the DNA sequence at the 5' upstream side of cDNA encoding the precursor protein of a porcine homologue of the ligand peptide to GPR8.

[SEQ ID NO: 46]
This shows a synthetic DNA used to acquire the 5' upstream sequence of cDNA encoding the precursor protein of a porcine homologue of the ligand peptide to GPR8.

[SEQ ID NO: 47]
This shows a synthetic DNA used to acquire the 5' upstream sequence of cDNA encoding the precursor protein of a porcine homologue of the ligand peptide to GPR8.

[SEQ ID NO: 48]
This shows the DNA sequence at the 5' upstream side of cDNA encoding the precursor protein of a porcine homologue of the ligand peptide to GPR8.

[SEQ ID NO: 49]
This shows a synthetic DNA used to acquire the 3' downstream sequence of cDNA encoding the precursor protein of a porcine homologue of the ligand peptide to GPR8.

[SEQ ID NO: 50]
This shows a synthetic DNA used to acquire the 3' downstream sequence of cDNA encoding the precursor protein of a porcine homologue of the ligand peptide to GPR8.

[SEQ ID NO: 51]
This shows the DNA sequence at the 3' downstream side of cDNA encoding the precursor protein of a porcine homologue of the ligand peptide to GPR8.

[SEQ ID NO: 52]
This shows a synthetic DNA used to acquire cDNA encoding the precursor protein of a porcine homologue of the ligand peptide to GPR8.

[SEQ ID NO: 53]
This shows a synthetic DNA used to acquire cDNA encoding the precursor protein of a porcine homologue of the ligand peptide to GPR8.

[SEQ ID NO: 54]
This shows the sequence of cDNA encoding the precursor protein of a porcine homologue of the ligand peptide to GPR8.

[SEQ ID NO: 55]
This shows the amino acid sequence of the precursor protein of a porcine homologue of the ligand peptide to GPR8.

[SEQ ID NO: 56]
This shows the amino acid sequence of a porcine homologue of the ligand peptide to GPR8 deduced from SEQ ID NO: 55.

[SEQ ID NO: 57]
This shows the amino acid sequence of a porcine homologue of the ligand peptide to GPR8 deduced from SEQ ID NO: 55.

[SEQ ID NO: 58]
This shows the base sequence encoding the amino acid sequence represented by SEQ ID NO: 56.

[SEQ ID NO: 59]
This shows the base sequence encoding the amino acid sequence represented by SEQ ID NO: 57.

[SEQ ID NO: 60]
This shows a synthetic DNA used to acquire cDNA encoding a part of the precursor protein of a rat homologue of the ligand peptide to GPR8.

[SEQ ID NO: 61]

This shows a synthetic DNA used to acquire cDNA encoding a part of the precursor protein of a rat homologue of the ligand peptide to GPR8.

[SEQ ID NO: 62]

This shows the sequence of cDNA encoding a part of the precursor protein of a rat homologue of the ligand peptide to GPR8.

[SEQ ID NO: 63]

This shows a synthetic DNA used to acquire the 5' upstream sequence of cDNA encoding the precursor protein of a rat homologue of the ligand peptide to GPR8.

[SEQ ID NO: 64]

This shows a synthetic DNA used to acquire the 5' upstream sequence of cDNA encoding the precursor protein of a rat homologue of the ligand peptide to GPR8.

[SEQ ID NO: 65]

This shows the 5' upstream DNA sequence of cDNA encoding the precursor protein of a rat homologue of the ligand peptide to GPR8.

[SEQ ID NO: 66]

This shows a synthetic DNA used to acquire the 3' downstream sequence of cDNA encoding the precursor protein of a rat homologue of the ligand peptide to GPR8.

[SEQ ID NO: 67]

This shows a synthetic DNA used to acquire the 3' downstream sequence of cDNA encoding the precursor protein of a rat homologue of the ligand peptide to GPR8.

[SEQ ID NO: 68]

This shows the 3' downstream sequence of cDNA encoding the precursor protein of a rat homologue of the ligand peptide to GPR8.

[SEQ ID NO: 69]

This shows a synthetic DNA used to acquire cDNA encoding the precursor protein of a rat homologue of the ligand peptide to GPR8.

[SEQ ID NO: 70]

This shows a synthetic DNA used to acquire cDNA encoding the precursor protein of a rat homologue of the ligand peptide to GPR8.

[SEQ ID NO: 71]

This shows the sequence of cDNA encoding the precursor protein of a rat homologue of the ligand peptide to GPR8.

[SEQ ID NO: 72]

This shows the amino acid sequence of the precursor protein of a rat homologue of the ligand peptide to GPR8.

[SEQ ID NO: 73]

This shows the amino acid sequence of a rat homologue of the ligand peptide to GPR8 deduced from SEQ ID NO: 72.

[SEQ ID NO: 74]

This shows the amino acid sequence of a rat homologue of the ligand peptide to GPR8 deduced from SEQ ID NO: 72.

[SEQ ID NO: 75]

This shows the base sequence encoding the amino acid sequence represented by SEQ ID NO: 73.

[SEQ ID NO: 76]

This shows the base sequence encoding the amino acid sequence represented by SEQ ID NO: 74.

[SEQ ID NO: 77]

This shows the mouse genome fragment sequence supposed to encode a part of the precursor protein of a mouse homologue of the GPR8 ligand peptide.

[SEQ ID NO: 78]

This shows a synthetic DNA used to screen cDNA encoding a part of the precursor protein of a mouse homologue of the ligand peptide to GPR8.

[SEQ ID NO: 79]

This shows a synthetic DNA used to screen cDNA encoding a part of the precursor protein of a mouse homologue of the ligand peptide to GPR8.

[SEQ ID NO: 80]

This shows the DNA sequence encoding a part of the precursor protein of a human homologue of the ligand peptide to GPR8, amplified from mouse testis-derived cDNA.

[SEQ ID NO: 81]

This shows a synthetic DNA used to acquire the 5' upstream sequence of cDNA encoding the precursor protein of a mouse homologue of the ligand peptide to GPR8.

[SEQ ID NO: 82]

This shows a synthetic DNA used to acquire the 5' upstream sequence of cDNA encoding the precursor protein of a mouse homologue of the ligand peptide to GPR8.

[SEQ ID NO: 83]

This shows the DNA sequence at the 5' upstream side of cDNA encoding the precursor protein of a mouse homologue of the ligand peptide to GPR8.

[SEQ ID NO: 84]

This shows a synthetic DNA used to acquire the 3' downstream sequence of cDNA encoding the precursor protein of a mouse homologue of the ligand peptide to GPR8.

[SEQ ID NO: 85]

This shows a synthetic DNA used to acquire the 3' downstream sequence of cDNA encoding the precursor protein of a mouse homologue of the ligand peptide to GPR8.

[SEQ ID NO: 86]

This shows the DNA sequence at the 3' downstream side of cDNA encoding the precursor protein of a mouse homologue of the ligand peptide to GPR8.

[SEQ ID NO: 87]

This shows a synthetic DNA used to acquire cDNA encoding the precursor protein of a mouse homologue of the ligand peptide to GPR8.

[SEQ ID NO: 88]

This shows a synthetic DNA used to acquire cDNA encoding the precursor protein of a mouse homologue of the ligand peptide to GPR8.

[SEQ ID NO: 89]

This shows the sequence of a cDNA encoding the precursor protein of a mouse homologue of the ligand peptide to GPR8.

[SEQ ID NO: 90]
This shows the amino acid sequence of precursor protein of a mouse homologue of the ligand peptide to GPR8.

[SEQ ID NO: 91]
This shows the amino acid sequence of a mouse homologue of the ligand peptide to GPR8 deduced from SEQ ID NO: 90.

[SEQ ID NO: 92]
This shows the amino acid sequence of a mouse homologue of the ligand peptide to GPR8 deduced from SEQ ID NO: 90.

[SEQ ID NO: 93]
This shows the base sequence encoding the amino acid sequence represented by SEQ ID NO: 91.

[SEQ ID NO: 94]
This shows the base sequence encoding the amino acid sequence represented by SEQ ID NO: 92.

[SEQ ID NO: 95]
This shows the amino acid sequence of human GPR8 ligand (1–23) oxidation product synthesized in EXAMPLE 44 later described.

[SEQ ID NO: 96]
This shows the amino acid sequence of human GPR8 ligand (1–22) synthesized in EXAMPLE 45 later described.

[SEQ ID NO: 97]
This shows the amino acid sequence of human GPR8 ligand (1–21) synthesized in EXAMPLE 46 later described.

[SEQ ID NO: 98]
This shows the amino acid sequence of human GPR8 ligand (1–20) synthesized in EXAMPLE 47 later described.

[SEQ ID NO: 99]
This shows the amino acid sequence of human GPR8 ligand (1–19) synthesized in EXAMPLE 48 later described.

[SEQ ID NO: 100]
This shows the amino acid sequence of human GPR8 ligand (1–18) synthesized in EXAMPLE 49 later described.

[SEQ ID NO: 101]
This shows the amino acid sequence of human GPR8 ligand (1–17) synthesized in EXAMPLE 50 later described.

[SEQ ID NO: 102]
This shows the amino acid sequence of human GPR8 ligand (1–16) synthesized in EXAMPLE 51 later described.

[SEQ ID NO: 103]
This shows the amino acid sequence of porcine GPR8 ligand (1–23) oxidation product synthesized in EXAMPLE 54 later described.

[SEQ ID NO: 104]
This shows the amino acid sequence of rat or mouse GPR8 ligand (1–23) oxidation product synthesized in EXAMPLE 55 later described.

[SEQ ID NO: 105]
This shows the amino acid sequence of human GPR8 ligand (1–23) synthesized in EXAMPLE 12 later described.

[SEQ ID NO: 106]
This shows the amino acid sequence of [$N^{\alpha}$-Acetyl-Trp$^1$]-human GPR8 ligand (1–23) synthesized in EXAMPLE 56 later described.

[SEQ ID NO: 107]
This shows the amino acid sequence of human GPR8 ligand (2–23) synthesized in EXAMPLE 57 later described.

[SEQ ID NO: 108]
This shows the amino acid sequence of human GPR8 ligand (4–23) synthesized in EXAMPLE 58 later described.

[SEQ ID NO: 109]
This shows the amino acid sequence of human GPR8 ligand (9–23) synthesized in EXAMPLE 59 later described.

[SEQ ID NO: 110]
This shows the amino acid sequence of human GPR8 ligand (15–23) synthesized in EXAMPLE 60 later described.

[SEQ ID NO: 111]
This shows the amino acid sequence of [N-Acetyl-Tyr$^2$]-human GPR8 ligand (2–23) synthesized in EXAMPLE 61 later described.

[SEQ ID NO: 112]
This shows the amino acid sequence of [D-Trp$^1$]-human GPR8 ligand (1–23) synthesized in EXAMPLE 62 later described.

[SEQ ID NO: 113]
This shows the amino acid sequence of [N-3-Indolepropanyl-Tyr$^2$]-human GPR8 ligand (2–23) synthesized in EXAMPLE 63 later described.

[SEQ ID NO: 114]
This shows the base sequence encoding the amino acid sequence represented by SEQ ID NO: 96.

[SEQ ID NO: 115]
This shows the base sequence encoding the amino acid sequence represented by SEQ ID NO: 97.

[SEQ ID NO: 116]
This shows the base sequence encoding the amino acid sequence represented by SEQ ID NO: 98.

[SEQ ID NO: 117]
This shows the base sequence encoding the amino acid sequence represented by SEQ ID NO: 99.

[SEQ ID NO: 118]
This shows the base sequence encoding the amino acid sequence represented by SEQ ID NO: 100.

[SEQ ID NO: 119]
This shows the base sequence encoding the amino acid sequence represented by SEQ ID NO: 101.

[SEQ ID NO: 120]
This shows the base sequence encoding the amino acid sequence represented by SEQ ID NO: 102.

[SEQ ID NO: 121]
This shows the base sequence encoding the amino acid sequence represented by SEQ ID NO: 107.

[SEQ ID NO: 122]
This shows the base sequence encoding the amino acid sequence represented by SEQ ID NO: 108.

[SEQ ID NO: 123]
This shows the base sequence encoding the amino acid sequence represented by SEQ ID NO: 109.

[SEQ ID NO: 124]
This shows the base sequence encoding the amino acid sequence represented by SEQ ID NO: 110.

[SEQ ID NO: 125]

This shows the base sequence encoding the amino acid sequence represented by SEQ ID NO: 6.

Transformant *Escherichia coli* DH5α/pAKK0-GPR8, which was obtained in EXAMPLE 3 later described, has been deposited since Feb. 27, 2001 on the Institute for Fermentation (IFO), located at 2-17-85, Juso Honcho, Yodogawa-ku, Osaka-shi, Osaka, Japan, under the Accession Number IFO 16564 and since on Apr. 11, 2001 on the National Institute of Advanced Industrial Science and Technology, International Patent Organism Depositary, located at Central 6, 1-1-1 Higashi, Tsukuba, Ibaraki, Japan, under the Accession Number FERM BP-7540, respectively.

Transformant *Escherichia coli* TOP10/pCR2.1-TOPO Human GPR8 Ligand Precursor, which was obtained in EXAMPLE 28 later described, has been deposited since Feb. 27, 2001 on the Institute for Fermentation (IFO), located at 2-17-85, Juso Honcho, Yodogawa-ku, Osaka-shi, Osaka, Japan, under the Accession Number IFO 16568 and since on Apr. 11, 2001 on the National Institute of Advanced Industrial Science and Technology, International Patent Organism Depositary, located at Central 6, 1-1-1 Higashi, Tsukuba, Ibaraki, Japan, under the Accession Number FERM BP-7544, respectively.

Transformant *Escherichia Escherichia coli* TOP10/pCR2.1-TOPO Porcine GPR8 Ligand Precursor, which was obtained in EXAMPLE 32 later described, has been deposited since Feb. 27, 2001 on the Institute for Fermentation (IFO), located at 2-17-85, Juso Honcho, Yodogawa-ku, Osaka-shi, Osaka, Japan, under the Accession Number IFO 16565 and since on Apr. 11, 2001 on the National Institute of Advanced Industrial Science and Technology, International Patent Organism Depositary, located at Central 6, 1-1-1 Higashi, Tsukuba, Ibaraki, Japan, under the Accession Number FERM BP-7541, respectively.

Transformant *Escherichia coli* TOP10/pCR2.1-TOPO Rat GPR8 Ligand Precursor, which was obtained in EXAMPLE 36 later described, has been deposited since Feb. 27, 2001 on the Institute for Fermentation (IFO), located at 2-17-85, Juso Honcho, Yodogawa-ku, Osaka-shi, Osaka, Japan, under the Accession Number IFO 16567 and since on Apr. 11, 2001 on the National Institute of Advanced Industrial Science and Technology, International Patent Organism Depositary, located at Central 6, 1-1-1 Higashi, Tsukuba, Ibaraki, Japan, under the Accession Number FERM BP-7543, respectively.

Transformant *Escherichia coli* TOP10/pCR2.1-TOPO Mouse GPR8 Ligand Precursor, which was obtained in EXAMPLE 41 later described, has been deposited since Feb. 27, 2001 on the Institute for Fermentation (IFO), located at 2-17-85, Juso Honcho, Yodogawa-ku, Osaka-shi, Osaka, Japan, under the Accession Number IFO 16566 and since on Apr. 11, 2001 on the National Institute of Advanced Industrial Science and Technology, International Patent Organism Depositary, located at Central 6, 1-1-1 Higashi, Tsukuba, Ibaraki, Japan, under the Accession Number FERM BP-7542, respectively.

EXAMPLES

The present invention will be described in more detail below, with reference to EXAMPLES, but is not deemed to limit the scope of the present invention thereto.

Example 1

Amplification of Human GPR8 cDNA by PCR Using Human Brain-derived cDNA

Reverse transcription was performed by using random primers, in which human brain-derived poly(A) $^+$RNA (Clontech Laboratories, Inc.) was used as a template. TaKaRa RNA PCR ver. 2.1 Kit was used for the reverse transcription. Next, amplification was carried out by PCR, in which the resulting reverse transcription product was used as a template and synthetic primers represented by SEQ ID NO: 1 and SEQ ID NO: 2 were used. The synthetic primers were constructed so as to amplify the gene in the region to be translated to its receptor protein was amplified, in which the recognition sequences of restriction enzymes were added to the 5' and 3' ends, respectively, so that the base sequences recognized by restriction enzymes ClaI and SpeI were added to the gene at the 5' and 3' ends, respectively. The reaction solution was composed of 5 µl of cDNA template, 0.4 µM each of the synthetic DNA primers, 0.8 mM dNTPs and 0.5 µl of pfu polymerase (Stratagene), to which buffer attached to the enzyme was added to make the total volume of 50 µl. For amplification, after heating at 94° C. for 60 seconds, one cycle set to include 94° C. for 60 seconds, 65° C. for 60 seconds and 72° C. for 150 seconds was repeated 35 times, using Thermal Cycler (PE Biosystems). The amplified product was confirmed by 0.8% agarose gel electrophoresis followed by staining with ethidium bromide.

Example 2

Subcloning of the PCR Product to Plasmid Vector and Confirmation of the Amplified cDNA Sequence by Decoding the Base Sequence of the Inserted cDNA Region The reaction solution obtained by PCR in EXAMPLE 1 was subjected to 0.8% low melting agarose gel electrophoresis for separation. The band parts were excised from the gel with a razor blade and ground to small pieces, which were then extracted with phenol/choloroform and precipitated in ethanol to recover DNAs. According to the protocol attached to PCR SCRIPT™ Amp SK(+) Cloning Kit (Stratagene), the recovered DNAs were subcloned into the plasmid vector, PCR-SCRIPT™ Amp SK(+) (a cloning vector derived from a phagemid including an ampicillin-resistance gene). The recombinant vectors were introduced into. *Escherichia coli* DH5α competent cells (Toyobo Co., Ltd.) to produce transformants. Then, clones having a cDNA-inserted fragment were selected in an LB agar culture medium containing ampicillin, IPTG and X-gal. Only clones exhibiting white color were picked with a sterilized toothpick to acquire transformant *Escherichia coli* DH5α GPR8. The individual clones were cultured overnight in an LB culture medium containing ampicillin, and plasmid DNAs were prepared using QIAwell 8 Plasmid Kit (Qiagen). An aliquot of the DNAs thus prepared was digested with restriction enzymes ClaI and SpeI to confirm the size of the receptor cDNA fragment inserted. Sequencing was carried out by using a DyeDeoxy Terminator Cycle Sequencing Kit (PE Biosystems), and the DNAs were decoded by using a fluorescent automatic sequencer (SEQ ID NO: 3). FIG. 1 shows the entire base sequence of human GPR8 receptor protein cDNA (SEQ ID NO: 32 and the entire amino acid sequence of human GPR8 receptor protein cDNA (SEQ ID NO: 4) translated therefrom.

Example 3

Preparation of CHO Cells which Express GPR8

Using Plasmid Midi Kit (Qiagen), plasmid DNA was prepared from the *E. coli* clones transformed by the plasmid bearing the gene encoding the full-length amino acid sequence of human brain-derived GPR8, which sequence was confirmed in EXAMPLE 2, having the ClaI and SpeI recognition sequences added at the 5' and 3' ends, respectively. The plasmid DNA was digested with the restriction enzymes ClaI and SpeI to excise the insert DNA. The insert DNA was electrophoresed, then excised from the agarose gel with a razor blade, ground into small pieces, then extracted with phenol and with phenol/chloroform, and precipitated in ethanol to recover DNAs. The insert DNA was added to the animal cell expression vector plasmid pAKK0-111H (the same vector plasmid as pAKK01.11 H described in Hinuma, S., et al., Biochim. Biophys. Acta, 1219, 251–259, 1994), which was digested with ClaI and SpeI, followed by ligation using T4 ligase (Takara Shuzo Co., Ltd.) to construct a receptor protein expression plasmid pAKK0-GPR8. *Escherichia coli* transformed by this plasmid pAKK0-GPR8 was named *Escherichia coli* DH5α/pAKK0-GPR8.

*E. coli* DH5α (Toyobo Co., Ltd.) transfected with pAKK0-GPR8 was cultured and the pAKK0-GPR8 plasmid DNA was prepared using Plasmid Midi Kit (Qiagen). Using CellPhect Transfection Kit (Amersham Pharmacia Biotech), the plasmid DNA was transfected to CHO dhfr⁻ cells in accordance with the protocol attached. DNA, 4.5 µg, was co-precipitated with calcium phosphate in suspension. The resulting suspension was added to a 6 cm-diameter Petri dish, in which $5 \times 10^5$ or $1 \times 10^6$ CHO dhfr⁻ cells had been seeded before 24 hours. The cells were cultured in MEMα medium containing 10% fetal calf serum for one day. After passage, the cells were cultured in nucleic acid-free MEMα selection medium containing 10% dialyzed fetal calf serum, 47 clones of the transformant colony GPR8-expressed CHO cells, growing in the selection medium, were selected.

Example 4

Selection of the CHO/GPR8 Cell Line with High Expression of the Full-length Human GPR8 Protein mRNA The expression level of the full-length GPR8 protein mRNAs of 47 clones from the CHO/GPR8 cell line established in EXAMPLE 3 was determined as follows, using Cytostar T Plate (Amersham Pharmacia Biotech) in accordance with the protocol attached. Each clone of the CHO/GPR8 cell line was inoculated on Cytostar T Plate in $2.5 \times 10^4$ cells/well. After culturing for 24 hours, the cells were fixed with 10% formalin. To each well 0.25% Triton X-100 was added to increase cell permeability, $^{35}$S-labeled riboprobe of SEQ ID NO: 5 was added to the cells for hybridization. Free riboprobe was digested by adding 20 µg/ml RNase A to each well. After the plate was thoroughly washed, radioactivity of the hybridized riboprobe was assayed with Topcounter. The cell line with a high radioactivity provides a high mRNA expression level. Three clones (#17, #41 and #46), which showed a high mRNA expression level, were used for the following experiment, especially clone #17 as a main clone.

Example 5

Determination of the Intracellular cAMP Level Using GPR8-Expressed CHO Cells

The CHL/GPR8 cells produced in EXAMPLE 4 and mock CHO cells were inoculated on a 24-well plate in $5 \times 10^4$ cells/well, followed by cultivation for 48 hours. The cells were washed with Hanks' buffer (pH 7.4) containing 0.2 mM 3-isobutyl-methylxanthine, 0.05% BSA and 20 mM HEPES (hereinafter Hanks' buffer (pH 7.4) containing 0.2 mM 3-isobutyl-methylxanthine, 0.05% BSA and 20 mM HEPES is referred to as a reaction buffer). Thereafter, 0.5 ml of the reaction buffer was added to the system, which was kept warm in an incubator for 30 minutes. After the reaction buffer was removed, 0.25 ml of a fresh reaction buffer was added to the cells. Then, 0.25 ml of the reaction buffer containing a sample fluid and 2 µM forskolin was added to the cells followed by reacting at 37° C. for 24 minutes. By adding 100 µl of 20% perchloric acid, the reaction was terminated. The reaction mixture was then allowed to stand on ice for an hour to extract intracellular cAMP. The amount of cAMP in the extract was measured using cAMP EIA kit (Amersham Pharmacia Biotech).

Example 6

Assay for GTPγ S Binding Activity Using the GPR8-expressed CHO Cell Membrane Fraction The [$^{35}$S]-guanosine 5'-(γ-thio)triphosphate binding promoting activity on a GPR8-expressed CHO cell membrane fraction was assayed by the following procedures. First, preparation of the membrane fraction is described. To $1 \times 10^8$ of CHO/GPR8 cells was added 10 ml of a homogenate buffer (10 mM NaHCO₃, 5 mM EDTA, 0.5 mM PMSF, 1 µg/ml pepstatin, 4 µg/ml E64, 20 µg/ml leupeptin). The mixture was homogenized by using Polytron (12,000 rpm, 1 min.). The cell homogenate was subjected to centrifugation (1,000 g, 15 mins.) to obtain the supernatant. Next, the supernatant was subjected to ultracentrifugation (Beckman type 30 rotor, 30,000 rpm, 1 hour). The resulting precipitate was used as GPR8-expressed CHO cell membrane fraction.

The GTPγ S binding activity was assayed as follows. The GPR8-expressed CHO cell membrane fraction was diluted with a membrane dilution buffer (50 mM Tris-hydrochloride buffer (pH 7.4), 5 mM MgCl₂, 150 mM NaCl, 1 µM GDP) to prepare a cell membrane fraction solution for assay having a protein level of 30 mg/ml. To 200 µl of the cell membrane fraction solution for assay were added 2 µl of 51.5 nM [$^{35}$S]-guanosine 5'-(γ-thio)triphosphate (NEN Co.) and a sample fluid. The resulting solution mixture was kept at 25° C. for an hour. The mixture was filtrated through a filter. After washing twice with 1.5 ml of a wash buffer (50 mM Tris-hydrochloride buffer (pH 7.4), 5 mM MgCl₂, 1 mM EDTA, 0.1% BSA), radioactivity of the filter was measured with a liquid scintillation counter.

Example 7

Detection of the cAMP Production Suppressing and GTPγ S Binding Promoting Activity Contained in Porcine Hypothalamus Extract Specific to CHO/GPR8 Cell Line High performance liquid chromatography (HPLC) fractions of the porcine hypothalamus extract were prepared by the following procedures. Porcine hypothalamus, 500 g (corresponding to 30 pigs), which had been purchased from Tokyo Shibaura Zoki Co. and kept under ice cooling after the hypothalamus was withdrawn from porcine on the day of their sacrifice, was minced, immediately put into 2.0 liters of boiling distilled water and boiled for 10 minutes. Immediately after the boiling, the minced product was ice-cooled and 120 ml of acetic acid was added to the homogenate to make the final concentration 1.0 M. Using POLYTRON (20,000 rpm, 6 mins.), the mixture was homogenized. The homogenate was centrifuged (8,000 rpm, 30 mins.) and the supernatant was taken out. After 2.0 liters of 1.0 M acetic acid was added to the precipitate, the mixture was again homogenized using POLYTRON. The homogenate was stirred overnight and then centrifuged (8,000 rpm, 30 mins.) to obtain the supernatant. After 2-fold volume of chilled acetone was dropwise added slowly to the supernatant at 4° C., the supernatant obtained by the first centrifugation was stirred overnight and, the supernatant obtained by the second centrifugation was stirred for 4 hours. The acetone-added extract was centrifuged (8,000 rpm, 30 mins.) to remove the precipitate and acetone was evaporated off in vacuum from the supernatant, using an evaporator. An equal volume of diethyl ether was added to the acetone-free extract, the ethereal layer containing lipids was separated using a separating funnel to recover the aqueous layer. After the lipids were removed with ether, the extract was concentrated in vacuum using an evaporator to completely remove the ether. The concentrate was filtrated through a glass fiber filter paper (Advantech, DP70 (90 mmφ)) and the filtrate was charged in a glass column (30φ×240 mm) packed with C18 column (YMC, YMCgel ODS-AM 120-S50). After washing with 400 ml of 1.0 M acetic acid, the column was eluted with 500 ml of 60% acetonitrile containing 0.1% trifluoroacetic acid. The eluate was concentrated in vacuum, the solvent was distilled off and then the concentrate was lyophilized. About 0.5 g of the lyophilized product was dissolved in 30 ml of 10% acetonitrile containing 0.1% trifluoroacetic acid. An aliquot of 10 ml each was subjected to HPLC on 10% to 60% acetonitrile containing 0.1% trifluoroacetic acid by density gradient elution using C18 column (Toso, TSKGEL ODS 80™ (21.5φ×300 mm)). HPLC was performed twice. The eluate was fractionated into 60 fractions and the eluates in three runs were collected. Each fraction was concentrated and evaporated to dryness in vacuum. The residue was dissolved in 0.5 ml of dimethylsulfoxide (DMSO).

A DMSO solution of the HPLC fraction obtained as described above was added to the CHL/GPR8 cells by the procedures shown in EXAMPLE 5 to determine the level of cAMP produced in the cells. As a result, a marked activity of suppressing cAMP product was noted in fraction #30. Also, the GTPγ S binding promoting activity was examined on a similar sample fluid using the GPR8-expressed CHO cells. Likewise, a marked activity was confirmed around fraction #30. Since these activities were not observed in other receptor expression cells, the results reveal that a ligand active substance specific to GPR8 was present in the porcine hypothalamus extract.

Example 8

Inactivation of the Active Substance Showing the Intracellular cAMP Production Suppressing Activity Specific to GPR8-expressed CHO Cells in Porcine Hypothalamus Extract The HPLC fraction #30 which showed the intracellular cAMP production suppressing activity on the GPR8-expressed CHO cells in EXAMPLE 7 was treated with a proteolytic enzyme, pronase (Sigma, protease Type XIV (P5147)) to examine if the active substance is proteinaceous.

The HPLC fraction (#30), 2 μl, from the hypothalamus extract described above was added to 200 μl of 0.2 M ammonium acetate and 3 μl of pronase was further added thereto. After incubation at 37° C. for 2 hours, the culture was boiled in boiling water for 10 minutes to inactivate the pronase. To the reaction solution was added 2 ml of distilled water containing 0.05 mg of BSA and 0.05 mg of CHAPS, followed by lyophilization. In order to examine if pronase itself, or heating and lyophilization have an effect, pronase alone, the HPLC fraction alone, and a mixture of the HPLC fraction with pronase alone after its heating were treated in a similar manner and then lyophilized. Each sample fluid lyophilized was added to the GPR8-expressed CHO cells by the procedures shown in EXAMPLE 5 and the intracellular cAMP production suppressing activity was assayed. Since the active substance showing the intracellular cAMP production suppressing activity on the GPR8-expressed CHO cells in the porcine hypothalamus extract was completely inactivated by the pronase, it was revealed that this substance was a protein or peptide.

Example 9

Purification of the Active Substance Showing the GTPγ S Binding Promoting Activity Specific to the GPR8-expressed CHO Cell Membrane Fraction from Porcine Hypothalamus A representative example of purifying from porcine hypothalamus the active substance showing a ligand activity specific to GPR8 using the GTPγ S binding promoting activity on the GPR8-expressed CHO cell membrane fraction as an indicator is described below in a specific manner. Porcine hypothalamus, 500 g (corresponding to 30 pigs) was extracted with 1.0 M acetic acid by the same procedures as described in EXAMPLE 7. After precipitation and removal of lipids with ether, the extract was adsorbed to a column packed with C18 (YMC, YMCgel ODS-AM 120-S50) followed by elution with 60% acetonitrile containing 0.1% trifluoroacetic acid. After the eluate was concentrated and lyophilized, the concentrate was subjected to HPLC using C18 column (Toso, TSKgel ODS-80TS (21.5φ×300 mm)) to obtain the active fraction. The activity was recovered in fraction #30, which was further purified by the following procedures.

The fraction was dissolved in 10 ml of 10 mM ammonium formate containing 10% acetonitrile. After the solution was passed through a cationic exchange column (Toso, TSKgel SP-5PW (20 mmφ×150 mm)), the column was eluted with 10 mM to 2.0 M ammonium formate containing 10% acetonitrile by means of density gradient. The activity was recovered at about 0.8M ammonium formate. The active fraction was lyophilized and dissolved in 1.0 ml of 10% acetonitrile containing 0.1% trifluoroacetic acid. After the solution was passed through a CN column (Nomura Chemical Co., Ltd., Develosil CN-UG-5 (4.6 mmφ×250 mm)), elution was performed by density gradient with 21% to 26% acetonitrile containing 0.1% trifluoroacetic acid. The activity appeared around 22.1% acetonitrile. The active fraction was lyophilized and dissolved in 0.1 ml of DMSO. The solution was further added with 0.4 ml of 10% acetonitrile containing 0.1% trifluoroacetic acid, which was passed through an ODS column (Wako Pure Chemical Industries, Co., Ltd., Wakosil-II 3C18HG (2.0 mmφ×150 mm)) followed by elution in terms of density gradient of 22.5% to 32.5% acetonitrile containing 0.1% trifluoroacetic acid. The activity appeared as a single peak around 26.5% acetonitrile.

Example 10

Amino-Terminal Amino Acid Sequencing of the Active Substance Showing the GTPγ S Binding Promoting Activity Specific to the GPR8-expressed CHO Cells Purified from Porcine Hypothalamus and EST Sequence Predicted to Encode a Part of Human and Rat Homologue Peptide Precursor Proteins of GPR8 Ligand Amino-terminal amino acid sequencing of the active substance showing the GTPγS binding promoting activity specific to the GPR8-expressed CHO cell membrane fraction purified in EXAMPLE 9 was performed. Since it was speculated that the active substance would be a protein or peptide as demonstrated in EXAMPLE 8, amino-terminal amino acid sequencing was conducted by use of Procise 494 Protein Sequencer available from Perkin-Elmer, using the eluate containing the active peak. As a result, the sequence represented by SEQ ID: 6 was obtained in the region up to 17 residues from the amino terminus. This sequence was considered to be a part of the ligand peptide.

Survey of gene database based on this sequence gave some EST (Expressed Sequence Tag) sequences, and it is supposed that the sequence or its complementary strand would encode a part of the precursor protein of this peptide. These sequences have the following accession numbers, cDNA origin, sequence size and sequence identification numbers: AW007531 (anaplastic oligodentroglioma, 438 bases, SEQ ID NO: 7), AI500303 (anaplastic oligodentroglioma, 264 bases, SEQ ID NO: 8), AI990964 (colonic mucosa from patient of Crohn's disease, 424 bases, SEQ ID NO: 9), AA744804 (germinal center B cell, 375 bases, SEQ ID NO: 10), H31598 (PC12 cells, 260 bases, SEQ ID NO: 11). The first 4 sequences are derived from human and the last sequence is derived from rat. The DNA sequences of these ESTs extremely well coincided with the region encoding the amino acid sequence corresponding to the sequence of the active peptide isolated from porcine hypothalamus. Furthermore, the translated amino acid sequence was almost identical with the sequence of peptide isolated and clarified from porcine hypothalamus, except that the 5th residue Thr is Val. Based on the foregoing, it was deduced that these ESTs would encode a part of human and rat homologue precursor proteins of the ligand peptide to GPR8.

Example 11

Amplification of Human cDNA Encoding a Part of GPR8 Ligand Peptide Precursor and Decoding of the Amplified cDNA Sequence Based on the putative EST sequences to encode a part of precursor protein of the GPR8 ligand peptide described in EXAMPLE 10, primers were designed and cDNA encoding a part of GPR8 ligand peptide precursor was amplified from human brain-derived cDNA by PCR.

Reverse transcription was performed by using random primers, in which human brain-derived poly(A) +RNA (Clontech Laboratories, Inc.) was used as a template. ReverTra Ace (Toyobo Co., Ltd.) was used for the reverse transcription. Next, amplification was carried out by PCR using synthetic primers represented by SEQ ID NO: 12 and SEQ ID NO: 13 designed on the basis of the EST sequences described in EXAMPLE 10. The reaction solution was composed of 2 μl of cDNA template, 0.5 μM each of the synthetic DNA primers, 1.6 mM dNTPs and 0.2 μl of LA Taq (Takara Shuzo Co., Ltd.), to which buffer attached to the enzyme was added to make the total volume of 20 μl. For amplification, after heating at 96° C. for 120 seconds using Thermal Cycler (PE Biosystems), one cycle set to include 96° C. for 30 seconds and 72° C. for 45 seconds was repeated 4 times, one cycle set to include 96° C. for 30 seconds and 70° C. for 45 seconds was repeated 4 times, one cycle set to include 96° C. for 30 seconds and 68° C. for 45 seconds was repeated 4 times, one cycle set to include 96° C. for 30 seconds, 64° C. for 30 seconds and 72° C. for 45 seconds was repeated 5 times, one cycle set to include 96° C. for 30 seconds, 60° C. for 30 seconds and 72° C. for 45 seconds was repeated 20 times, and finally, the mixture was kept at 72° C. for 10 minutes. The amplified product was confirmed by 3% agarose gel electrophoresis followed by staining with ethidium bromide.

The PCR solution was subjected to 3% low melting agarose gel electrophoresis for separation. After the band parts were excised from the gel with a razor blade, DNA was recovered using QIAquick Gel Extraction Kit (Qiagen). The recovered DNA was subcloned to plasmid vector pCR2.1-TOPO in accordance with the protocol of TOPO TA Cloning Kit (Invitrogen), which was then introduced to *Escherichia coli* TOP10 (Invitrogen) for transfection. Then, clones having a cDNA-inserted fragment were selected in an LB agar culture medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for determining base sequence was carried out by using a DyeDeoxy Terminator Cycle Sequence Kit (PE Biosystems), and the DNAs were decoded using a fluorescent automatic sequencer to obtain the DNA sequence represented by SEQ ID NO: 14. As predicted, the peptide sequence corresponding to the active peptide, which was isolated from porcine hypothalamus and clarified in its sequence, was present in a part (SEQ ID NO: 15) of the GPR8 ligand peptide precursor protein translated from the aforesaid sequence. In the C terminus, the Arg-Arg sequence (Seidah, N. G. et al., Ann. N. Y. Acad. Sci., 839, 9–24, 1998) was present at 2 sites, from which sequence a normal physiologically active peptide was considered to be excised. In view of the foregoing, it was deduced that the amino acid sequence of a human homologue of the GPR8 ligand peptide would be either SEQ ID NO: 16 or 17 or both.

Example 12

Production of Fmoc-human GPR8 Ligand (1–23): Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 105) and human GPR8 Ligand (1–23): Trp-Tyr-Lys-His-Val-Ala-Ser-Pro-Arg-Tyr-His-Thr-Val-Gly-Arg-Ala-Ala-Gly-Leu-Leu-Met-Gly-Leu (SEQ ID NO: 16)

Using as a starting material 0.25 mmol (0.76 mmol/g) of Fmoc-Leu-O-Clt resin obtained by introducing Fmoc-Leu into commercially available 2-chlorotrityl resin (Clt resin, 1.33 mmol/g) and using a peptide synthesizer AMI 433A, condensation was performed by the Fmoc/DCC/HOBt method sequentially in the order of Fmoc-Gly, Fmoc-Met, Fmoc-Leu, Fmoc-Leu, Fmoc-Gly, Fmoc-Ala, Fmoc-Ala, Fmoc-Arg (Pbf), Fmoc-Gly, Fmoc-Val, Fmoc-Thr (Bu$^t$), Fmoc-His (Trt), Fmoc-Tyr (Bu$^t$), Fmoc-Arg (Pbf), Fmoc-Pro, Fmoc-Ser (Bu$^t$), Fmoc-Ala, Fmoc-Val, Fmoc-His (Trt), Fmoc-Lys (Boc), Fmoc-Tyr (Bu$^t$) and Fmoc-Trp (Boc) to obtain 830 mg of Fmoc-Trp (Boc)-Tyr (Bu$^t$)-Lys (Boc)-His (Trt)-Val-Ala-Ser (Bu$^t$)-Pro-Arg (Pbf)-Tyr (Bu$^t$)-His (Trt)-Thr (Bu$^t$)-Val-Gly-Arg (Pbf)-Ala-Ala-Gly-Leu-Leu-Met-Gly-Leu-O-Clt resin. To 150 mg of this resin, 5 ml of TFA/thioanisole/m-cresol/triisopropylsilane/ethanedithiol (85/5/5/2.5/2/5) was added. After the mixture was shaken at room temperature for 2 hours, the resin was filtered off and the solvent was concentrated. Ether was added to the concentrate to obtain crude Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu as precipitates. The crude product was subjected to linear density gradient elution (60 mins.) using solution A: 0.1% TFA-water and solution B: 0.1% TFA-containing acetonitrile in A/B: 72/28 to 52/48 on preparatory HPLC using YMC D-ODS-5-ST S-5 120A column (20×150 mm). Fractions containing the product were collected and lyophilized to obtain 9.7 mg of white powders.

Mass spectrum (M+H)$^+$ 2805.7 (calcd. 2805.4)

Elution time on HPLC 25.1 mins.

Conditions for Elution:

Column: Wakosil-II 5C18 HG (4.6×100 mm)

Eluant: linear density gradient elution using solution A: 0.1% TFA-water and solution B: acetonitrile containing 0.1% TFA, with solutions A/B=100/0 to 30/70 (35 mins.)

Flow rate: 1.0 ml/min.

To 5 mg of the thus obtained Fmoc-Trp-Tyr-Lys-His-Val-Ala-Ser-Pro-Arg-Tyr-His-Thr-Val-Gly-Arg-Ala-Ala-Gly-Leu-Leu-Met-Gly-Leu, 1 mL of 20% diethylamine/DMF was added, and the mixture was stirred at room temperature for 2 hours. After the solvent was removed by distillation, the residue was subjected to linear density gradient elution (60 mins.) with solution A: 0.1% TFA-water and solution B: 0.1% TFA-containing acetonitrile in A/B: 74/26 to 64/36 on preparatory HPLC using YMC D-ODS-5-ST S-5 120A column (20×150 mm). Fractions containing the product were collected and lyophilized to obtain 1.2 mg of white powders.

Mass spectrum (M+H)$^+$ 2583.6 (calcd. 2583.4)

Elution time on HPLC 20.4 mins.

Conditions for elution:

Column: Wakosil-II 5C18 HG (4.6×100 mm)

Eluant: linear density gradient elution using solution A: 0.1% TFA-water and solution B: acetonitrile containing 0.1% TFA, with solutions A/B=100/0 to 30/70 (35 mins.)

Flow rate: 1.0 ml/min.

Example 13

Production of Human GPR8 Ligand (1–30): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu-Trp (SEQ ID NO: 17)

Using as a starting material 0.25 mmol (0.64 mmol/g) of Fmoc-Trp(Boc)-O-Clt resin obtained by introducing Fmoc-Trp(Boc) into commercially available 2-chlorotrityl resin (Clt resin, 1.33 mmol/g), amino acids were condensed in their sequence order as in EXAMPLE 12, and the Fmoc group was removed on the resin after introducing the final Trp and before excising from the resin. By treatment with TFA/thioanisole/m-cresol/triisopropylsilane/ethanedithiol (85/5/5/2.5/2.5), excision from the resin and removal of side chain protective groups were effected at the same time. The crude peptide was purified as in EXAMPLE 12 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu-Trp.

Mass spectrum (M+H)$^+$ 3543.4 (calcd. 3544.2)

Elution time on HPLC 21.5 mins.

Conditions for elution:

Column: Wakosil-II 5C18 HG (4.6×100 mm)

Eluant: linear density gradient elution using solution A: 0.1% TFA-water and solution B: acetonitrile containing 0.1% TFA, with solutions A/B=100/0 to 30/70 (35 mins.)

Flow rate: 1.0 ml/min.

Example 14

Production of Human GPR8 Ligand (1–29):

```
Trp-Tyr-Lys-His-Val-Ala-Ser-Pro-   (SEQ ID NO: 20)
Arg-Tyr-His-Thr-Val-Gly-Arg-Ala-
Ala-Gly-Leu-Leu-Met-Gly-Leu-Arg-
Arg-Ser-Pro-Tyr-Leu
```

Using the resin of EXAMPLE 12, amino acids were condensed in the order of their sequences as in EXAMPLE 13, and excision from the resin and purification were performed to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr-Leu.

Example 15

Production of Human GPR8 Ligand (1–28):

```
Trp-Tyr-Lys-His-Val-Ala-Ser-Pro-   (SEQ ID NO: 21)
Arg-Tyr-His-Thr-Val-Gly-Arg-Ala-
Ala-Gly-Leu-Leu-Met-Gly-Leu-Arg-
Arg-Ser-Pro-Tyr
```

After Fmoc-Tyr (Bu$^t$) was introduced into commercially available 2-chlorotrityl resin (Clt resin, 1.33 mmol/g), condensation of amino acids in their sequence order, excision from the resin and purification were carried out as in EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro-Tyr.

Example 16

Production of Human GPR8 Ligand (1–27):

```
Trp-Tyr-Lys-His-Val-Ala-Ser-Pro-   (SEQ ID NO: 22)
Arg-Tyr-His-Thr-Val-Gly-Arg-Ala-
Ala-Gly-Leu-Leu-Met-Gly-Leu-Arg-
Arg-Ser-Pro
```

After Fmoc-Pro was introduced into commercially available 2-chlorotrityl resin (Clt resin, 1.33 mmol/g), condensation of amino acids in their sequence order, excision from the resin and purification were carried out as in EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser-Pro.

Example 17

Production of Human GPR8 Ligand (1–26): Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser (SEQ ID NO: 23)

After Fmoc-Tyr (Bu$^t$) was introduced into commercially available 2-chlorotrityl resin (Clt resin, 1.33 mmol/g), condensation of amino acids in their sequence order, excision from the resin and purification were carried out as in EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg-Ser.

Example 18

Production of Human GPR8 Ligand (1–25):

Trp-Tyr-Lys-His-Val-Ala-Ser-Pro- (SEQ ID NO: 24)

Arg-Tyr-His-Thr-Val-Gly-Arg-Ala-

Ala-Gly-Leu-Leu-Met-Gly-Leu-Arg-

Arg

After Fmoc-Arg (Pbf) was introduced into commercially available 2-chlorotrityl resin (Clt resin, 1.33 mmol/g), condensation of amino acids in their sequence order, excision from the resin and purification were carried out as in EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg-Arg.

Example 19

Production of Human GPR8 Ligand (1–24):

Trp-Tyr-Lys-His-Val-Ala-Ser-Pro- (SEQ ID NO: 25)

Arg-Tyr-His-Thr-Val-Gly-Arg-Ala-

Ala-Gly-Leu-Leu-Met-Gly-Leu-Arg

After Fmoc-Arg (Pbf) was introduced into commercially available 2-chlorotrityl resin (Clt resin, 1.33 mmol/g), condensation of amino acids in their sequence order, excision from the resin and purification were carried out as in EXAMPLE 13 to obtain Trp-Tyr-Lys-His-Val-Ala-Ser-Pro-Arg-Tyr-His-Thr-Val-Gly-Arg-Ala-Ala-Gly-Leu-Leu-Met-Gly-Leu-Arg.

Example 20

Figure 3:
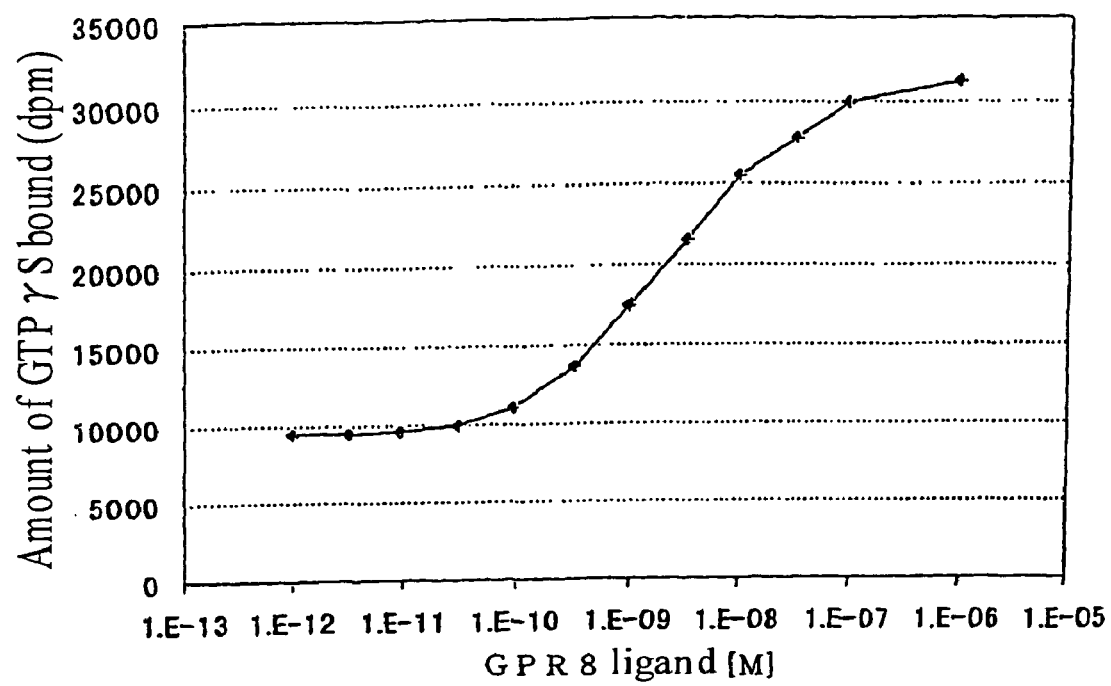
FIG. 3 shows the GTPγ S binding promoting activity of a human homologue GPR8 ligand peptide composed of 23 residues in various concentrations on the CHO/GPR8 cell membrane fraction.

GTPγ S Binding Promoting Activity of Human Homologue of the GPR8 Ligand Peptide Composed of 23 Residues when Measured Using GPR8-expressed CHO Cell Membrane Fraction The human homologue of GPR8 ligand peptide composed of 23 residues, which was synthesized in EXAMPLE 12 (hereinafter sometimes referred to as hGPR8L (1–23)) was added to the GPR8-expressed CHO cell membrane fraction in various concentrations according to the procedures described in EXAMPLE 6 to assay the GTPγ S binding promoting activity. The results are shown in FIG. 3. Obviously, hGPR8L (1–23) dose-dependently promoted the GTPγ S binding of GPR8-expressed CHO cell membrane fraction. The results revealed that the peptide having a structure of SEQ ID NO:16 is a ligand to GPR8.

Example 21

Figure 4:
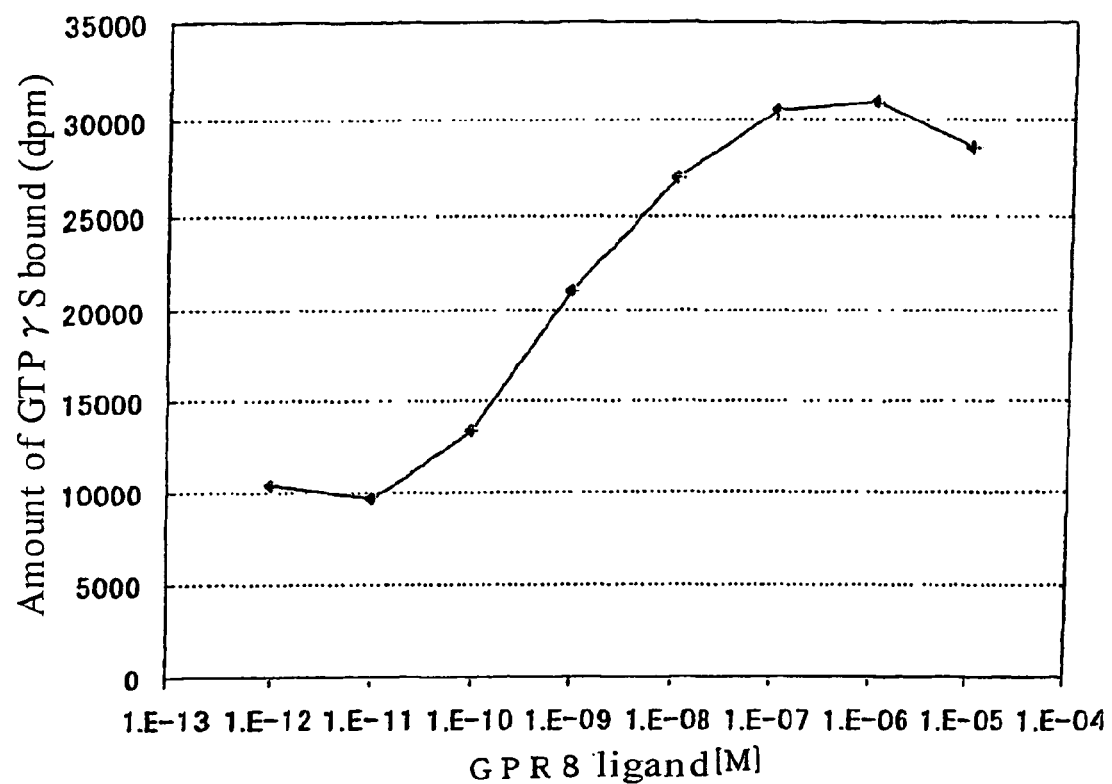
FIG. 4 shows the GTPγ S binding promoting activity of a human homologue GPR8 ligand peptide composed of 30 residues in various concentrations on the CHO/GPR8 cell membrane fraction.

GTPγ S Binding Promoting Activity of Human Homologue of the GPR8 Ligand Peptide Composed of 30 Residues when Measured Using GPR8-expressed CHO Cell Membrane Fraction The human homologue of GPR8 ligand peptide composed of 30 residues, which was synthesized in EXAMPLE 13 (hereinafter sometimes referred to as hGPR8L (1–30)) was added to the GPR8-expressed CHO cell membrane fraction in various concentrations according to the procedures described in EXAMPLE 6 to assay the GTPγ S binding promoting activity. The results are shown in FIG. 4. Obviously, hGPR8L (1–30) dose-dependently promoted the GTPγ S binding of GPR8-expressed CHO cell membrane fraction. The results revealed that the peptide having a structure of SEQ ID NO:17 is a ligand to GPR8.

Example 22

Figure 5:
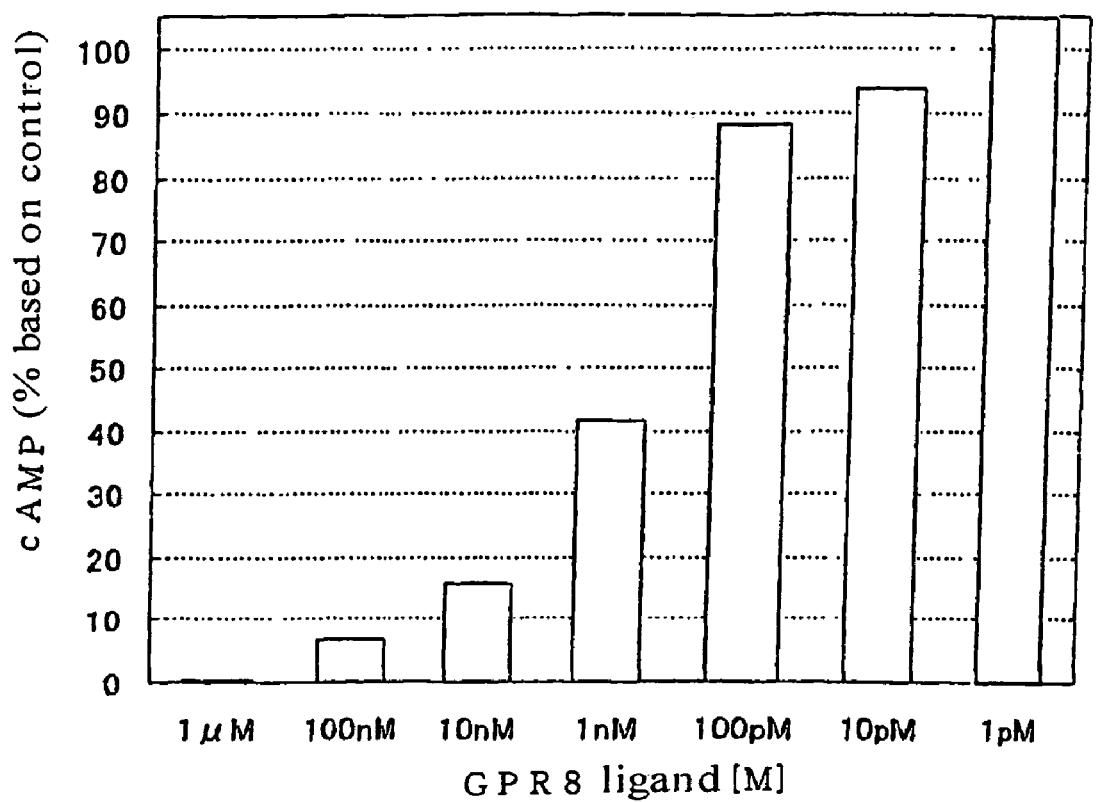
FIG. 5 shows the cAMP production suppressing activity of GPR8 ligand peptide composed of 23 residues in various concentrations on human homologue CHO/GPR8 cells.

Intracellular cAMP Production Suppressing Activity of Human Homologue of the GPR8 Ligand Peptide Composed of 23 Residues when Measured Using GPR8-expressed CHO Cells hGPR8L (1–23), which was synthesized in EXAMPLE 12, was brought in contact with the GPR8-expressed CHO cells in various concentrations according to the procedures described in EXAMPLE 5, to assay the intracellular cAMP production suppressing activity. The results are shown in FIG. 5. Obviously, hGPR8L (1–23) dose-dependently suppressed the intracellular cAMP production to the GPR8-expressed CHO cells. In the figure, the cAMP synthesis suppressing activity is expressed by the value in terms of %, which is obtained when the intracellular cAMP level added with a reaction buffer is subtracted from the intracellular cAMP level when hGPR8L (1–23) is added, wherein the intracellular cAMP level obtained by subtracting the intracellular cAMP level added with a reaction buffer from the intracellular cAMP level added with a forskolin-containing reaction buffer is made 100%.

Example 23

Figure 7:
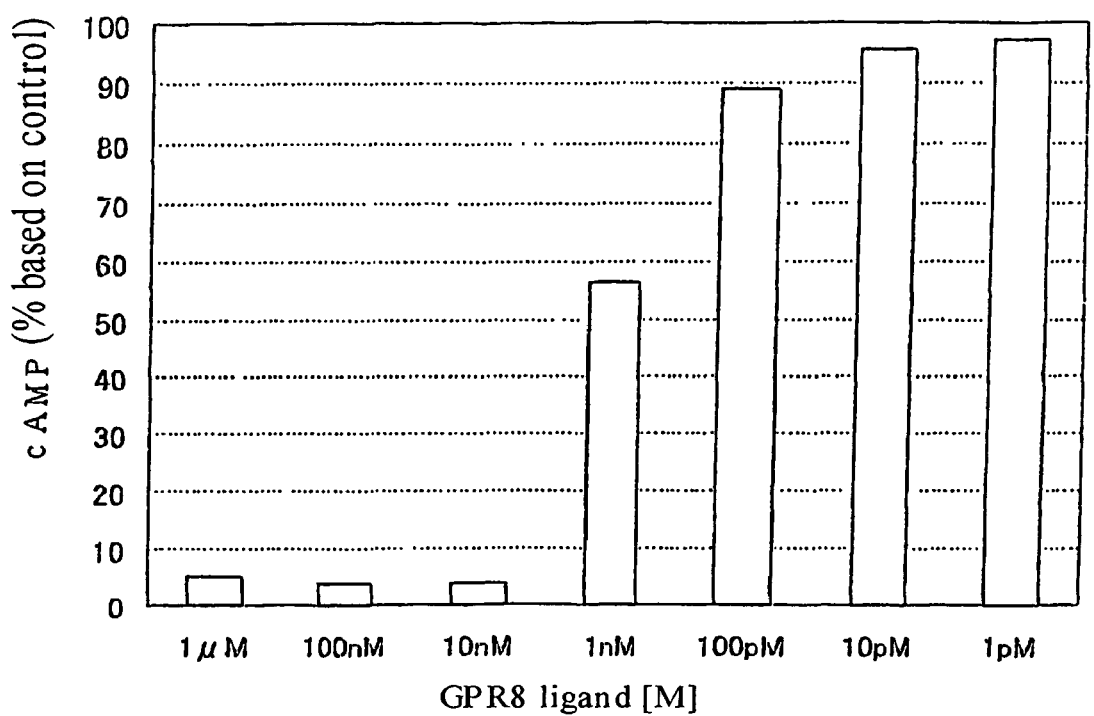
FIG. 7 shows the cAMP production suppressing activity of GPR8 ligand peptide composed of 30 residues in various concentrations on human homologue CHO/GPR8 cells.

Intracellular cAMP Production Suppressing Activity of Human Homologue of the GPR8 Ligand Peptide Composed of 30 Residues when Measured Using GPR8-expressed CHO Cells hGPR8L (1–30), which was synthesized in EXAMPLE 13, was brought in contact with the GPR8-expressed CHO cells in various concentrations according to the procedures described in EXAMPLE 5, to assay the intracellular cAMP production suppressing activity. The results are shown in FIG. 7. Obviously, hGPR8L (1–30) dose-dependently suppressed the intracellular cAMP production to the GPR8-expressed CHO cells. In the figure, the cAMP synthesis suppressing activity is expressed by the value in terms of %, which is obtained when the intracellular cAMP level added with a reaction buffer is subtracted from the intracellular cAMP level when hGPR8L (1–30) is added, wherein the intracellular cAMP level obtained by subtracting the intra-cellular cAMP level added with a reaction buffer from the intracellular cAMP level added with a forskolin-containing reaction buffer is made 100%.

Example 24

Activity of GPR8 Ligand on Eating Behavior

Wistar male rats (9 weeks old) under pentobarbital anesthesia were inserted with a guide cannula (AG-8) targeted at the lateral ventricle (AP: 8.1, L: 1.8, H: 7.1 mm). Animals were allowed at least a week of recovery postoperatively before being used in the experiments. During the recovery period, animals were subjected to handling every day to minimize a stress caused by intracerebroventricular injection.

Figure 6:
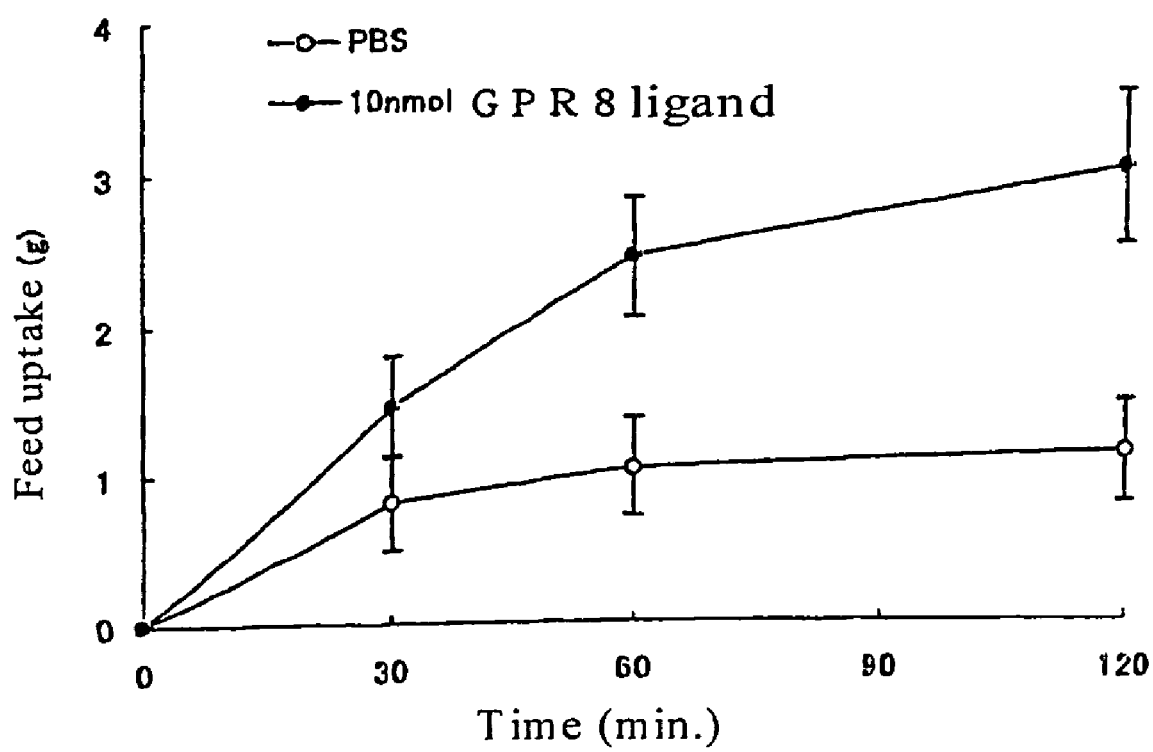
FIG. 6 shows the activity of GPR8 ligand peptide on food uptake, wherein each value is a mean value±SEM (n=10).

Feeding test commenced at 15:00. Rats were inserted with a microinjection cannula under unanesthesia and nonrestraint, and were given a PBS solution of the peptide (peptide composed of the amino acid sequence represented by SEQ ID NO: 16) obtained in EXAMPLE 12 or PBS alone in a dose of 5 µl/min for 2 minutes. The microinjection cannula was removed 1 minute after completion of the injection and animals were allowed to free access to pre-weighed feed (pellets CE2: Nippon Kurea). Time began to count from the time of injection and food intake was measured by weighing the pellets after 30, 60 and 120 minutes (FIG. 6).

Example 25

Cloning of 5' Upstream End of cDNA Encoding Human GPR8 Ligand Precursor Protein

5' RACE PCR was carried out to clarify the 5' upstream base sequence of cDNA encoding the human GPR8 ligand precursor protein, in which human hypothalamus cDNA was used as a template and a primer prepared based on the human cDNA sequence (SEQ ID NO:14) encoding a part of the precursor protein of a human homologue of the ligand peptide to GPR8 described in EXAMPLE 11 (hereinafter sometimes referred to as human GPR8 ligand) was used. The 5' RACE PCR cloning was effected by the following procedures: PCR was carried out by using human hypothalamic MARATHON-Ready cDNA (CLONTECH) as a template and using AP1 primer attached to the kit and the synthetic primer of SEQ ID NO: 33, and then using this PCR solution as a template, PCR was further carried out using AP2 primer attached to the kit and the synthetic primer of SEQ ID NO: 34. The compositions of reaction solutions and reaction conditions for PCR were as follows. The reaction solution was composed of 4 µl of human hypothalamic cDNA, 0.5 µM of AP1 primer, 0.5 µM of the synthetic DNA primer of SEQ ID NO: 33, 0.4 mM of dNTPs and 0.2 µl of LATaq polymerase (Takara Shuzo Co., Ltd.), with GC(I) buffer attached to the enzyme added to make the total reaction volume of 20 µl. Using Thermal Cycler (PE Biosystems), the reaction solution was, after heating at 96° C. for 120 seconds, subjected to 30 repetitions of one cycle set to include 96° C. for 30 seconds and 68° C. for 240 seconds, and finally kept at 72° C. for 10 minutes. Next, the PCR solution was diluted to 50-fold with Tricine-EDTA buffer attached to the kit. A 2 µl aliquot of the dilution, 0.5 µM of AP2 primer, 0.5 µM of the synthetic DNA primer of SEQ ID NO: 34, 0.4 mM of dNTPs and 0.2 µl of LATaq polymerase (Takara Shuzo Co., Ltd.), with GC (I) buffer attached to the enzyme added to make the total reaction volume of 20 µl. Using Thermal Cycler (PE Biosystems), the reaction solution was, after heating at 96° C. for 120 seconds, subjected to 4 repetitions of one cycle set to include 96° C. for 30 seconds and 72° C. for 180 seconds, 4 repetitions of one cycle set to include 96° C. for 30 seconds and 70° C. for 180 seconds, 17 repetitions of one cycle set to include 96° C. for 30 seconds and 68° C. for 180 seconds, and finally kept at 72° C. for 10 minutes. After the amplified DNA was isolated by 1.2% agarose gel electrophoresis, the DNA having a size of about 1200 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 35.

Example 26

Preparation of Human Brain cDNA

Human brain cDNA was prepared from human brain poly A (+) RNA (CLONTECH) using Marathon™ cDNA Amplification Kit (CLONTECH). cDNAs provided for RACE PCR were prepared in accordance with the protocol attached to the kit, except for synthesis of the 1st strand cDNA. The 1st strand cDNA was synthesized from 1 µg of human brain poly A (+) RNA using reverse transcriptase MMLV (−RNAse H) (RefTraAce, Toyobo Co., Ltd.) in place of reverse transcriptase AMV attached to the kit.

Example 27

Cloning of 3' Downstream End of cDNA Encoding Human GPR8 Ligand Precursor Protein 3' RACE PCR was carried out to clarify the 3' downstream base sequence of cDNA encoding the human GPR8 ligand, in which human brain cDNA was used as a template and a primer prepared based on the human cDNA sequence (SEQ ID NO: 14) encoding a part of the precursor protein of a human homologue of the ligand peptide to GPR8 described in EXAMPLE 11 was used. The 3' RACE PCR cloning was effected by the following procedures: PCR was carried out by using human brain cDNA as a template and using AP1 primer attached to the kit and the synthetic primer of SEQ ID NO: 36, and then using this PCR solution as a template, PCR was further carried out using AP2 primer attached to the kit and the synthetic primer of SEQ ID NO: 37. The compositions of reaction solutions and reaction conditions for PCR were as follows. The reaction solution was composed of 1 µl of human brain cDNA diluted to 50-fold with Tricine-EDTA Buffer attached to the kit, 0.5 µM of AP1 primer, 0.5 µM of the synthetic DNA primer of SEQ ID NO: 36, 0.4 mM of dNTPs and 0.2 µl of LATaq polymerase (Takara Shuzo Co., Ltd.), with GC (I) buffer attached to the enzyme added to make the total reaction volume of 20 µl. Using Thermal Cycler (PE Biosystems), the reaction solution was, after heating at 96° C. for 120 seconds, subjected to 30 repetitions of one cycle set to include 96° C. for 30 seconds and 68° C. for 240 seconds, and finally kept at 72° C. for 10 minutes. Next, the PCR solution was diluted to 50-fold with Tricine-EDTA buffer attached to the kit. A 1 µl aliquot of the diluted PCR solution, 0.5 µM of AP2 primer, 0.5 µM of the synthetic DNA primer of SEQ ID NO: 37, 0.4 mM of dNTPs and 0.2 µl of LATaq polymerase (Takara Shuzo Co., Ltd.), with GC (I) buffer attached to the enzyme added to make the total reaction volume of 20 µl. Using Thermal Cycler (PE Biosystems), the reaction solution was, after heating at 96° C. for 120 seconds, subjected to 4 repetitions of one cycle set to include 96° C. for 30 seconds and 72° C. for 180 seconds, 4 repetitions of one cycle set to include 96° C. for 30 seconds and 70° C. for 180 seconds, 17 repetitions of one cycle set to include 96° C. for 30 seconds and 68° C. for 180 seconds, and finally kept at 72° C. for 10 minutes. After the amplified DNA was isolated by 1.5% agarose gel electrophoresis, the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 38.

Example 28

Cloning of cDNA Encoding Human GPR8 Ligand Precursor Protein

Amplification was carried out by PCR to effect the cloning of cDNA encoding the human GPR8 ligand precursor protein, in which human hypothalamus cDNA was used as a template and a primer prepared based on the 5' upstream base sequence of cDNA encoding human GPR8 ligand precursor protein and a primer prepared based on the 3' downstream base sequence of cDNA encoding the human GPR8 ligand precursor protein was used. The compositions of reaction solutions and reaction conditions for PCR were as follows. The reaction solution was composed of 1 µl of human hypothalamus Marathon-Ready cDNA (CLONTECH), 0.5 µM of the synthetic DNA primer of SEQ ID NO: 39, 0.5 µM of the synthetic DNA primer of SEQ ID NO: 40, 0.4 mM of dNTPs, 2.5 mM of MgCl₂, 5% DMSO and 0.2 µl of LATaq polymerase (Takara Shuzo Co., Ltd.), with the buffer attached to the enzyme added to make the total reaction volume of 20 µl. Using Thermal Cycler (PE Biosystems), the reaction solution was, after heating at 96° C. for 60 seconds, subjected to 35 repetitions of one cycle set to include 96° C. for 30 seconds, 64° C. for 30 seconds and 72° C. for 120 seconds, and finally kept at 72° C. for 10 minutes. After the amplified DNA was isolated by 1.5% agarose gel electrophoresis, the DNA having a size of about 700 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 41.

Since this sequence (SEQ ID NO: 41) encodes human GPR8 ligand precursor protein, *Escherichia coli* transformed by plasmid bearing this DNA was named TOP10/pCR2.1-TOPO Human GPR8 Ligand Precursor.

In the DNA sequence represented by SEQ ID NO: 41, such a frame as encoding the amino acid sequence of human GPR8 ligand peptide described in EXAMPLE 11 is present, but the 5' upstream side has no ATG supposed to be an initiation codon of protein translation. However, there are some examples reported so far that codons other than ATG are assumed to act as initiation codon in some proteins (human basic fibroblast growth factor (H. Prats et al., Proc. Natl. Acad. Sci. USA, 86, 1836–1840, 1989; R. Z. Florkiewicz and A. Sommer, Proc. Natl. Acad. Sci. USA, 86, 3978–3981, 1989), mouse retinoic acid receptor β4 (S. Nagpal et al., Proc. Natl. Acad. Sci. USA, 89, 2718, 1992), human phosphoribosylpyrophosphate synthase (M. Taira et al., J. Biol. Chem., 265, 16491–16497, 1990), *drosophila* choline acetltransferase (H. Sugihara et al., J. Biol. Chem., 265, 21714–21719, 1990)).

In these reports, Leu-encoding CTG is frequently predicted to serve as an initiation codon in place of ATG, and such will also apply to human GPR8 ligand precursor protein. Based on comparison with the precursor protein of porcine or rat GPR8 ligand homologue later described, it was thus assumed that a CTG codon present at the position almost corresponding to ATG, supposed to serve as an initiation codon in these precursor proteins, would be read as an initiation codon, and a sequence of the precursor protein was predicted. The amino acid sequence of this hypothetical human GPR8 ligand precursor protein is shown by SEQ ID NO: 42. Also, the amino acid sequence and DNA sequence of hypothetical human GPR8 ligand precursor protein are shown in FIG. 8.

Example 29

Preparation of Porcine Spinal Cord cDNA

Porcine spinal cord cDNA was prepared from porcine spinal cord poly A (+) RNA (CLONTECH) using Marathon™ cDNA Amplification Kit (CLONTECH). Porcine spinal cord poly A (+) RNA was prepared from porcine spinal cord as follows. Porcine spinal cord was fully homogenized in ISOGEN (Nippon Gene) with a Polytron homogenizer. From the homogenate, porcine spinal cord total RNA was acquired in accordance with the total RNA preparation method using ISOGEN solution. Next, chromatography was performed twice using oligo dT cellulose column attached to mRNA Purification Kit (Amersham Pharmacia Biotech) to acquire 7 µg of porcine spinal cord poly A (+) RNA. The cDNAs provided for RACE PCR were prepared in accordance with the protocol attached to the kit, except for synthesis of the 1st strand cDNA. The 1st strand cDNA was synthesized from 1 μg of porcine spinal cord poly A (+) RNA using reverse transcriptase MMLV (−RNAse H) (RefTraAce, Toyobo Co., Ltd.) in place of reverse transcriptase AMV attached to the kit.

Example 30

Cloning of 5' Upstream End of cDNA Encoding Porcine GPR8 Ligand Precursor Protein The first 5' RACE PCR followed by the second 5' RACE PCR using a base sequence of the DNA amplified by the first PCR revealed the 5' upstream base sequence of cDNA encoding the precursor protein of a porcine homologue of the GPR8 ligand peptide (hereinafter sometimes referred to as porcine GPR8 ligand).

The first 5' RACE PCR cloning was attained by the following procedures. PCR was carried out, in which the aforesaid porcine spinal cord cDNA was used as a template and AP1 primer attached to the kit and the synthetic primer of SEQ ID NO: 43 were used, which was followed by PCR using this PCR solution as a template and further using AP2 primer attached to the kit and the synthetic primer of SEQ ID NO: 44. The compositions of reaction solutions and reaction conditions for PCR were as follows. The reaction solution was composed of 4 μl of porcine spinal cord cDNA diluted to 50-fold with Tricine-EDTA Buffer attached to the kit, 0.5 μM of AP1 primer, 0.5 μM of the synthetic DNA primer of SEQ ID NO: 43, 0.4 mM of dNTPs and 0.2 μl of LATaq polymerase (Takara Shuzo Co., Ltd.), with GC (I) buffer attached to the enzyme added to make the total reaction volume of 20 μl. Using Thermal Cycler (PE Biosystems), the reaction solution was, after heating at 96° C. for 120 seconds, subjected to 30 repetitions of one cycle set to include 96° C. for 30 seconds and 68° C. for 180 seconds, and finally kept at 72° C. for 10 minutes. Next, 1 μl of the PCR solution diluted to 100-fold with Tricine-EDTA buffer attached to the kit, 0.5 μM of AP2 primer, 0.5 μM of the synthetic DNA primer of SEQ ID NO: 44, 0.4 mM of dNTPs and 0.2 μl of Advantage-GC 2 polymerase (CLONTECH), with the buffer attached to the enzyme added to make the total reaction volume of 20 μl. Using Thermal Cycler (PE Biosystems), the reaction solution was, after heating at 96° C. for 60 seconds, subjected to 3 repetitions of one cycle set to include 96° C. for 30 seconds and 72° C. for 180 seconds, 3 repetitions of one cycle set to include 96° C. for 30 seconds and 70° C. for 180 seconds, then 4 repetitions of one cycle set to include 96° C. for 30 seconds and 68° C. for 180 seconds, and then 15 repetitions of one cycle set to include 96° C. for 30 seconds, 64° C. for 30 seconds and 72° C. for 180 seconds, and finally kept at 72° C. for 10 minutes. The amplified DNA was isolated by 1.2% agarose gel electrophoresis, and the DNA having a size of about 300 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin, IPTG and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 45.

The second 5' RACE PCR cloning was effected by the following procedures. Using the porcine spinal cord cDNA as a template, PCR was carried out using AP1 primer attached to the kit and the synthetic primer of SEQ ID NO: 46, followed by PCR using this PCR solution as a template and further using AP2 primer attached to the kit and the synthetic primer of SEQ ID NO: 47. The compositions of reaction solutions and reaction conditions for PCR were as follows. The reaction solution was composed of 1 μl of porcine spinal cord cDNA diluted to 50-fold with Tricine-EDTA Buffer attached to the kit, 0.5 μM of AP1 primer, 0.5 μM of the synthetic DNA primer of SEQ ID NO: 46, 0.4 mM of dNTPs and 0.2 μl of Advantage-GC 2 polymerase (CLONTECH), with GC (1) buffer attached to the enzyme added to make the total reaction volume of 20 μl. Using Thermal Cycler (PE Biosystems), the reaction solution was, after heating at 96° C. for 60 seconds, subjected to 5 repetitions of one cycle set to include 96° C. for 30 seconds and 72° C. for 180 seconds, 5 repetions of one cycle set to include 96° C. for 30 seconds and 70° C. for 180 seconds, 20 repetitions of one cycle set to include 96° C. for 30 seconds and 68° C. for 180 seconds, and finally kept at 72° C. for 10 minutes. Next, 1 μl of the PCR solution diluted to 100-fold with Tricine-EDTA buffer attached to the kit, 0.5 μM of AP2 primer, 0.5 μM of the synthetic DNA primer of SEQ ID NO: 47, 0.4 mM of dNTPs and 0.2 μl of Advantage-GC 2 polymerase (CLONTECH), with the buffer attached to the enzyme added to make the total reaction volume of 20 μl. Using Thermal Cycler (PE Biosystems), the reaction solution was, after heating at 96° C. for 60 seconds, subjected to 31 repetitions of one cycle set to include 96° C. for 30 seconds and 68° C. for 180 seconds, and finally kept at 72° C. for 10 minutes. The amplified DNA was isolated by 2.0% agarose gel electrophoresis, and the DNA having a size of about 200 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin, IPTG and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 48.

Example 31

Cloning of 3' Downstream End of cDNA Encoding Porcine GPR8 Ligand Precursor Protein The 3' downstream base sequence of cDNA encoding the precursor protein of porcine GPR8 ligand peptide was clarified by 3' RACE PCR cloning using a primer prepared based on the 5' upstream base sequence of cDNA encoding the porcine GPR8 ligand precursor protein. The 3' RACE PCR cloning was achieved by carrying out PCR using porcine spinal cord cDNA as a template and further using AP1 primer attached to the kit and the synthetic primer of SEQ ID NO: 49, followed by PCR using the resulting PCR solution as a template and further using AP2 primer attached to the kit and the synthetic primer of SEQ ID NO: 50. The compositions of reaction solutions and reaction conditions for PCR were as follows. The reaction solution composed of 1 µl of porcine spinal cord cDNA diluted to 50-fold with Tricine-EDTA Buffer attached to the kit, 0.5 µM of AP1 primer, 0.5 µM of the synthetic DNA primer of SEQ ID NO: 49, 0.4 mM of dNTPs and 0.2 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 60 seconds, subjected to 5 repetitions of one cycle set to include 96° C. for 30 seconds and 72° C. for 120 seconds, 5 repetitions of one cycle set to include 96° C. for 30 seconds and 70° C. for 120 seconds, then 20 repetitions of one cycle set to include 96° C. for 30 seconds and 68° C. for 120 seconds, and finally kept at 72° C. for 10 minutes. Next, the reaction solution composed of 1 µl of the PCR solution diluted to 100-fold with Tricine-EDTA Buffer attached to the kit, 0.5 µM of AP2 primer, 0.5 µM of the synthetic DNA primer of SEQ ID NO: 50, 0.4 mM of dNTPs and 0.2 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 120 seconds, subjected to 31 repetitions of one cycle set to include 96° C. for 30 seconds and 68° C. for 120 seconds, and finally kept at 72° C. for 10 minutes. After the amplified DNA was isolated by 2.0% agarose gel electrophoresis, the DNA having a size of about 650 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin, X-gal and IPTG. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 51.

Example 32

Cloning of cDNA Encoding Porcine GPR8 Ligand Precursor Protein

A cDNA encoding the porcine GPR8 ligand precursor protein was cloned by PCR amplification with a primer prepared based on the 5' upstream base sequence of cDNA encoding the porcine GPR8 ligand precursor protein, in which porcine spinal cord cDNA was used as a template. The compositions of reaction solutions and reaction conditions for PCR were as follows. The reaction solution was composed of 1 µl of porcine spinal cord cDNA diluted to 50-fold with Tricine-EDTA Buffer attached to the kit, 0.5 µM of the synthetic DNA primer of SEQ ID NO: 52, 0.5 µM of the synthetic DNA primer of SEQ ID NO: 53, 0.4 mM of dNTPs, 0.2 µl of Advantage 2 polymerase (CLONTECH), with the buffer attached to the enzyme added to make the total reaction volume of 20 µl. Using Thermal Cycler (PE Biosystems), the reaction solution was, after heating at 96° C. for 60 seconds, subjected to 4 repetitions of one cycle set to include 96° C. for 30 seconds and 72° C. for 75 seconds, 4 repetitions of one cycle set to include 96° C. for 30 seconds and 70° C. for 75 seconds, then 4 repetitions of one cycle set to include 96° C. for 30 seconds and 68° C. for 75 seconds, next 5 repetitions of one cycle set to include 96° C. for 30 seconds, 64° C. for 30 second and 72° C. for 45 seconds, then 20 repetitions of one cycle set to include 96° C. for 30 seconds, 60° C. for 30 second and 72° C. for 45 seconds, and finally kept at 72° C. for 10 minutes. The amplified DNA was isolated by 1.2% agarose gel electrophoresis, and the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 54. Since this sequence (SEQ ID NO: 54) encodes porcine GPR8 ligand precursor protein, *Escherichia coli* transformed by a plasmid bearing this DNA was named TOP10/pCR2.1-TOPO Porcine GPR8 Ligand Precursor.

The amino acid sequence for porcine GPR8 ligand precursor encoded by the DNA sequence of SEQ ID NO: 54 is shown by SEQ ID NO: 55. In the amino acid sequence of this precursor protein, there was present a sequence up to 17 residues from the N terminus, which was clarified by amino acid sequencing of the GPR8 ligand peptide isolated from porcine hypothalamus using as an indicator the GTPγ S binding activity to the GPR8-expressed cell membrane fraction described in EXAMPLE 10. In addition, the Arg-Arg sequence (Seidah, N. G. et al., Ann. N.Y. Acad. Sci., 839, 9–24, 1998) was present at 2 sites in the carboxy terminal side of that sequence, from which sequence a normal physiologically active peptide was considered to be excised, as in the human homologue precursor protein of GPR8 ligand peptide. In view of the foregoing, it was deduced that the amino acid sequence of a porcine homologue of the GPR8 ligand peptide would be either SEQ ID NO: 56 or 57 or both. FIG. 9 shows the amino acid sequence and DNA sequence of porcine GPR8 ligand precursor protein.

Example 33

Cloning of cDNA Fragment Encoding a Part of Rat GPR8 Ligand Precursor Protein

As described in EXAMPLE 10, database survey was made based on the sequence of 17 amino acids from the N terminus (SEQ ID NO: 6) of the peptide purified from porcine hypothalamus using as an indicator the GTPγ S binding activity on the GPR8-expressed cell membrane fraction. Thus, rat EST base sequence (Accession No. H31598), which coincided with the base sequence of SEQ ID NO: 11, was found. The DNA sequence had a translation frame, in which the sequence of 15 amino acids was identical with the amino acid sequence (SEQ ID NO: 6) for the peptide purified from porcine hypothalamus. This H31598 is an EST sequence derived from cDNA library prepared from rat PC12 cells, and is composed of 260 bases including unidentified 7 bases. Since this H31598 was assumed to encode a part of the precursor protein of a rat homologue peptide of GPR8 ligand (hereinafter sometimes referred to as rat GPR8 ligand), in order to determine its accurate base sequence, PCR cloning was carried out on the respective primers prepared based on the 5' base sequence and 3' base sequence of H31598 using rat brain Marathon-Ready cDNA (CLONTECH) as a template. The compositions of reaction solutions and reaction conditions for PCR were as follows. The reaction solution composed of 2 μl of rat brain Marathon cDNA (CLONTECH), 0.5 μM of the synthetic DNA primer of SEQ ID NO: 60, 0.5 μM of the synthetic DNA primer of SEQ ID NO: 61, 0.4 mM of dNTPs and 0.2 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 60 seconds, subjected to 35 repetitions of one cycle set to include 96° C. for 30 seconds, 60° C. for 30 seconds and 72° C. for 60 seconds, and finally kept at 72° C. for 10 minutes. The amplified DNA was isolated by 4.0% agarose gel electrophoresis, and the DNA having a size of about 250 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium-containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 62. Comparison between the base sequence (SEQ ID NO: 62) of the PCR-cloned DNA and the base sequence of H31589 revealed that there was a reading error of one base deletion in the base sequence of H31589.

Example 34

Cloning of 5' Upstream End of cDNA Encoding Rat GPR8 Ligand Precursor Protein

The 5' upstream base sequence of cDNA encoding the rat GPR8 ligand precursor protein was clarified by 5' RACE PCR cloning. The 5' RACE PCR cloning was effected by carrying out PCR using AP1 primer attached to the kit and the synthetic primer of SEQ ID NO: 63, in which rat brain Marathon-Ready cDNA (CLONTECH) was used as a template, followed by PCR using AP2 primer attached to the kit and the synthetic primer of SEQ ID NO: 64, in which the resulting PCR solution was used as a template. The compositions of reaction solutions and reaction conditions for PCR were as follows. The reaction solution composed of 2 μl of rat brain Marathon cDNA (CLONTECH), 0.5 μM of AP1 primer, 0.5 μM of the synthetic DNA primer of SEQ ID NO: 63, 0.4 mM of dNTPs and 0.2 μl of LATaq polymerase (Takara Shuzo Co., Ltd.) was made the total reaction volume of 20 μl, with addition of GC (I) buffer attached to the enzyme. Using Thermal Cycler (PE Biosystems), the reaction solution was, after heating at 96° C. for 60 seconds, subjected to 30 repetitions of one cycle set to include 96° C. for 30 seconds and 68° C. for 120 seconds, and finally kept at 72° C. for 10 minutes. Next, the reaction solution composed of 2 μl of the PCR solution diluted to 200-fold with Tricine-EDTA Buffer attached to the kit, 0.5 μM of AP2 primer, 0.5 μM of the synthetic DNA primer of SEQ ID NO: 64, 0.4 mM of dNTPs and 0.2 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 60 seconds, subjected to 31 repetitions of one cycle set to include 96° C. for 30 seconds and 68° C. for 120 seconds, and finally kept at 72° C. for 10 minutes. The amplified DNA was isolated by 1.2% agarose gel electrophoresis, and the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 65.

Example 35

Cloning of 3' Downstream End of cDNA Encoding Rat GPR8 Ligand Precursor Protein

The 3' downstream base sequence of cDNA encoding rat GPR8 ligand precursor protein was clarified by 3' RACE PCR cloning using a primer prepared based on the 5' upstream terminal base sequence of cDNA encoding the rat GPR8 ligand precursor protein and a primer prepared based on the cDNA fragment sequence encoding a part of the rat GPR8 ligand precursor protein. The 3' RACE PCR cloning was effected by carrying out PCR using AP1 primer attached to the kit and the synthetic primer of SEQ ID NO: 66, in which rat brain Marathon-Ready cDNA (CLONTECH) was used as a template, followed by PCR using AP2 primer attached to the kit and the synthetic primer of SEQ ID NO: 67, in which the resulting PCR solution was used as a template. The compositions of reaction solutions and reaction conditions for PCR were as follows. The reaction solution composed of 2 μl of rat brain Marathon-Ready cDNA (CLONTECH), 0.5 μM of AP1 primer, 0.5 μM of the synthetic DNA primer of SEQ ID NO: 66, 0.4 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 60 seconds, subjected to 30 repetitions of one cycle set to include 96° C. for 30 seconds and 68° C. for 180 seconds, and finally kept at 72° C. for 10 minutes. Next, the reaction solution composed of 2 µl of the PCR solution diluted to 200-fold with Tricine-EDTA Buffer attached to the kit, 0.5 µM of AP2 primer, 0.5 µM of the synthetic DNA primer of SEQ ID NO: 67, 0.4 mM of dNTPs and 0.4 µl of Advantage-GC 2 polymerase (CLONTECH) was made the total reaction volume of 20 µl, with addition of the buffer attached to the enzyme. Using Thermal Cycler (PE Biosystems), the reaction solution was, after heating at 96° C. for 60 seconds, subjected to 30 repetitions of one cycle set to include 96° C. for 30 seconds and 68° C. for 180 seconds, and finally kept at 72° C. for 10 minutes. The amplified DNA was isolated by 1.2% agarose gel electrophoresis, and the DNA having a size of about 600 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to Escherichia coli TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 68.

Example 36

Cloning of cDNA Encoding Rat GPR8 Ligand Precursor Protein

A cDNA encoding the rat GPR8 ligand precursor protein was cloned by PCR amplification with a primer prepared based on the 5' upstream base sequence of cDNA encoding the rat GPR8 ligand precursor protein and a primer prepared based on the 3' downstream base sequence of cDNA encoding the rat GPR8 ligand precursor protein, in which rat brain cDNA was used as a template. The compositions of reaction solutions and reaction conditions for PCR were as follows. The reaction solution was composed of 1 µl of rat brain Marathon-Ready cDNA, 0.5 µM of the synthetic DNA primer of SEQ ID NO: 69, 0.5 µM of the synthetic DNA primer of SEQ ID NO: 70, 0.4 mM of dNTPs and 0.4 µl of Advantage 2 polymerase (CLONTECH), with the buffer attached to the enzyme added to make the total reaction volume of 20 µl. Using Thermal Cycler (PE Biosystems), the reaction solution was, after heating at 96° C. for 60 seconds, subjected to 35 repetitions of one cycle set to include 96° C. for 30 seconds, 60° C. for 30 seconds and 72° C. for 60 seconds, and finally kept at 72° C. for 10 minutes. The amplified DNA was isolated by 1.2% agarose gel electrophoresis, and the DNA having a size of about 750 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to Escherichia coli TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 71. Since this sequence (SEQ ID NO: 71) encodes the rat GPR8 ligand precursor protein, Escherichia coli transformed by a plasmid bearing this DNA was named TOP10/pCR2.1-TOPO Rat GPR8 Ligand Precursor.

The amino acid sequence for rat GPR8 ligand precursor encoded by the DNA sequence of SEQ ID NO: 71 is shown by SEQ ID NO: 72. In the amino acid sequence of this precursor protein, there was present a similar sequence that is different only in the 5th and 17th amino acids from the sequence up to 17 residues from the N terminus, which was clarified by amino acid sequencing of the GPR8 ligand peptide isolated from porcine hypothalamus using as an indicator the GTPγ S binding activity to the GPR8-expressed cell membrane fraction described in EXAMPLE 10. In addition, the Arg-Arg sequence (Seidah, N. G. et al., Ann. N.Y. Acad. Sci., 839, 9–24, 1998) was present at 2 sites in the carboxy terminal side of that sequence, from which sequence a normal physiologically active peptide was considered to be excised, as in the human or porcine homologue precursor protein of GPR8 ligand peptide. In view of the foregoing, it was deduced that the amino acid sequence of a rat homologue of the GPR8 ligand peptide would be either SEQ ID NO: 73 or 74 or both. FIG. 10 shows the amino acid sequence and DNA sequence of rat GPR8 ligand precursor protein.

Example 37

Cloning of cDNA Fragment Encoding a Part of Mouse GPR8 Ligand Precursor Protein

Database survey was conducted based on the base sequence encoding porcine GPR8 ligand peptide of 23 amino acid residues represented by SEQ ID NO: 58. As a result of mouse genome database of Celera Genomics, the mouse genome fragment sequence of SEQ ID NO: 77 containing a base sequence similar to the base sequence of SEQ ID NO: 58 was discovered. It was predicted that this sequence would be a genome fragment sequence encoding a part of the precursor protein of a mouse homologue of the GPR8 ligand peptide (hereinafter sometimes referred to as mouse GPR8 ligand). The compositions of reaction solutions and reaction conditions for PCR were as follows. One microliter of mouse testis cDNA (CLONTECH), 0.5 µM of the synthetic DNA primer of SEQ ID NO: 78, 0.5 µM of the synthetic DNA primer of SEQ ID NO:79, 0.4 mM of dNTPs and 0.2 µl of LATaq polymerase (Takara Shuzo Co., Ltd.) was made the total reaction volume of 20 µl, with addition of GC (I) buffer attached to the enzyme. Using Thermal Cycler (PE Biosystems), the reaction solution was, after heating at 96° C. for 120 seconds, subjected to 10 repetitions of one cycle set to include 96° C. for 30 seconds and 68° C. for 120 seconds, 25 repetitions of one cycle set to include 96° C. for 30 seconds, 64° C. for 30 seconds and 72° C. for 120 seconds, and finally kept at 72° C. for 10 minutes. The amplified DNA was isolated by 1.5% agarose gel electrophoresis, and the DNA having a size of about 350 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer (SEQ ID NO: 80). The base sequence of cDNA acquired herein by the PCR cloning was fully coincident with the mouse genome fragment base sequence inserted between the 2 base sequences used for the primers of SEQ ID NO: 78 and SEQ ID NO: 79.

Example 38

Preparation of Mouse Brain cDNA

Mouse brain cDNA was prepared from mouse brain poly A (+) RNA (CLONTECH) using SMART™ RACE cDNA Amplification Kit (CLONTECH) in accordance with the protocol attached to the kit. A solution of the 1st strand cDNA synthesized was diluted to 10-fold with Tricine-EDTA Buffer attached to the kit. The solution was used for RACE PCR.

Example 39

Cloning of 5' Upstream End of cDNA Encoding Mouse GPR8 Ligand Precursor Protein

The 5' upstream base sequence of cDNA encoding the mouse GPR8 ligand precursor protein was clarified by 5' RACE PCR cloning. The 5' RACE PCR cloning was effected by PCR using Universal Primer Mix attached to SMART™ RACE cDNA Amplification Kit and the synthetic primer of SEQ ID NO: 81, in which mouse brain cDNA was used as a template, followed by PCR using Nested Universal Primer attached to the kit and the synthetic primer of SEQ ID NO: 82, in which the resulting PCR solution was used as a template. The compositions of reaction solutions and reaction conditions for PCR were as follows. The reaction solution composed of 1 μl of mouse brain cDNA, 2 μl of Universal Primer Mix, 0.2 μM of the synthetic DNA primer of SEQ ID NO: 81, 0.8 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds and 68° C. for 120 seconds, and finally kept at 72° C. for 10 minutes. Next, the reaction solution composed of 0.5 μl of the PCR solution diluted to 50-fold with Tricine-EDTA Buffer attached to the kit, 0.5 μM of Nested Universal Primer, 0.5 μM of the synthetic DNA primer of SEQ ID NO: 82, 0.8 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds, 60° C. for 30 seconds and 72° C. for 120 seconds, and finally kept at 72° C. for 10 minutes. The amplified DNA was isolated by 1.5% agarose gel electrophoresis, and the DNA having a size of about 300 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 83.

Example 40

Cloning of 3' Downstream End of cDNA Encoding Mouse GPR8 Ligand Precursor Protein The 3' downstream base sequence of cDNA encoding the mouse GPR8 ligand precursor protein was clarified by 3' RACE PCR cloning. The 3' RACE PCR cloning was effected by PCR using Universal Primer Mix attached to SMART™ RACE cDNA Amplification Kit and the synthetic primer of SEQ ID NO: 84, in which mouse brain cDNA was used as a template, followed by PCR using Nested Universal Primer attached to the kit and the synthetic primer of SEQ ID NO: 85, in which the resulting PCR solution was used as a template. The compositions of reaction solutions and reaction conditions for PCR were as follows. The reaction solution composed of 1 μl of mouse brain cDNA, 2 μl of Universal Primer Mix, 0.5 μM of the synthetic DNA primer of SEQ ID NO: 84, 0.8 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds and 68° C. for 120 seconds, and finally kept at 72° C. for 10 minutes. Next, the reaction solution composed of 0.5 μl of the PCR solution diluted to 50-fold with Tricine-EDTA Buffer attached to the kit, 0.5 μM of Nested Universal Primer, 0.5 μM of the synthetic DNA primer of SEQ ID NO: 85, 0.8 mM of dNTPs and 0.4 μl of Advantage-GC 2 polymerase (CLONTECH) was made the total reaction volume of 20 μl, with addition of the buffer attached to the enzyme. Using Thermal Cycler (PE Biosystems), the reaction solution was, after heating at 96° C. for 120 seconds, subjected to 30 repetitions of one cycle set to include 96° C. for 30 seconds, 64° C. for 30 seconds and 72° C. for 120 seconds, and finally kept at 72° C. for 10 minutes. The amplified DNA was isolated by 1.5% agarose gel electrophoresis, and the DNA having a size of about 700 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 86.

Example 41

Cloning of cDNA Encoding Mouse GPR8 Ligand Precursor Protein

A cDNA encoding the mouse GPR8 ligand precursor protein was cloned by PCR amplification with a primer prepared based on the 5' upstream base sequence of cDNA encoding the mouse GPR8 ligand precursor protein and a primer prepared based on the 3' downstream base sequence of cDNA encoding the mouse GPR8 ligand precursor protein, in which mouse brain cDNA was used as a template. The compositions of reaction solutions and reaction conditions for PCR were as follows. The reaction solution was composed of 0.5 µl of mouse brain cDNA, 0.5 µM of the synthetic DNA primer of SEQ ID NO: 87, 0.5 µM of the synthetic DNA primer of SEQ ID NO: 88, 1.6 mM of dNTPs and 0.2 µl of LATaq polymerase (Takara Shuzo Co., Ltd.), with the buffer attached to the enzyme added to make the total reaction volume of 20 µl. Using Thermal Cycler (PE Biosystems), the reaction solution was, after heating at 96° C. for 120 seconds, subjected to 40 repetitions of one cycle set to include 96° C. for 30 seconds, 64° C. for 30 seconds and 72° C. for 120 seconds, and finally kept at 72° C. for 10 minutes. The amplified DNA was isolated by 1.5% agarose gel electrophoresis, and the DNA having a size of about 700 bp was excised with a razor blade and recovered using QIAquick Gel Extraction Kit (Qiagen). The recovered DNA was subcloned into vector PCR2.1-TOPO according to the protocol of TOPO TA Cloning Kit (Invitrogen), which was then transfected to *Escherichia coli* TOP10 competent cell (Invitrogen) for transfection. The resulting clones bearing the cDNA insert fragment were selected in an LB medium containing ampicillin and X-gal. Only clones exhibiting white color were picked with a sterilized toothpick to acquire transformants. The individual clones were cultured overnight in an LB culture medium containing ampicillin, and plasmid DNAs were prepared using QIAwell 8 Plasmid Kit (Qiagen). The reaction for base sequencing was carried out using BigDye Terminator Cycle Sequencing Ready Reaction Kit (PE Biosystems), and the DNAs were decoded by using a fluorescent automatic sequencer to acquire the DNA sequence represented by SEQ ID NO: 89. Since this sequence (SEQ ID NO: 89) encodes the mouse GPR8 ligand precursor protein, *Escherichia coli* transformed by a plasmid bearing this DNA was named TOP10/pCR2.1-TOPO Mouse GPR8 Ligand Precursor.

In the amino acid sequence of the DNA sequence represented by SEQ ID NO: 89, there is such a frame as encoding a similar amino acid sequence that is different only in the 5th and 17th amino acids from the sequence up to 17 residues from the N terminus, which was clarified by amino acid sequencing of the GPR8 ligand peptide isolated from porcine hypothalamus using as an indicator the GTPγ S binding activity to the GPR8-expressed cell membrane fraction described in EXAMPLE 10. As in the human GPR8 ligand precursor, however, no ATG supposed to serve as an initiation codon of protein translation does not exist at the 5' upstream side. However, as predicted in the human GPR8 ligand precursor protein, based on comparison with the precursor protein of porcine or rat GPR8 ligand homologue, it was assumed that a CTG codon present at the position almost corresponding to ATG, which is supposed to serve as an initiation codon in these precursor proteins, would be read as an initiation codon, and a sequence of the mouse GPR8 ligand precursor protein was predicted. The amino acid sequence of this hypothetical mouse GPR8 ligand precursor protein is shown by SEQ ID NO: 90. As in the case of human, porcine or rat homologue precursor protein of the GPR8 ligand peptide, the Arg-Arg sequence (Seidah, N. G. et al., Ann. N.Y. Acad. Sci., 839, 9–24, 1998) was present at 2 sites in the carboxy terminal side of the sequence supposed to be an amino acid sequence of the mouse GPR8 ligand, from which a normal physiologically active peptide was considered to be excised. In view of the foregoing, it was deduced that the amino acid sequence of a mouse homologue of the GPR8 ligand peptide would be either SEQ ID NO: 91 or 92 or both. The amino acid sequence for mouse GPR8 ligand of 23 residues represented by SEQ ID NO: 91 coincided with the amino acid sequence (SEQ ID NO: 73) for rat GPR8 ligand of 23 residues. FIG. 11 shows the amino acid sequence and DNA sequence of hypothetical mouse GPR8 ligand precursor protein.

Example 42

Preparation of [$^{125}$I-Tyr$^2$]-hGPR8L (1–23) and [$^{125}$I-Tyr$^{10}$]-hGPR8L (1–23)

A solution of 1 nmol hGPR8L (1–23) in 5 µl of DMSO was mixed with 5 µl of 0.1 M nickel chloride. After the solution was mixed with 10 µl of 0.001% hydrogen peroxide aqueous solution in 0.1 M HEPES (pH 7), 10 µl of a 10 µl/ml lactoperoxidase (Sigma, Inc.) solution in 0.1 M HEPES (pH 7) and 10 µl of [$^{125}$I] NaI 37 MBq (NEW LIFE SCIENCE PRODUCTS, LTD.), the mixture was reacted at room temperature for 60 minutes and fractionated by HPLC under the following conditions.

A column used was ODS-80™ (4.6 mm×15 cm) (TOSO Co., Ltd.), and using 10% acetonitrile/0/1% TFA and 60% acetonitrile/0.1% TFA as eluants A and B, respectively, gradient elution was performed in 0–0% (2 mins.), 0–30% (3 mins.) and 30–38% (5 mins.), 38–43% (55 mins.) of eluant B/eluants A+B. The flow rate was 1 mL/min, the column temperature was 25° C., and detection was made at absorbance of 220 nm.

Since 2 tyrosine residues are present in hGPR8L (1–23), [$^{125}$I-Tyr$^2$]-hGPR8L (1–23) and [$^{125}$I-Tyr$^{10}$]-hGPR8L (1–23) are produced by iodation. Under the HPLC conditions, hGPR8L (1–23), [$^{125}$I-Tyr$^2$]-hGPR8L (1–23) and [$^{125}$I-Tyr$^{10}$]-hGPR8L (1–23) were eluted at about 24 mins., 30 mins. and 32 mins., respectively.

Example 43

Receptor Binding Test Using [$^{125}$I-Tyr$^{10}$]-hGPR8L (1–23)

Receptor binding test was carried out using [$^{125}$I]-labeled hGPR8L (1–23) prepared as described in EXAMPLE 42 and the cell membrane fraction prepared from GPR8-expressed CHO cells prepared in a similar manner to the procedures described in EXAMPLE 6.

Figure 12:
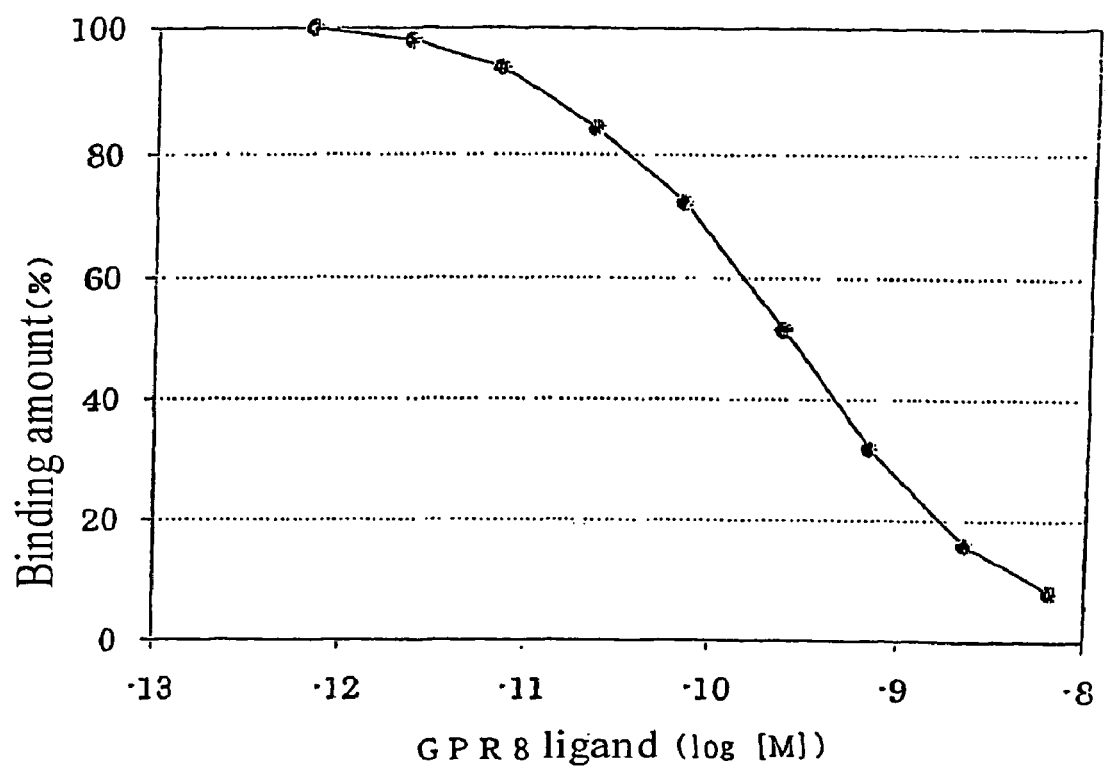
FIG. 12 is a graph showing the binding inhibition activity of human GPR8 ligand of 23 residues on [$^{125}$I]-labeled human GPR8 ligand of 23 residues, using a cell membrane fraction prepared from human GPR8-expressed CHO cells.

The cell membrane fraction prepared from human GPR8-expressed CHO cells was diluted with an assay buffer (25 mM Tris-HCl, 5 mM EDTA (ethylenediaminetetraacetic acid), 0.05% CHAPS (3-[(3-cholamidopropyl)dimethlammonio]-1-propanesulfonate), 0.1% BSA (bovine serum albumin), 0.25 mM PMSF (phenylmethylsulfonyl fluoride), 1 µg/ml pepstatin, 20 µg/ml leupeptin, pH 7.4) in various concentrations. Subsequently, 200 µl each of the dilution was dispensed in a polypropylene tst tube (Falcon 2053). To assay for the total binding (TB), 2 µl of DMSO and 2 µl of 7 nM [$^{125}$I-Tyr$^2$]-hGPR8L (1–23) or [$^{125}$I-Tyr$^{10}$]-hGPR8L (1–23) were added to the membrane fraction solution. Also, to assay for non-specific binding (NSB), 2 µl of a 100 µM hGPR8L (1–23) solution in DMSO and 2 µl of 7 nM [$^{125}$I-Tyr$^2$]-hGPR8L (1–23) or [$^{125}$I-Tyr$^{10}$]-hGPR8L (1–23) were added to the membrane fraction solution. After reacting at 25° C. for 60 minutes, the reaction solution was suction-filtrated through a polyethyleneimine-treated Whatman glass filter (GF-F). After filtration, the residual radioactivity remained on the filter paper was measured with a γ-counter, and the specific binding (SB) was estimated by subtracting the non-specific binding from the total binding. Since the specific binding obtained by using [$^{125}$I-Tyr$^{10}$]-hGPR8L (1–23) was higher by twice than the case of using [$^{125}$I-Tyr$^2$]-hGPR8L (1–23), [$^{125}$I-Tyr$^{10}$]-hGPR8L (1–23) was used in the actual test. When the concentration of membrane fraction was varied, the specific binding of [$^{125}$I-Tyr$^{10}$]-hGPR8L (1–23) was noted dependently on the concentration of membrane fraction. Also, by setting the membrane fraction concentration at 5 µg/ml, 50% inhibitory concentration (IC$_{50}$ value) of hGPR8L (1–23) was calculated from the inhibition rate (%). The IC$_{50}$ value was found to be 0.25 nM. FIG. 12 shows the binding inhibition of hGPR8L (1–23) in various concentrations.

Example 44

Production of Oxidized Human GPR8 Ligand (1–23):

Trp-Tyr-Lys-His-Val-Ala-Ser-Pro-  (SEQ ID NO: 95)
Arg-Tyr-His-Thr-Val-Gly-Arg-Ala-
Ala-Gly-Leu-Leu-Met(O)-Gly-Leu

In 0.5 ml of 50% aqueous acetic acid solution, 0.45 mg of the compound of EXAMPLE 12 was dissolved. Then 0.05 ml of 0.3% hydrogen peroxide aqueous solution was added to the solution, and the mixture was allowed to stand at room temperature for 8 hours. After concentrating in vacuum, the concentrate was purified on SepPark to obtain 0.443 mg of white powders.

Mass spectrum (M+H)$^+$: 2599.2 (calcd. 2599.4)
Elution time on HPLC: 19.1 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 45

Production of Human GPR8 Ligand (1–22):

Trp-Tyr-Lys-His-Val-Ala-Ser-Pro-  (SEQ ID NO: 96)
Arg-Tyr-His-Thr-Val-Gly-Arg-Ala-
Ala-Gly-Leu-Leu-Met-Gly

Fmoc-Gly was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Example 46

Production of Human GPR8 Ligand (1–21):

Trp-Tyr-Lys-His-Val-Ala-Ser-Pro-  (SEQ ID NO: 97)
Arg-Tyr-His-Thr-Val-Gly-Arg-Ala-
Ala-Gly-Leu-Leu-Met

Fmoc-Met was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Example 47

Production of Human GPR8 Ligand (1–20):

Trp-Tyr-Lys-His-Val-Ala-Ser-Pro-  (SEQ ID NO: 98)
Arg-Tyr-His-Thr-Val-Gly-Arg-Ala-
Ala-Gly-Leu-Leu

Fmoc-Leu was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Mass spectrum (M+H)$^+$: 2282.8 (calcd. 2282.6)
Elution time on HPLC: 17.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 48

Production of Human GPR8 Ligand (1–19):

Trp-Tyr-Lys-His-Val-Ala-Ser-Pro-  (SEQ ID NO: 99)
Arg-Tyr-His-Thr-Val-Gly-Arg-Ala-
Ala-Gly-Leu

Fmoc-Leu was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Mass spectrum (M+H)$^+$: 2169.6 (calcd. 2169.5)
Elution time on HPLC: 16.4 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 0/70 (35 mins.)
Flow rate: 1.0 ml/min.

Example 49

Production of Human GPR8 Ligand (1–18):

Trp-Tyr-Lys-His-Val-Ala-Ser-Pro-  (SEQ ID NO: 100)
Arg-Tyr-His-Thr-Val-Gly-Arg-Ala-
Ala-Gly

Fmoc-Gly was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Mass spectrum (M+H)$^+$: 2056.8 (calcd. 2056.3)
Elution time on HPLC: 14.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 50

Production of Human GPR8 Ligand (1–17):

Trp-Tyr-Lys-His-Val-Ala-Ser-Pro-  (SEQ ID NO: 101)
Arg-Tyr-His-Thr-Val-Gly-Arg-Ala-
Ala

Fmoc-Leu was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Example 51

Production of Human GPR8 Ligand (1–16):

Trp-Tyr-Lys-His-Val-Ala-Ser-Pro-  (SEQ ID NO: 102)
Arg-Tyr-His-Thr-Val-Gly-Arg-Ala

Fmoc-Leu was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Example 52

Production of Porcine GPR8 Ligand (1–23):

Trp-Tyr-Lys-His-Thr-Ala-Ser-Pro-  (SEQ ID NO: 56)
Arg-Tyr-His-Thr-Val-Gly-Arg-Ala-
Ala-Gly-Leu-Leu-Met-Gly-Leu

Fmoc-Leu was introduced into commercially available 2-chlorotrityl resin (Clt resin, 1.33 mmol/g). Then, condensation of amino acids in the order of sequence, excision from the resin and purification were performed as in EXAMPLE 13 to obtain the product.

Mass spectrum (M+H)$^+$: 2585.2 (calcd. 2585.4)
Elution time on HPLC: 20.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 mil/min.

Example 53

Production of Rat/Mouse GPR8 Ligand (1–23):

Trp-Tyr-Lys-His-Val-Ala-Ser-Pro-  (SEQ ID NO: 73 and
                                    SEQ ID NO: 91)
Arg-Tyr-His-Thr-Val-Gly-Arg-Ala-
Ser-Gly-Leu-Leu-Met-Gly-Leu The condensation of amino acids in the order of sequence, excision from the resin and purification were performed as in EXAMPLE 52 to obtain the product.

Example 54

Production of Oxidized Porcine GPR8 Ligand (1–23):

Trp-Tyr-Lys-His-Thr-Ala-Ser-Pro-  (SEQ ID NO: 103)
Arg-Tyr-His-Thr-Val-Gly-Arg-Ala-
Ala-Gly-Leu-Leu-Met(O)-Gly-Leu

The compound of EXAMPLE 52 was oxidized as in EXAMPLE 44 to obtain the product.

Mass spectrum (M+H)$^+$: 2601.3 (calcd. 2601.4)
Elution time on HPLC: 18.9 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 55

Production of Oxidized Rat/Mouse GPR8 Ligand (1–23):

```
Trp-Tyr-Lys-His-Val-Ala-Ser-Pro-    (SEQ ID NO: 104)
Arg-Tyr-His-Thr-Val-Gly-Arg-Ala-
Ser-Gly-Leu-Leu-Met(O)-Gly-Leu
```

The compound of EXAMPLE 53 was oxidized as in EXAMPLE 44 to obtain the product.

Example 56

Production of [$N^\alpha$-Acetyl-Trp$^1$]-Human GPR8 Ligand (1–23):

```
Ac-Trp-Tyr-Lys-His-Val-Ala-Ser-    (SEQ ID NO: 106)
Pro-Arg-Tyr-His-Thr-Val-Gly-Arg-
Ala-Ala-Gly-Leu-Leu-Met-Gly-Leu
```

From the resin prepared in EXAMPLE 12, Fmoc group was removed. After acetylating with acetic anhydride, the acetylated product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to EXAMPLE 12 to obtain the product.

Mass spectrum (M+H)$^+$: 2626. 12625.8 (calcd. 2627. 12626.1)
Elution time on HPLC: 21.4 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 57

Production of Human GPR8 Ligand (2–23):

```
Tyr-Lys-His-Val-Ala-Ser-Pro-Arg-    (SEQ ID NO: 107)
Tyr-His-Thr-Val-Gly-Arg-Ala-Ala-
Gly-Leu-Leu-Met-Gly-Leu
```

As in EXAMPLE 12, a desired amino acid sequence was introduced into the resin. After introducing the final Tyr and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to EXAMPLE 12 to obtain the product.

Mass spectrum (M+H)$^+$: 2397.1 (calcd. 2397.3)
Elution time on HPLC: 19.9 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 58

Production of Human GPR8 Ligand (4–23):

```
His-Val-Ala-Ser-Pro-Arg-Tyr-His-    (SEQ ID NO: 108)
Thr-Val-Gly-Arg-Ala-Ala-Gly-Leu-
Leu-Met-Gly-Leu
```

As in EXAMPLE 12, a desired amino acid sequence was introduced into the resin. After introducing the final His and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to EXAMPLE 12 to obtain the product.

Mass spectrum (M+H)$^+$: 2106.0 (calcd. 2106.1)
Elution time on HPLC: 20.0 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 59

Production of Human GPR8 Ligand (9–23):

```
Arg-Tyr-His-Thr-Val-Gly-Arg-Ala-    (SEQ ID NO: 109)
Ala-Gly-Leu-Leu-Met-Gly-Leu
```

As in EXAMPLE 12, a desired amino acid sequence was introduced into the resin. After introducing the final Arg and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to EXAMPLE 12 to obtain the product.

Mass spectrum (M+H)$^+$: 1615.0 (calcd. 1614.9)
Elution time on HPLC: 20.2 mins.
Conditions for elution:
Column: Wakosil-II 5C18 HG (4.6×100 mm)
Eluant: linear density gradient elution using eluant A: 0.1% TFA-water and eluant B: acetonitrile containing 0.1% TFA, with A/B=100/0 to 30/70 (35 mins.)
Flow rate: 1.0 ml/min.

Example 60

Production of Human GPR8 Ligand (15–23): Arg-Ala-Ala-Gly-Leu-Leu-Met-Gly-Leu (SEQ ID NO:110)

As in EXAMPLE 12, a desired amino acid sequence was introduced into the resin. After introducing the final Arg and before excising from the resin, the Fmoc group was removed on the resin. Then, the Fmoc-removed product was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to EXAMPLE 12 to obtain the product.

Mass spectrum (M+H)$^+$: 901.4 (calcd. 901.5)

Elution time on HPLC: 20.2 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Example 61

Production of [N-Acetyl-Tyr$^2$]-Human GPR8 Ligand (2–23):

Ac-Tyr-Lys-His-Val-Ala-Ser-Pro- (SEQ ID NO: 111)
Arg-Tyr-His-Thr-Val-Gly-Arg-Ala-
Ala-Gly-Leu-Leu-Met-Gly-Leu

After acetylating the resin prepared in EXAMPLE 57 with acetic anhydride, the acetylated product was treated and purified as in EXAMPLE 57 to obtain the product.

Mass spectrum (M+H)$^+$: 2439.3 (calcd. 2439.3)

Elution time on HPLC: 20.2 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Example 62

Production of [D-Trp$^1$]-Human GPR8 Ligand (1–23):

D-Trp-Tyr-Lys-His-Val-Ala-Ser-Pro- (SEQ ID NO: 112)
Arg-Tyr-His-Thr-Val-Gly-Arg-Ala-
Ala-Gly-Leu-Leu-Met-Gly-Leu

The product was obtained in a manner similar to EXAMPLE 12, using Fmoc-D-Trp (Boc) in place of Fmoc-Trp (Boc).

Mass spectrum (M+H)$^+$: 2583.4 (calcd. 2583.4)

Elution time on HPLC: 20.6 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Example 63

Production of [N-3-Indolepropanyl-Tyr 2]-Human GPR8 Ligand (2–23):

3-Indolepropanoyl-Tyr-Lys-His-Val- (SEQ ID NO: 113)
Ala-Ser-Pro-Arg-Tyr-His-Thr-Val-
Gly-Arg-Ala-Ala-Gly-Leu-Leu-Met-
Gly-Leu Using 3-indolepropionic acid in place of Fmoc-Trp (Boc) in EXAMPLE 12, a desired resin was prepared. The resin was treated with TFA/thioanisole/m-cresol/triisopropylsilane/ethanedithiol (85/5/5/2.5/2.5) to effect excision from the resin and removal of the side chain protecting groups at the same time. The crude peptide was purified in a manner similar to EXAMPLE 12 to obtain the product.

Mass spectrum (M+H)$^+$: 2568.4 (calcd. 2568.4)

Elution time on HPLC: 21.7 mins.

Conditions for elution:

Column: Wakosil-II 5C18 HG (4.6×100 mm)

Eluant: linear density gradient elution using eluant A: 0.1% TFA-water and eluant B: acetonitrile containing 0.1% TFA, with A/B=100/0 to 30/70 (35 mins.)

Flow rate: 1.0 ml/min.

Example 64

GTPγ S Binding Promoting Activity of Human and Porcine Homologue Derivatives of the GPR8 Ligand Peptide Measured Using GPR8-Expressed Cell Membrane Fraction The human and porcine homologue derivatives of the GPR8 ligand peptide, which synthesis was described in the specification, were added to the GPR8-expressed cell membrane fraction in various concentrations by the procedures described in EXAMPLE 6 to determine the GTPγ S binding promoting activity. Sequence identification numbers of the derivatives tested and the GTPγ S binding promoting activity are shown in TABLE 1. The activity was expressed in terms of 50% effective concentration ($EC_{50}$). The GTPγ S binding promoting activities of hGPR8L (1–23) and hGPR8L (1–30) described in EXAMPLES 20 and 21 are also shown in the table.

Example 65

Receptor Binding Activity of Human and Porcine Homologue Derivatives of the GPR8 Ligand Peptide Measured Using GPR8-Expressed Cell Membrane Fraction and [$^{125}$I-Tyr$^{10}$]-hGPR8L (1–23)

The receptor binding activity of the human and porcine homologue derivatives of the GPR8 ligand peptide, which synthesis was described in the specification, was determined s described in EXAMPLE 43, using the GPR8-expressed cell membrane fraction and [$^{125}$I-Tyr$^{10}$]-hGPR8L (1–23). Sequence identification numbers of the derivatives tested and the receptor binding activity are shown in TABLE 1. The receptor binding activity was expressed in terms of 50% binding inhibition concentration ($IC_{50}$). The receptor binding activity of hGPR8L (1–23) described in EXAMPLE 43 is also shown in the table.

TABLE 1

GTPγ S binding promoting activity and receptor binding activity of human and porcine homologue derivatives of GPR8 ligand peptide

| Derivative | SEQ ID NO | GTPγ S binding promoting activity (EC$_{50}$ nM) | Receptor binding (IC$_{50}$ nM) |
|---|---|---|---|
| hGPR8L(1–23) | 16 | 1.6 | 0.25 |
| hGPR8L(1–30) | 17 | 0.57 | 0.025 |
| [Met(O)]-hGPR8L(1–23) | 95 | 1.4 | 0.31 |
| Fmoc-hGPR8L(1–23) | 105 | 240 | 0.20 |
| Ac-hGPR8L(1–23) | 106 | 14 | 2.4 |
| [D-Trp$^1$]-hGPR8L(1–23) | 112 | 7.1 | 0.82 |
| hGPR8L(2–23) | 107 | 3900 | 160 |
| Ac-hGPR8L(2–23) | 111 | 7200 | 420 |
| IndPr-hGPR8L(2–23) | 113 | 5.0 | 0.28 |
| hGPR8L(4–23) | 108 | 6700 | 1400 |
| hGPR8L(9–23) | 109 | 4200 | 1300 |
| hGPR8L(1–20) | 98 | 0.86 | 0.20 |
| hGPR8L(1–19) | 99 | 1000 | 100 |
| hGPR8L(1–18) | 100 | >10000 | 2700 |
| pGPR8L(1–23) | 56 | 1.5 | 0.38 |
| [Met(O)]-pGPR8L(1–23) | 103 | 0.73 | 0.29 |

Example 66

Prolactin Release Promoting Activity of GPR8 Ligand Peptide

Wistar male rats (9 weeks old) under pentobarbital anesthesia were inserted with a guide cannula (AG-12) targeted at the third ventricle (AP: −7.1, L: 0.0, H: 2.0 mm). Animals were allowed at least a week of recovery postoperatively before being used in the experiments. During the recovery period, animals were subjected to handling every day to minimize a stress caused by intracerebroventricular injection.

On the day before the experiments, rats under pentobarbital anesthesia were inserted with a cannula into the right jugular vein for blood collection. The test was performed between 9:00 and 12:00. Rats were inserted with a microinjection cannula under unanesthesia and nonrestraint, and were given a PBS solution of the human GPR8 ligand peptide (SEQ ID NO :16) (n=9) obtained in EXAMPLE 12 or PBS alone in a dose of 5 μl/min for 2 minutes. The microinjection cannula was removed 1 minute after completion of the injection and animals were allowed to move freely. Blood was collected by 300 μl each prior to the peptide injection and 5, 10, 20, 30 and 60 minutes after the start of injection. In order to keep the body water content constant, the equal volume of saline was given through the jugular vein after blood collection. The blood was heparinized and then centrifuged (5000 rpm×10 mins., 4° C. to isolate plasma. The prolactin level in plasma was assayed by radioimmunoassay using rat prolactin [$^{125}$I] assay system (Amersham Pharmacia Biotech).

Figure 13:
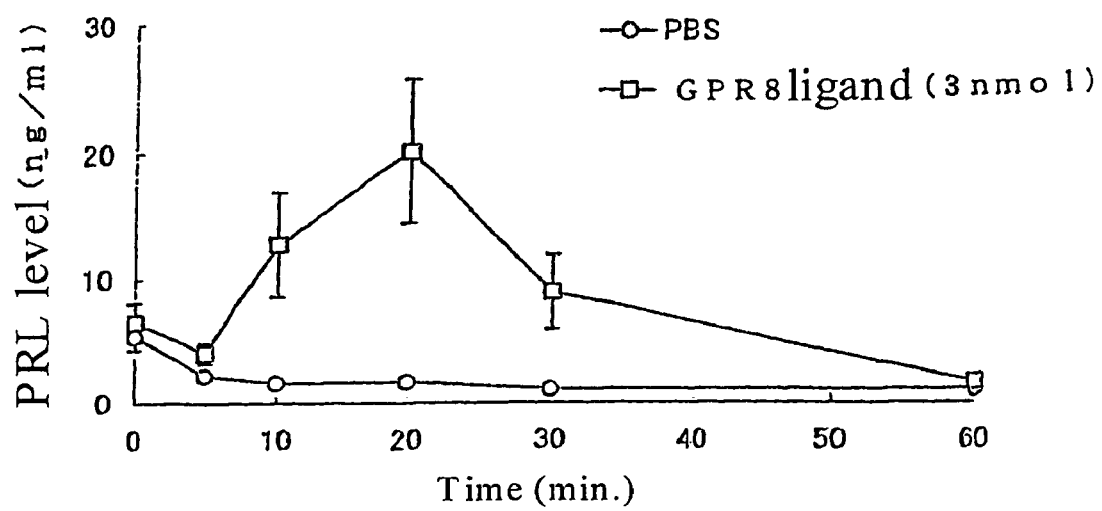
FIG. 13 is a graph showing an increase of prolactin level in blood by GPR8 ligand peptide in rats injected intraventricularly, wherein each value designates a mean±SEM.

The results are shown in FIG. 13. It is clearly demonstrated by the results that the GPR8 ligand peptide increased the blood prolactin level by intracerebroventricular injection.

INDUSTRIAL APPLICABILITY

The DNA of the present invention or the polypeptide of the present invention can be used for (1) survey of physiological activities possessed by the polypeptide of the present invention, (2) preparation of synthetic oligonucleotide probes or PCR primers, (3) acquisition of DNAs encoding ligands to GPR8 or precursor proteins, (4) development of the receptor-binding assay system using the expression system of recombinant receptor proteins and screening of candidate compounds for drugs, (5) acquisition of antibodies and antisera, (6) development of diagnostics using DNAs or antibodies, (7) development of pharmaceuticals such as central nervous function regulators, etc., (8) gene therapy, etc.

---

The invention claimed is:

1. An isolated polypeptide, or an amide or ester, or a salt thereof having an amino acid sequence selected from the group consisting of:
   (i) SEQ ID NO: 16,
   (ii) SEQ ID NO: 16 wherein from 1 to 3 terminal amino acids are deleted
   (iii) SEQ ID NO: 16 wherein from 1 to 5 terminal amino acids are added or
   (iv) SEQ ID NO: 16 wherein from 1 to 3 amino acids have been substituted;

and said polypeptide has a GTPγ S binding promoting activity on cells expressing a protein comprising the amino acid sequence of SEQ ID NO:4, or its amide or ester, or a salt thereof.

2. The polypeptide or its amide or ester, or a salt thereof, according to claim 1, which has an amino acid sequence selected from the group consisting of
   (i) SEQ ID NO:16;
   (ii) SEQ ID NO: 16 wherein from 1 to 3 amino acids are deleted from the carboxy terminal end,
   (iii) SEQ ID NO: 16 wherein 1 to 5 amino acids are added to the carboxy terminal end, or
   (iv) SEQ ID NO: 16 wherein Val at position 5 has been substituted.

3. The polypeptide or its amide or ester, or a salt thereof, according to claim 2, which comprises the amino acid sequence of SEQ ID NO:16.

4. A composition comprising the polypeptide or its amide or ester, or a salt thereof, according to claim 1.

5. A pharmaceutical composition comprising the polypeptide or its amide or ester, or a salt thereof, according to claim 1.

6. An appetite stimulant comprising the polypeptide or its amide or ester, or a salt thereof, according to claim 1.

7. A prolactin production promoting agent comprising the polypeptide or its amide or ester, or a salt thereof, according to claim 1.

8. A kit comprising the polypeptide or its amide or ester, or a salt thereof, according to claim 1.

9. A kit for screening according to claim 8, further comprising a protein comprising the amino acid sequence of SEQ ID NO:4 or its amide or ester, or a salt thereof.

* * * * *

UNITED STATES PATENT AND TRADEMARK OFFICE
CERTIFICATE OF CORRECTION

| | | |
|---|---|---|
| PATENT NO. | : 7,193,033 B2 | |
| APPLICATION NO. | : 10/311019 | |
| DATED | : March 20, 2007 | |
| INVENTOR(S) | : Masaaki Mori et al. | |

It is certified that error appears in the above-identified patent and that said Letters Patent is hereby corrected as shown below:

On the Title Page <u>please add</u> the following item 56 "Foreign Application Priority Data":

--Japanese Application No. 2000-191089, filed June 21, 2000

Japanese Application No. 2000-275013, filed September 6, 2000

Japanese Application No. 2001-116000, filed April 13, 2001--

Signed and Sealed this

Eleventh Day of September, 2007

JON W. DUDAS
*Director of the United States Patent and Trademark Office*

SEQUENCE LISTING

<160> NUMBER OF SEQ ID NOS: 125

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
atcgattaca atgcaggccg ctgggcaccc ag        32

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
actagtgccc ttcagcaccg caatatgctg cg        32

<210> SEQ ID NO 3

<211> LENGTH: 1023
<212> TYPE: DNA
<213> ORGANISM: Human

<400> SEQUENCE: 3

```
atcgattaca atgcaggccg ctgggcaccc agagcccctt gacagcaggg gctccttctc      60
cctccccacg atgggtgcca acgtctctca ggacaatggc actggccaca atgccacctt     120
ctccgagcca ctgccgttcc tctatgtgct cctgcccgcc gtgtactccg ggatctgtgc     180
tgtggggctg actggcaaca cggccgtcat ccttgtaatc ctaagggcgc caagatgaa      240
gacggtgacc aacgtgttca tcctgaacct ggccgtcgcc gacgggctct tcacgctggt     300
actgcccgtc aacatcgcgg agcacctgct gcagtactgg cccttcgggg agctgctctg     360
caagctggtg ctggccgtcg accactacaa catcttctcc agcatctact cctagccgt      420
gatgagcgtg gaccgatacc tggtggtgct ggccaccgtg aggtcccgcc acatgccctg     480
gcgcacctac cggggggcga aggtcgccag cctgtgtgtc tggctgggcg tcacggtcct     540
ggttctgccc ttcttctctt cgctggcgt ctacagcaac gagctgcagg tcccaagctg      600
tgggctgagc ttcccgtggc cgagcaggt ctggttcaag gccagccgtg tctacacgtt      660
ggtcctgggc ttcgtgctgc ccgtgtgcac catctgtgtg ctctacacag acctcctgcg     720
caggctgcgg gccgtgcggc tccgctctgg agccaaggct ctaggcaagg ccaggcggaa     780
ggtgaccgtc ctggtcctcg tcgtgctggc cgtgtgcctc ctctgctgga cgcccttcca     840
cctggcctct gtcgtggccc tgaccacgga cctgcccag acccccactgg tcatcagtat     900
gtcctacgtc atcaccagcc tcagctacgc caactcgtgc ctgaaccct tcctctacgc      960
ctttctagat gacaacttcc ggaagaactt ccgcagcata ttgcggtgct gaagggcact    1020
agt                                                                 1023
```

<210> SEQ ID NO 4
<211> LENGTH: 333
<212> TYPE: PRT
<213> ORGANISM: Human

<400> SEQUENCE: 4

```
Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly
            20                  25                  30

His Asn Ala Thr Phe Ser Glu Pro Leu Pro Phe Leu Tyr Val Leu Leu
        35                  40                  45

Pro Ala Val Tyr Ser Gly Ile Cys Ala Val Gly Leu Thr Gly Asn Thr
    50                  55                  60

Ala Val Ile Leu Val Ile Leu Arg Ala Pro Lys Met Lys Thr Val Thr
65                  70                  75                  80

Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160
```

Arg Gly Ala Lys Val Ala Ser Leu Cys Val Trp Leu Gly Val Thr Val
                165                 170                 175
Leu Val Leu Pro Phe Phe Ser Phe Ala Gly Val Tyr Ser Asn Glu Leu
            180                 185                 190
Gln Val Pro Ser Cys Gly Leu Ser Phe Pro Trp Pro Glu Gln Val Trp
        195                 200                 205
Phe Lys Ala Ser Arg Val Tyr Thr Leu Val Leu Gly Phe Val Leu Pro
    210                 215                 220
Val Cys Thr Ile Cys Val Leu Tyr Thr Asp Leu Leu Arg Arg Leu Arg
225                 230                 235                 240
Ala Val Arg Leu Arg Ser Gly Ala Lys Ala Leu Gly Lys Ala Arg Arg
                245                 250                 255
Lys Val Thr Val Leu Val Leu Val Leu Ala Val Cys Leu Leu Cys
                260                 265                 270
Trp Thr Pro Phe His Leu Ala Ser Val Val Ala Leu Thr Thr Asp Leu
            275                 280                 285
Pro Gln Thr Pro Leu Val Ile Ser Met Ser Tyr Val Ile Thr Ser Leu
        290                 295                 300
Ser Tyr Ala Asn Ser Cys Leu Asn Pro Phe Leu Tyr Ala Phe Leu Asp
305                 310                 315                 320
Asp Asn Phe Arg Lys Asn Phe Arg Ser Ile Leu Arg Cys
                325                 330

<210> SEQ ID NO 5
<211> LENGTH: 687
<212> TYPE: RNA
<213> ORGANISM: Artificial Sequence
<220> FEATURE:
<223> OTHER INFORMATION: Riboprobe

<400> SEQUENCE: 5
caaaagcugg agcuccaccg cgguggcggc cgcucuagcc cacuagugcc cuucagcacc      60
gcaauaugcu gcggaaguuc uuccggaagu ugucaucuag aaaggcguag aggaaggggu    120
ucaggcacga guuggcguag cugaggcugg ugaugacgua ggacauacug augaccagug    180
gggucugggg caggucccgug gucagggcca cgacagaggc cagguggaag ggcguccagc    240
agaggaggca cacggccagc acgacgagga ccaggacggu caccuuccgc cuggccuugc    300
cuagagccuu ggcuccagag cggagccgca cggcccgcag ccugcgcagg aggucugugu    360
agagcacaca gauggugcac acgggcagca cgaagcccag gaccaacgug uagacacggc    420
uggccuugaa ccagaccugc ucgggccacg ggaagcucag cccacagcuu gggaccugca    480
gcucguugcu guagacgcca gcgaaagaga agaagggcag aaccaggacc guagcgccca    540
gccagacaca caggcuggcg accuucgccc cccgguaggu gcgccagggc auggcgggg    600
accucacggu ggccagcacc accagguauc ggccacgcu caucacggcu aggaaguaga    660
ugcuggagaa gauguuguag uggucga      687

<210> SEQ ID NO 6
<211> LENGTH: 17
<212> TYPE: PRT
<213> ORGANISM: Porcine

<400> SEQUENCE: 6

Trp Tyr Lys His Thr Ala Ser Pro Arg Tyr His Thr Val Gly Arg Ala
1               5                   10                  15

Ala

<210> SEQ ID NO 7
<211> LENGTH: 438
<212> TYPE: DNA
<213> ORGANISM: Human
<220> FEATURE:
<221> NAME/KEY: misc_feature
<222> LOCATION: (408)..(408)
<223> OTHER INFORMATION: n = any nucleic acid

<400> SEQUENCE: 7

| | | | | | |
|---|---|---|---|---|---|
| gccccatgag | caggccagcg | gcgcggccca | ccgtgtggta | gcggggactc | gccacgtgct | 60 |
| tgtaccacgc | gccggagggc | agcggcagca | ggagcagaag | cagcagcagt | gccagccgcg | 120 |
| gccggctcgc | gggagccccc | cgctcccctg | gcgccacgc | cagggcgctc | gcgtcgacgg | 180 |
| ccgcccggcg | gggcgggcca | cgaaccggct | cggctggggt | tgggcgcgca | gtggagttgg | 240 |
| gacgcccagg | taccggagcg | caggaggctg | gaggcgagcc | gtgggtcccc | tgcaggccca | 300 |
| gctataaccg | ctcggtggcc | ccgcctcgtt | ccgccccctc | agtaccgctg | gctccccag | 360 |
| atgggggag | ggacggaggg | aggagaggga | accctggcag | ctggcggngg | acgtgggtac | 420 |
| ttgagcacct | cactgagt | | | | | 438 |

<210> SEQ ID NO 8
<211> LENGTH: 264
<212> TYPE: DNA
<213> ORGANISM: Human

<400> SEQUENCE: 8

| | | | | | |
|---|---|---|---|---|---|
| gatagggtga | gcgacgcagc | cccatgagca | ggccagcggc | gcggcccacc | gtgtggtagc | 60 |
| ggggactcgc | cacgtgcttg | taccacgcgc | cggagggcag | cggcagcagg | agcagaagca | 120 |
| gcagcagtgc | cagccgcggc | cggctcgcgg | gagcccccg | ctcccctggg | cgccacgcca | 180 |
| gggcgctcgc | gtcgacggcc | gcccggcggg | gcgggccacg | aaccggctcg | gctgggtttg | 240 |
| ggcgcgcagt | ggagttggga | cgcc | | | | 264 |

<210> SEQ ID NO 9
<211> LENGTH: 424
<212> TYPE: DNA
<213> ORGANISM: Human

<400> SEQUENCE: 9

| | | | | | |
|---|---|---|---|---|---|
| gatagggtga | gcgacgcagc | cccatgagca | ggccagcggc | gcggcccacc | gtgtggtagc | 60 |
| ggggactcgc | cacgtgcttg | taccacgcgc | cggagggcag | cggcagcagg | agcagaagca | 120 |
| gcagcagtgc | cagccgcggc | cggctcgcgg | gagcccccg | ctcccctggg | cgccacgcca | 180 |
| gggcgctcgc | gtcgacggcc | gcccggcggg | gcgggccacg | aaccggctcg | gctgggtttg | 240 |
| ggcgcgcagt | ggagttggga | cgcccaggta | ccggagcgca | ggaggctgga | ggcgagccgt | 300 |
| gggtccccctg | caggcccagc | tataaccgct | cggtggcccc | gcctcgttcc | gccccctcag | 360 |
| taccgctggg | ctccccagat | ggggggaggg | acggagggag | gagagggaac | cctggcagct | 420 |
| ggcg | | | | | | 424 |

<210> SEQ ID NO 10
<211> LENGTH: 375
<212> TYPE: DNA
<213> ORGANISM: Human

<400> SEQUENCE: 10

```
gcgcctcacc gtgtggtagc ggggactcgc cacgtgcttg taccacgcgc cggaggcagc    60
ggcacgagga gcagaagcag cagcagtgcc agccgcggcc ggctcgcggg agcccccgc    120 tccccctgggc gccacgcagg gctacagcgt cgacggccgc ccgcggggcc atcgcaaccg   180
gctcggctgg gtttgggcgc gcagtggagt tgggacgccc aggtaccgga gcgcaggagg   240
ctggaggcga gccgtgggtc ccctgcaggc ccagctataa ccgctcggtg gccccgcctc   300
gttccgcccc ctcagtaccg ctgggctccc cagaatgggg gagggacgga gggaggagag   360
ggaaccctgg cagct                                                    375
```

```
<210> SEQ ID NO 11
<211> LENGTH: 260
<212> TYPE: DNA
<213> ORGANISM: Human
<220> FEATURE:
<221> NAME/KEY: misc_feature
<222> LOCATION: (2)..(2)
<223> OTHER INFORMATION: n = any nucleic acid
<220> FEATURE:
<221> NAME/KEY: misc_feature
<222> LOCATION: (61)..(61)
<223> OTHER INFORMATION: n = any nucleic acid
<220> FEATURE:
<221> NAME/KEY: misc_feature
<222> LOCATION: (147)..(147)
<223> OTHER INFORMATION: n = any nucleic acid
<220> FEATURE:
<221> NAME/KEY: misc_feature
<222> LOCATION: (189)..(189)
<223> OTHER INFORMATION: n = any nucleic acid
<220> FEATURE:
<221> NAME/KEY: misc_feature
<222> LOCATION: (213)..(213)
<223> OTHER INFORMATION: n = any nucleic acid
<220> FEATURE:
<221> NAME/KEY: misc_feature
<222> LOCATION: (237)..(237)
<223> OTHER INFORMATION: n = any nucleic acid
<220> FEATURE:
<221> NAME/KEY: misc_feature
<222> LOCATION: (249)..(249)
<223> OTHER INFORMATION: n = any nucleic acid

<400> SEQUENCE: 11
```

```
cnacgttctc ggggacataa accctgttct tgtcctaacc cgccaagggg ccatggactt    60
nagcgcgctg gcgtcgagca gagaagtacg gggccctggg ccggggctcc ggtgaaccgg   120
cccctgctac cgctactgct gcttctnctc ttgctacctc tgcccgccag cgcctggtac   180
aagcacgtng cgagccctcg ctatcacaca gtnggtcgtg cctccgggct gctcatnggg   240
ctgcgccgnt cgtcctacct                                               260
```

```
<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
aactccactg cgcgcccaaa ccca                                           24
```

```
<210> SEQ ID NO 13
<211> LENGTH: 24
<212> TYPE: DNA
<213> ORGANISM: Artificial Sequence
<220> FEATURE:
```

-continued

<223> OTHER INFORMATION: Primer

<400> SEQUENCE: 13
tctcccacag ctcctgaacc cacg          24

<210> SEQ ID NO 14
<211> LENGTH: 375
<212> TYPE: DNA
<213> ORGANISM: Human

<400> SEQUENCE: 14
aactccactg cgcgcccaaa cccagccgag ccggttcgtg gcccgccccg ccggcggcc      60 gtcgacgcga gcgccctggc gtggcgccca ggggagcggg gggctcccgc gagccggccg    120
cggctggcac tgctgctgct tctgctcctg ctgccgctgc cctccggcgc gtggtacaag    180
cacgtggcga gtccccgcta ccacacggtg ggccgcgccg ctggcctgct catggggctg    240
cgtcgctcac cctatctgtg gcgccgcgcg ctgcgcgcgg ccgccgggcc cctggccagg    300
gacaccctct cccccgaacc cgcagcccgc gaggctcctc tcctgctgcc ctcgtgggtt    360
caggagctgt gggag                                                     375

<210> SEQ ID NO 15
<211> LENGTH: 125
<212> TYPE: PRT
<213> ORGANISM: Human

<400> SEQUENCE: 15

Asn Ser Thr Ala Arg Pro Asn Pro Ala Glu Pro Val Arg Gly Pro Pro
1               5                   10                  15

Arg Arg Ala Ala Val Asp Ala Ser Ala Leu Ala Trp Arg Pro Gly Glu
            20                  25                  30

Arg Gly Ala Pro Ala Ser Arg Pro Arg Leu Ala Leu Leu Leu Leu Leu
        35                  40                  45

Leu Leu Leu Pro Leu Pro Ser Gly Ala Trp Tyr Lys His Val Ala Ser
    50                  55                  60

Pro Arg Tyr His Thr Val Gly Arg Ala Ala Gly Leu Leu Met Gly Leu
65                  70                  75                  80

Arg Arg Ser Pro Tyr Leu Trp Arg Arg Ala Leu Arg Ala Ala Ala Gly
                85                  90                  95

Pro Leu Ala Arg Asp Thr Leu Ser Pro Glu Pro Ala Ala Arg Glu Ala
            100                 105                 110

Pro Leu Leu Leu Pro Ser Trp Val Gln Glu Leu Trp Glu
        115                 120                 125

<210> SEQ ID NO 16
<211> LENGTH: 23
<212> TYPE: PRT
<213> ORGANISM: Human

<400> SEQUENCE: 16

Trp Tyr Lys His Val Ala Ser Pro Arg Tyr His Thr Val Gly Arg Ala
1               5                   10                  15

Ala Gly Leu Leu Met Gly Leu
            20

<210> SEQ ID NO 17
<211> LENGTH: 30
<212> TYPE: PRT
<213> ORGANISM: Human

-continued

```
<400> SEQUENCE: 17

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr Leu Trp
            20                  25                  30

<210> SEQ ID NO 18
<211> LENGTH: 69
<212> TYPE: DNA
<213> ORGANISM: Human

<400> SEQUENCE: 18
tggtacaagc acgtggcgag tccccgctac cacacggtgg gccgcgccgc tggcctgctc     60
atggggctg                                                             69

<210> SEQ ID NO 19
<211> LENGTH: 90
<212> TYPE: DNA
<213> ORGANISM: Human

<400> SEQUENCE: 19
tggtacaagc acgtggcgag tccccgctac cacacggtgg gccgcgccgc tggcctgctc     60
atggggctgc gtcgctcacc ctatctgtgg                                      90

<210> SEQ ID NO 20
<211> LENGTH: 29
<212> TYPE: PRT
<213> ORGANISM: Human

<400> SEQUENCE: 20

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr Leu
            20                  25

<210> SEQ ID NO 21
<211> LENGTH: 28
<212> TYPE: PRT
<213> ORGANISM: Human

<400> SEQUENCE: 21

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr
            20                  25

<210> SEQ ID NO 22
<211> LENGTH: 27
<212> TYPE: PRT
<213> ORGANISM: Human

<400> SEQUENCE: 22

Trp Tyr Lys His Val Ala Ser Pro Arg Tyr His Thr Val Gly Arg Ala
1               5                   10                  15

Ala Gly Leu Leu Met Gly Leu Arg Arg Ser Pro
            20                  25

<210> SEQ ID NO 23
<211> LENGTH: 26
<212> TYPE: PRT
```

```
<213> ORGANISM: Human

<400> SEQUENCE: 23

Trp Tyr Lys His Val Ala Ser Pro Arg Tyr His Thr Val Gly Arg Ala
1               5                   10                  15

Ala Gly Leu Leu Met Gly Leu Arg Arg Ser
            20                  25

<210> SEQ ID NO 24
<211> LENGTH: 25
<212> TYPE: PRT
<213> ORGANISM: Human

<400> SEQUENCE: 24

Trp Tyr Lys His Val Ala Ser Pro Arg Tyr His Thr Val Gly Arg Ala
1               5                   10                  15

Ala Gly Leu Leu Met Gly Leu Arg Arg
            20                  25

<210> SEQ ID NO 25
<211> LENGTH: 24
<212> TYPE: PRT
<213> ORGANISM: Human

<400> SEQUENCE: 25

Trp Tyr Lys His Val Ala Ser Pro Arg Tyr His Thr Val Gly Arg Ala
1               5                   10                  15

Ala Gly Leu Leu Met Gly Leu Arg
            20

<210> SEQ ID NO 26
<211> LENGTH: 87
<212> TYPE: DNA
<213> ORGANISM: Human

<400> SEQUENCE: 26
tggtacaagc acgtggcgag tccccgctac cacacggtgg gccgcgccgc tggcctgctc      60
atggggctgc gtcgctcacc ctatctg                                         87

<210> SEQ ID NO 27
<211> LENGTH: 84
<212> TYPE: DNA
<213> ORGANISM: Human

<400> SEQUENCE: 27
tggtacaagc acgtggcgag tccccgctac cacacggtgg gccgcgccgc tggcctgctc      60
atggggctgc gtcgctcacc ctat                                            84

<210> SEQ ID NO 28
<211> LENGTH: 81
<212> TYPE: DNA
<213> ORGANISM: Human

<400> SEQUENCE: 28
tggtacaagc acgtggcgag tccccgctac cacacggtgg gccgcgccgc tggcctgctc      60
atggggctgc gtcgctcacc c                                               81

<210> SEQ ID NO 29
<211> LENGTH: 78
<212> TYPE: DNA
<213> ORGANISM: Human
```

<400> SEQUENCE: 29

```
tggtacaagc acgtggcgag tccccgctac cacacggtgg gccgcgccgc tggcctgctc    60
atggggctgc gtcgctca                                                  78
```

<210> SEQ ID NO 30
<211> LENGTH: 75
<212> TYPE: DNA
<213> ORGANISM: Human

<400> SEQUENCE: 30

```
tggtacaagc acgtggcgag tccccgctac cacacggtgg gccgcgccgc tggcctgctc    60
atggggctgc gtcgc                                                     75
```

<210> SEQ ID NO 31
<211> LENGTH: 72
<212> TYPE: DNA
<213> ORGANISM: Human

<400> SEQUENCE: 31

```
tggtacaagc acgtggcgag tccccgctac cacacggtgg gccgcgccgc tggcctgctc    60
atggggctgc gt                                                        72
```

<210> SEQ ID NO 32
<211> LENGTH: 999
<212> TYPE: DNA
<213> ORGANISM: Human

<400> SEQUENCE: 32

```
atgcaggccg ctgggcaccc agagcccctt gacagcaggg gctccttctc cctccccacg    60
atgggtgcca acgtctctca ggacaatggc actggccaca atgccacctt ctccgagcca   120
ctgccgttcc tctatgtgct cctgcccgcc gtgtactccg ggatctgtgc tgtggggctg   180
actggcaaca cggccgtcat ccttgtaatc ctaagggcgc ccaagatgaa gacggtgacc   240
aacgtgttca tcctgaacct ggccgtcgcc gacgggctct tcacgctggt actgcccgtc   300
aacatcgcgg agcacctgct gcagtactgg cccttcgggg agctgctctg caagctggtg   360
ctggccgtcg accactacaa catcttctcc agcatctact tcctagccgt gatgagcgtg   420
gaccgatacc tggtggtgct ggccaccgtg aggtcccgcc acatgccctg cgcacctac    480
cggggggcga aggtcgccag cctgtgtgtc tggctgggcg tcacggtcct ggttctgccc   540
ttcttctctt tcgctggcgt ctacagcaac gagctgcagg tcccaagctg tgggctgagc   600
ttcccgtggc ccgagcgggt ctggttcaag gccagccgtg tctacacttt ggtcctgggc   660
ttcgtgctgc ccgtgtgcac catctgtgtg ctctacacag acctcctgcg caggctgcgg   720
gccgtgcggc tccgctctgg agccaaggct ctaggcaagg ccaggcggaa ggtgaccgtc   780
ctggtcctcg tcgtgctggc cgtgtgcctc ctctgctgga cgcccttcca cctggcctct   840
gtcgtggccc tgaccacgga cctgcccag accccactgg tcatcagtat gtcctacgtc   900
atcaccagcc tcacgtacgc caactcgtgc ctgaaccccct tcctctacgc ctttctagat   960
gacaacttcc ggaagaactt ccgcagcata ttgcggtgc                          999
```

<210> SEQ ID NO 33
<211> LENGTH: 24
<212> TYPE: DNA
<213> ORGANISM: Artificial Sequence
<220> FEATURE:

```
<223> OTHER INFORMATION: Primer

<400> SEQUENCE: 33
tctcccacag ctcctgaacc cacg                                           24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
acagataggg tgagcgacgc agcc                                           24

<210> SEQ ID NO 35
<211> LENGTH: 1102
<212> TYPE: DNA
<213> ORGANISM: Human

<400> SEQUENCE: 35
gccatttaag tggagtcttg aaggatgagt aggtgttagg cacagacgca cagaggcagg     60
caaagccaca ggctgttggt ttaggcaaaa attgagactg gctggataaa gtggtcttgg    120
gggaccatca ccagagagga ggcgctggag gtctgcaagg ccttgtcctg cccctccagg    180
ggtagaggtt ccaggagggg ctgactttt tcctggaag cctcacagaa ctgcagaccc    240
cacggatggc ttggtgttgc caacatgagg cttctaaggc ttctgcgggg agatgggttg    300
gtggggagaa gctgggggtg gcagtggaca ggacagggtg tggggacagc tttgggagct    360
atgctaggca aggacaaggg acaactcttg gggggactca cccagagggg tcttgaatgg    420
tgctgaaggc ccccgacagc cctcctgcaa tagccactgt agctctgcct gcacctgggc    480
cttcgctctg ctgtcgtccc accggcagga gtctggctaa aggggcatcc ctcagcccta    540
ctccctcatc agtgttccca gtacccactc cctggcactt ccactcctag agggaggagg    600
ctgagcaggc agagaatggg acgtgtcccc tcagaggagc ctcgagccca gttccagcca    660
gcggcccact cagtgaggtg ctcaagtacc cacgtccccc gccagctgcc agggttccct    720
ctcctccctc cgtccctccc cccatctggg gagcccagcg gtactgaggg gcggaacga    780 ggcggggcca ccgagcggtt atagctgggc ctgcagggga cccacggctc gcctccagcc    840
tcctgcgctc cggtacctgg gcgtcccaac tccactgcgc gcccaaaccc agccgagccg    900
gttcgtggcc cgcccgccg gcggccgtc gacgcgagcg ccctggcgtg cgcccaggg     960 gagcggggg ctcccgcgag ccggccgcgg ctggcactgc tgctgcttct gctcctgctg   1020
ccgctgccct ccggcgcgtg gtacaagcac gtggcgagtc cccgctacca cacggtgggc   1080
cgcgccgctg gcctgctcat gg                                          1102

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
aactccactg cgcgcccaaa ccca                                           24

<210> SEQ ID NO 37
<211> LENGTH: 24
```

```
<212> TYPE: DNA
<213> ORGANISM: Artificial Sequence
<220> FEATURE:
<223> OTHER INFORMATION: Primer

<400> SEQUENCE: 37
ctggcactgc tgctgcttct gctc                                              24

<210> SEQ ID NO 38
<211> LENGTH: 609
<212> TYPE: DNA
<213> ORGANISM: Human

<400> SEQUENCE: 38
ctgctgccgc tgccctccgg cgcgtggtac aagcacgtgg cgagtccccg ctaccacacg      60
gtgggccgcg ccgctggcct gctcatgggg ctgcgtcgct caccctatct gtggcgccgc     120
gcgctgcgcg cggccgccgg gcccctggcc agggacaccc tctcccccga acccgcagcc     180
cgcgaggctc ctctcctgct gccctcgtgg gttcaggagc tgtgggagac gcgacgcagg     240
agctcccagg cagggatccc cgtccgtgcg ccccggagcc cgcgcgcccc agagcctgcg     300
ctggaaccgg agtccctgga cttcagcgga gctggccaga gacttcggag agacgtctcc     360
cgcccagcgg tggaccccgc agcaaaccgc cttggcctgc cctgcctggc ccccggaccg     420
ttctgacagc gtccccgcc cgccgtggc gcctccgcgc ctgacccagg aggagtggcc     480
gcgcgcttcc aggagccgct catagacccc gcctgccgtc cggtcaataa aatccgcctg     540
actcctgcgc ccccgcatgc gtaaaaaaaa aaaaaaaaa aaaaaaaaaa agcggccgct     600
gaattctag                                                             609

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
agcggtactg aggggcgga acga                                              24

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
gggtctatga gcggctcctg gaag                                             24

<210> SEQ ID NO 41
<211> LENGTH: 719
<212> TYPE: DNA
<213> ORGANISM: Human

<400> SEQUENCE: 41
ggcggggcca ccgagcggtt atagctgggc ctgcagggga cccacggctc gcctccagcc      60
tcctgcgctc cggtacctgg gcgtcccaac tccactgcgc gcccaaaccc agccgagccg     120
gttcgtggcc cgccccgccg ggcggccgtc gacgcgagcg ccctggcgtg gcgcccaggg     180
gagcgggggg ctcccgcgag ccggccgcgg ctggcactgc tgctgcttct gctcctgctg     240
```

```
ccgctgccct ccggcgcgtg gtacaagcac gtggcgagtc cccgctacca cacggtgggc    300
cgcgccgctg gcctgctcat ggggctgcgt cgctcaccct atctgtggcg ccgcgcgctg    360
cgcgcggccg ccgggcccct ggccagggac accctctccc cgaacccgc agcccgcgag     420 gctcctctcc tgctgccctc gtgggttcag gagctgtggg agacgcgacg caggagctcc    480
caggcaggga tccccgtccg tgcgccccgg agcccgcgcg ccccagagcc tgcgctggaa    540
ccggagtccc tggacttcag cggagctggc cagagacttc ggagagacgt ctcccgccca    600
gcggtggacc ccgcagcaaa ccgccttggc ctgccctgcc tggccccgg accgttctga     660 cagcgtcccc cgcccgcccg tggcgcctcc gcgcctgacc caggaggagt ggccgcgcg    719
```

<210> SEQ ID NO 42
<211> LENGTH: 165
<212> TYPE: PRT
<213> ORGANISM: Human

<400> SEQUENCE: 42

```
Leu Ala Trp Arg Pro Gly Glu Arg Gly Ala Pro Ala Ser Arg Pro Arg
 1               5                  10                  15

Leu Ala Leu Leu Leu Leu Leu Leu Leu Pro Leu Pro Ser Gly Ala
             20                  25                  30

Trp Tyr Lys His Val Ala Ser Pro Arg Tyr His Thr Val Gly Arg Ala
         35                  40                  45

Ala Gly Leu Leu Met Gly Leu Arg Arg Ser Pro Tyr Leu Trp Arg Arg
     50                  55                  60

Ala Leu Arg Ala Ala Ala Gly Pro Leu Ala Arg Asp Thr Leu Ser Pro
65                  70                  75                  80

Glu Pro Ala Ala Arg Glu Ala Pro Leu Leu Pro Ser Trp Val Gln
                 85                  90                  95

Glu Leu Trp Glu Thr Arg Arg Arg Ser Ser Gln Ala Gly Ile Pro Val
                100                 105                 110

Arg Ala Pro Arg Ser Pro Arg Ala Pro Glu Pro Ala Leu Glu Pro Glu
            115                 120                 125

Ser Leu Asp Phe Ser Gly Ala Gly Gln Arg Leu Arg Arg Asp Val Ser
        130                 135                 140

Arg Pro Ala Val Asp Pro Ala Ala Asn Arg Leu Gly Leu Pro Cys Leu
145                 150                 155                 160

Ala Pro Gly Pro Phe
                165
```

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
acagataggg tgagcgacgc agcc                                             24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44

```
tgagcgacgc agccccatga gcag                                                24
```

<210> SEQ ID NO 45
<211> LENGTH: 235
<212> TYPE: DNA
<213> ORGANISM: Porcine

<400> SEQUENCE: 45

```
cgacacccct gcgcccagac cctccggagc cagttcctgg tccgccccgc cgggagccgt          60
cagcatgaac ccccgggcac gcggcatggg agcgcggggc ccgggaccgg gggccactgc         120
gaggcgccgg ctgctggcat tgctgttact gctgctgctg ctgccgctgc ccgcccgtgc         180
ctggtacaag cacacggcga gtccccgcta ccacacggtg ggccgcgccg cgggc             235
```

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46

```
cagcggcagc agcagcagca gtaa                                                24
```

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47

```
cagcagtaac agcaatgcca gcag                                                24
```

<210> SEQ ID NO 48
<211> LENGTH: 156
<212> TYPE: DNA
<213> ORGANISM: Porcine

<400> SEQUENCE: 48

```
ctgtagcctc ccgcgctgcg gcttcccgac accctgcgc ccagaccctc cggagcagt           60 tcctggtccg ccccgccggg agccgtcagc atgaacccc gggcacgcgg catgggagcg         120
cggggcccgg gaccgggggc cactgcgagg cgccgg                                  156
```

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49

```
cggctgctgg cattgctgtt actg                                                24
```

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50

```
cgcccgtgcc tggtacaagc aca                                                 23
```

<210> SEQ ID NO 51
<211> LENGTH: 588
<212> TYPE: DNA
<213> ORGANISM: Porcine

<400> SEQUENCE: 51

```
cggcgagtcc ccgctaccac acggtgggcc gcgccgcggg cctgctcatg gggctgcgcc      60
gctcgcccta catgtggcgc gcgcgcgctgc gcccggcggc cgggcccctg gcctgggaca    120
ctttcggcca ggacgtgccc cctcggggac cctccgccag gaacgccctc tctccggggc    180
ccgcccctcg cgacgctccg ctgcttcccc ccggggttca gacactgtgg caggtgcgac    240
gcggaagctt ccgctccggg atcccggtca gtgcgcccg cagcccgcgc gcccgggggt    300
ccgagccgca accggaattg gcgcctctt cctggacctc ggcggagtag accagagcct    360
tcggagagtc ttcagctcag cggtggtctg cgcagggaac cgccttcgcc agccccccgcc   420
tcgccccagc gtcagagccg acctgatcgc ggccccggcg gcgcggcccc gcgcctggcc    480
cccgcggagt ctcttcgcgc ccccaggccg ccgtctggt caataaaacc cgcctagttc    540
ctgcgaaaaa aaaaaaaaa aaaaaaaaa aaaaaaaaa aaaaaaa                      588
```

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52

```
ttcccgacac ccctgcgccc agac                                            24
```

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53

```
gggctggcga aggcggttcc ctgc                                            24
```

<210> SEQ ID NO 54
<211> LENGTH: 565
<212> TYPE: DNA
<213> ORGANISM: Porcine

<400> SEQUENCE: 54

```
cctccggagc cagttcctgg tccgccccgc cgggagccgt cagcatgaac ccccgggcac      60
gcggcatggg agcgcggggc ccgggaccgg gggccactgc gaggcgccgg ctgctggcat    120
tgctgttact gctgctgctg ctgccgctgc ccgcccgtgc ctggtacaag cacacggcga    180
gtccccgcta ccacacggtg ggccgcgccg cgggcctgct catggggctg cgccgctcgc    240
cctacatgtg gcgccgcgcg ctgcgcccgg cggcggggcc cctggcctgg gacactttcg    300
gccaggacgt gccccctcgg ggaccctccg ccaggaacgc cctctctccg ggcccgccc    360
ctcgcgacgc tccgctgctt cccccgggg ttcagacact gtggcaggtg cgacgcggaa    420
gcttccgctc cgggatcccg gtcagtgcgc cccgcagccc gcgcgccggg ggtccgagc    480
cgcaaccgga attgggcgcc tcttcctgga cctcggcgga gtagaccaga gccttcggag    540
```

```
agtcttcagc tcagcggtgg tctgc                                          565
```

<210> SEQ ID NO 55
<211> LENGTH: 159
<212> TYPE: PRT
<213> ORGANISM: Porcine

<400> SEQUENCE: 55

```
Met Asn Pro Arg Ala Arg Gly Met Gly Ala Arg Gly Pro Gly Pro Gly
1               5                   10                  15

Ala Thr Ala Arg Arg Arg Leu Leu Ala Leu Leu Leu Leu Leu Leu Leu
            20                  25                  30

Leu Pro Leu Pro Ala Arg Ala Trp Tyr Lys His Thr Ala Ser Pro Arg
        35                  40                  45

Tyr His Thr Val Gly Arg Ala Gly Leu Leu Met Gly Leu Arg Arg
    50                  55                  60

Ser Pro Tyr Met Trp Arg Arg Ala Leu Arg Pro Ala Ala Gly Pro Leu
65              70                  75                  80

Ala Trp Asp Thr Phe Gly Gln Asp Val Pro Pro Arg Gly Pro Ser Ala
            85                  90                  95

Arg Asn Ala Leu Ser Pro Gly Pro Ala Pro Arg Asp Ala Pro Leu Leu
        100                 105                 110

Pro Pro Gly Val Gln Thr Leu Trp Gln Val Arg Gly Ser Phe Arg
    115                 120                 125

Ser Gly Ile Pro Val Ser Ala Pro Arg Ser Pro Arg Ala Arg Gly Ser
130                 135                 140

Glu Pro Gln Pro Glu Leu Gly Ala Ser Ser Trp Thr Ser Ala Glu
145                 150                 155
```

<210> SEQ ID NO 56
<211> LENGTH: 23
<212> TYPE: PRT
<213> ORGANISM: Porcine

<400> SEQUENCE: 56

```
Trp Tyr Lys His Thr Ala Ser Pro Arg Tyr His Thr Val Gly Arg Ala
1               5                   10                  15

Ala Gly Leu Leu Met Gly Leu
            20
```

<210> SEQ ID NO 57
<211> LENGTH: 30
<212> TYPE: PRT
<213> ORGANISM: Porcine

<400> SEQUENCE: 57

```
Trp Tyr Lys His Thr Ala Ser Pro Arg Tyr His Thr Val Gly Arg Ala
1               5                   10                  15

Ala Gly Leu Leu Met Gly Leu Arg Arg Ser Pro Tyr Met Trp
            20                  25                  30
```

<210> SEQ ID NO 58
<211> LENGTH: 69
<212> TYPE: DNA
<213> ORGANISM: Porcine

<400> SEQUENCE: 58

```
tggtacaagc acacggcgag tccccgctac cacacggtgg ccgcgccgc gggcctgctc    60 atggggctg                                                           69
```

<210> SEQ ID NO 59
<211> LENGTH: 90
<212> TYPE: DNA
<213> ORGANISM: Porcine

<400> SEQUENCE: 59
tggtacaagc acacggcgag tccccgctac cacacggtgg gccgcgccgc gggcctgctc    60
atggggctgc gccgctcgcc ctacatgtgg                                    90

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
cgttctcggg gacataaacc ctg                                           23

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
atgagcagcc cggaggcacg acc                                           23

<210> SEQ ID NO 62
<211> LENGTH: 188
<212> TYPE: DNA
<213> ORGANISM: Rat

<400> SEQUENCE: 62
ttcttgtcct aacccgccaa ggggccatgg acttgagcgc gctggcgtcg agcagagaag    60
tacggggccc tgggcccggg gctccggtga accggcccct gctaccgcta ctgctgcttc   120
tgctcttgct acctctgccc gccagcgcct ggtacaagca cgtggcgagc cctcgctatc   180
acacagtg                                                           188

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
atgagcagcc cggaggcacg acc                                           23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
actgtgtgat agcgagggct cgc                                           23

<210> SEQ ID NO 65

<211> LENGTH: 615
<212> TYPE: DNA
<213> ORGANISM: Rat

<400> SEQUENCE: 65

| | | |
|---|---|---|
| ctcagagctg tactaggcag gaagagggac ggccctcagg gaaggtggc cctatgctta | 60 |
| aaactttcct gtctcctctc cataagtgct ccacttgtag caactcctac caaggggca | 120 |
| tccttttgcc cctggcagcc catccttgta ttctgagacc atgcatggta ccagaactcc | 180 |
| ctccctgaca gttcccttcc tggggcgag gaaagggtaa gcaaggagat cccccactaa | 240 |
| agcttcaagc gcagtccagc ttgcgatcta ctcattggga ggcttctagc tacccgggtt | 300 |
| ccctcttctc cctccctctc catcctcctc tcccttgggc atgtgccgcg gggcgagcc | 360 |
| ggggcgggc cattgagaag ctgtagtcgc accaactgac tagtctcttc catcctccgg | 420 |
| agctccgacg ttctcgggga cataaaccct gttcttgtcc taacccgcca aggggccatg | 480 |
| gacttgagcg cgctggcgtc gagcagagaa gtacggggcc ctgggccgg ggctccggtg | 540 |
| aaccggcccc tgctaccgct actgctgctt ctgctcttgc tacctctgcc cgccagcgcc | 600 |
| tggtacaagc acgtg | 615 |

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
cgttctcggg gacataaacc ctg                                          23

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
cgagccctcg ctatcacaca gtgg                                         24

<210> SEQ ID NO 68
<211> LENGTH: 497
<212> TYPE: DNA
<213> ORGANISM: Rat

<400> SEQUENCE: 68

| | | |
|---|---|---|
| gtcgtgcctc cgggctgctc atgggctgc gccgctcgcc ctacctgtgg cgccgtgcct | 60 |
| tgggtggggc cgctggaccg ctcgtggggc tcccgggaca gatggcccgc agcgctctcc | 120 |
| tgcttccttc ccccggcag gagctgtggg aggtacgaag caggagttca ccggcaggac | 180 |
| ttcccgtgca tgcaacccgg agtctgcggg acctggaggg agccggccaa cctgagcagt | 240 |
| cgctaagctt tcagtcctgg acttcagcag agcccgctgc tagagccttc ggtgagacgc | 300 |
| ttcgtgccca gccatggttc ctgcagcaaa tcatctttgc cgatcctgtc aggctcgacg | 360 |
| accgtctcaa gaaccgatgg cgccccgtg cttgacctaa gcaggagcac agcttgtagc | 420 |
| tccagtcagg tctcgttgtc tggtcaataa aatcactctg attcccaaaa aaaaaaaaa | 480 |
| aaaaaaaaaa aaaaaaa | 497 |

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
ggggcggggc cattgagaag c                                                   21

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
tgaccagaca acgagacctg a                                                   21

<210> SEQ ID NO 71
<211> LENGTH: 684
<212> TYPE: DNA
<213> ORGANISM: Rat

<400> SEQUENCE: 71
tgtagtcgca ccaactgact agtctcttcc atcctccgga gctccgacgt tctcggggac         60 ataaacctg ttcttgtcct aacccgccaa ggggccatgg acttgagcgc gctggcgtcg         120
agcagagaag tacggggccc tgggcccggg gctccggtga accggcccct gctaccgcta        180
ctgctgcttc tgctcttgct acctctgccc gccagcgcct ggtacaagca cgtggcgagc        240
cctcgctatc acacagtggg tcgtgcctcc gggctgctca tggggctgcg ccgctcgccc        300
tacctgtggc gccgtgcctt gggtggggcc gctggaccgc tcgtggggct cccgggacag        360
atggcccgca cgctctcct gcttccttcc cccgggcagg agctgtggga ggtacgaagc        420
aggagttcac cggcaggact tcccgtgcat gcaacccgga gtctgcggga cctggaggga        480
gccggccaac ctgagcagtc gctaagcttt cagtcctgga cttcagcaga gcccgctgct        540
agagccttcg gtgagacgct tcgtgcccag ccatggttcc tgcagcaaat catctttgcc        600
gatcctgtca ggctcgacga ccgtctcaag aaccgatggc gccccgtgc ttgacctaag        660 caggagcaca gcttgtagct ccag                                                684

<210> SEQ ID NO 72
<211> LENGTH: 185
<212> TYPE: PRT
<213> ORGANISM: Rat

<400> SEQUENCE: 72

Met Asp Leu Ser Ala Leu Ala Ser Ser Arg Glu Val Arg Gly Pro Gly
1               5                   10                  15

Pro Gly Ala Pro Val Asn Arg Pro Leu Leu Pro Leu Leu Leu Leu Leu
            20                  25                  30

Leu Leu Leu Pro Leu Pro Ala Ser Ala Trp Tyr Lys His Val Ala Ser
        35                  40                  45

Pro Arg Tyr His Thr Val Gly Arg Ala Ser Gly Leu Leu Met Gly Leu
    50                  55                  60

Arg Arg Ser Pro Tyr Leu Trp Arg Arg Ala Leu Gly Gly Ala Ala Gly
65                  70                  75                  80

Pro Leu Val Gly Leu Pro Gly Gln Met Ala Arg Ser Ala Leu Leu Leu

```
                85                  90                  95
Pro Ser Pro Gly Gln Glu Leu Trp Glu Val Arg Ser Arg Ser Pro
            100                 105                 110
Ala Gly Leu Pro Val His Ala Thr Arg Ser Leu Arg Asp Leu Glu Gly
        115                 120                 125
Ala Gly Gln Pro Glu Gln Ser Leu Ser Phe Gln Ser Trp Thr Ser Ala
    130                 135                 140
Glu Pro Ala Ala Arg Ala Phe Gly Glu Thr Leu Arg Ala Gln Pro Trp
145                 150                 155                 160
Phe Leu Gln Gln Ile Ile Phe Ala Asp Pro Val Arg Leu Asp Asp Arg
                165                 170                 175
Leu Lys Asn Arg Trp Arg Pro Arg Ala
                180                 185

<210> SEQ ID NO 73
<211> LENGTH: 23
<212> TYPE: PRT
<213> ORGANISM: Rat

<400> SEQUENCE: 73

Trp Tyr Lys His Val Ala Ser Pro Arg Tyr His Thr Val Gly Arg Ala
1               5                   10                  15

Ser Gly Leu Leu Met Gly Leu
            20

<210> SEQ ID NO 74
<211> LENGTH: 30
<212> TYPE: PRT
<213> ORGANISM: Rat

<400> SEQUENCE: 74

Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Leu Trp
            20                  25                  30

<210> SEQ ID NO 75
<211> LENGTH: 69
<212> TYPE: DNA
<213> ORGANISM: Rat

<400> SEQUENCE: 75
tggtacaagc acgtggcgag ccctcgctat cacacagtgg gtcgtgcctc cgggctgctc      60
atggggctg                                                             69

<210> SEQ ID NO 76
<211> LENGTH: 90
<212> TYPE: DNA
<213> ORGANISM: Rat

<400> SEQUENCE: 76
tggtacaagc acgtggcgag ccctcgctat cacacagtgg gtcgtgcctc cgggctgctc      60
atggggctgc gccgctcgcc ctacctgtgg                                      90

<210> SEQ ID NO 77
<211> LENGTH: 529
<212> TYPE: DNA
<213> ORGANISM: Mouse

<400> SEQUENCE: 77
```

```
acgtgctcgt tctcggagac ataaacccag ttcttgtcct aaccctccaa ggggcaattg      60
acgtgagcgc gctggcgtct aacagagaag tacggggccc tgggcccggg actcccagga     120
accggcccct gctgcccctg ctgctgcttc tgctcttgct accgctgccc gccagcgcct     180
ggtataagca cgtggcgagt ccccgctatc acacagtggg tcgtgcctcc gggctgctca     240
tggggctgcg ccgctcgccc taccagtggc gccgtgccct gggcggggct gctggacccc     300
tctcccggct cccaggaccg gtcgcccgcg gcgctctcct gcttccttcc tcagggcagg     360
agctgtggga ggtacgaagc aggagctcac ctgcagggct cccgtccat gcaccctgga      420 gtccgcggga cctggaggga gtccgccaac cggagcagtc gctaagcctt cactcctgga     480
tgtcagagga gcccgctgat aggtaagtag gaaagagagg aggcgggcg               529
```

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
acccagttct tgtcctaacc ctcc                                            24

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79
cctgcttcgt acctcccaca gctc                                            24

<210> SEQ ID NO 80
<211> LENGTH: 311
<212> TYPE: DNA
<213> ORGANISM: Mouse

<400> SEQUENCE: 80

```
aaggggcaat tgacgtgagc gcgctggcgt ctaacagaga agtacggggc cctgggcccg      60
ggactcccag gaaccggccc ctgctgcccc tgctgctgct tctgctcttg ctaccgctgc     120
ccgccagcgc ctggtataag cacgtggcga gtccccgcta tcacacagtg ggtcgtgcct     180
ccgggctgct catgggctg cgccgctcgc cctaccagtg gcgccgtgcc ctgggcgggg     240
ctgctggacc cctctcccgg ctcccaggac cggtcgcccg cggcgctctc ctgcttcctt     300
cctcagggca g                                                         311
```

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
catgagcagc ccggaggcac gacc                                            24

<210> SEQ ID NO 82
<211> LENGTH: 24
<212> TYPE: DNA

```
<213> ORGANISM: Artificial Sequence
<220> FEATURE:
<223> OTHER INFORMATION: Primer

<400> SEQUENCE: 82
gtgatagcgg ggactcgcca cgtg                                            24

<210> SEQ ID NO 83
<211> LENGTH: 237
<212> TYPE: DNA
<213> ORGANISM: Mouse

<400> SEQUENCE: 83
aaaggctgta gtcgcaccaa ctgactggtc tccatcctct ggagctccga cgtgctcgtt     60
ctcggagaca taaacccagt tcttgtccta accctccaag gggcaattga cgtgagcgcg    120
ctggcgtcta acagagaagt acggggccct gggcccggga ctcccaggaa ccggcccctg    180
ctgcccctgc tgctgcttct gctcttgcta ccgctgcccg ccagcgcctg gtataag       237

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
acccagttct tgtcctaacc ctcc                                            24

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
gggcaattga cgtgagcgcg ctgg                                            24

<210> SEQ ID NO 86
<211> LENGTH: 598
<212> TYPE: DNA
<213> ORGANISM: Mouse

<400> SEQUENCE: 86
cgtctaacag agaagtacgg ggccctgggc ccggactcc caggaaccgg ccctgctgc       60 ccctgctgct gcttctgctc ttgctaccgc tgcccgccag cgcctggtat aagcacgtgg    120
cgagtccccg ctatcacaca gtgggtcgtg cctccgggct gctcatgggg ctgcgccgct    180
cgccctacca gtggcgccgt gccctgggcg gggctgctgg acccctctcc cggctcccag    240
gaccggtcgc ccgcggcgct ctcctgcttc cttcctcagg gcaggagctg tgggaggtac    300
gaagcaggag ctcacctgca gggcttcccg tccatgcacc ctggagtccg cgggacctgg    360
agggagtccg ccaaccggag cagtcgctaa gccttcactc ctggatctca gaggagcccg    420
ctgctagagc cttcggagag acgcttcgtg cccagccatg gttcctgcag caagtcatct    480
ttgccgatcc tgtcaggccc aagaaccgat ggcgccccca tgcttgacct aggcaggagc    540
acagcttgaa gctccagtca ggcctcgtgt ttctggtcaa taaaaccaac ctgattcc      598

<210> SEQ ID NO 87
<211> LENGTH: 21
```

<212> TYPE: DNA
<213> ORGANISM: Artificial Sequence
<220> FEATURE:
<223> OTHER INFORMATION: Primer

<400> SEQUENCE: 87
aaaggctgta gtcgcaccaa c                                                21

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
accagaaaca cgaggcctga c                                                21

<210> SEQ ID NO 89
<211> LENGTH: 659
<212> TYPE: DNA
<213> ORGANISM: Mouse

<400> SEQUENCE: 89
tgactggtct ccatcctctg gagctccgac gtgctcgttc tcggagacat aaacccagtt        60
cttgtcctaa ccctccaagg ggcaattgac gtgagcgcgc tggcgtctaa cagagaagta       120
cggggccctg ggcccgggac tcccaggaac cggcccctgc tgcccctgct gctgcttctg       180
ctcttgctac cgctgcccgc cagcgcctgg tataagcacg tggcgagtcc ccgctatcac       240
acagtgggtc gtgcctccgg gctgctcatg gggctgcgcc gctcgcccta ccagtggcgc       300
cgtgccctgg gcgggctgc tggacccctc tcccggctcc caggaccggt cgcccgcggc        360
gctctcctgc ttccttcctc agggcaggag ctgtgggagg tacgaagcag gagctcacct       420
gcagggcttc ccgtccatgc accctggagt ccgcgggacc tggagggagt ccgccaaccg       480
gagcagtcgc taagccttca ctcctggatc tcagaggagc ccgctgctag agccttcgga       540
gagacgcttc gtgcccagcc atggttcctg cagcaagtca tctttgccga tcctgtcagg       600
cccaagaacc gatggcgccc ccatgcttga cctaggcagg agcacagctt gaagctcca        659

<210> SEQ ID NO 90
<211> LENGTH: 176
<212> TYPE: PRT
<213> ORGANISM: Mouse

<400> SEQUENCE: 90

Leu Ala Ser Asn Arg Glu Val Arg Gly Pro Gly Pro Gly Thr Pro Arg
1               5                   10                  15

Asn Arg Pro Leu Leu Pro Leu Leu Leu Leu Leu Leu Leu Leu Pro Leu
                20                  25                  30

Pro Ala Ser Ala Trp Tyr Lys His Val Ala Ser Pro Arg Tyr His Thr
            35                  40                  45

Val Gly Arg Ala Ser Gly Leu Leu Met Gly Leu Arg Arg Ser Pro Tyr
        50                  55                  60

Gln Trp Arg Arg Ala Leu Gly Gly Ala Ala Gly Pro Leu Ser Arg Leu
65                  70                  75                  80

Pro Gly Pro Val Ala Arg Gly Ala Leu Leu Leu Pro Ser Ser Gly Gln
                85                  90                  95

Glu Leu Trp Glu Val Arg Ser Arg Ser Ser Pro Ala Gly Leu Pro Val
                100                 105                 110

His Ala Pro Trp Ser Pro Arg Asp Leu Glu Gly Val Arg Gln Pro Glu
            115                 120                 125

Gln Ser Leu Ser Leu His Ser Trp Ile Ser Glu Pro Ala Ala Arg
        130                 135                 140

Ala Phe Gly Glu Thr Leu Arg Ala Gln Pro Trp Phe Leu Gln Gln Val
145                 150                 155                 160

Ile Phe Ala Asp Pro Val Arg Pro Lys Asn Arg Trp Arg Pro His Ala
                165                 170                 175

<210> SEQ ID NO 91
<211> LENGTH: 23
<212> TYPE: PRT
<213> ORGANISM: Mouse

<400> SEQUENCE: 91

Trp Tyr Lys His Val Ala Ser Pro Arg Tyr His Thr Val Gly Arg Ala
1               5                   10                  15

Ser Gly Leu Leu Met Gly Leu
            20

<210> SEQ ID NO 92
<211> LENGTH: 30
<212> TYPE: PRT
<213> ORGANISM: Mouse

<400> SEQUENCE: 92

Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Gln Trp
            20                  25                  30

<210> SEQ ID NO 93
<211> LENGTH: 69
<212> TYPE: DNA
<213> ORGANISM: Mouse

<400> SEQUENCE: 93
tggtataagc acgtggcgag tccccgctat cacacagtgg gtcgtgcctc cgggctgctc    60
atggggctg                                                            69

<210> SEQ ID NO 94
<211> LENGTH: 90
<212> TYPE: DNA
<213> ORGANISM: Mouse

<400> SEQUENCE: 94
tggtataagc acgtggcgag tccccgctat cacacagtgg gtcgtgcctc cgggctgctc    60
atggggctgc gccgctcgcc ctaccagtgg                                     90

<210> SEQ ID NO 95
<211> LENGTH: 23
<212> TYPE: PRT
<213> ORGANISM: Artificial Sequence
<220> FEATURE:
<221> NAME/KEY: misc_feature
<222> LOCATION: (21)..(21)
<223> OTHER INFORMATION: Xaa on the 21st position means Met(O)

<400> SEQUENCE: 95

Trp Tyr Lys His Val Ala Ser Pro Arg Tyr His Thr Val Gly Arg Ala
1               5                   10                  15

```
Ala Gly Leu Leu Xaa Gly Leu
            20

<210> SEQ ID NO 96
<211> LENGTH: 22
<212> TYPE: PRT
<213> ORGANISM: Human

<400> SEQUENCE: 96

Trp Tyr Lys His Val Ala Ser Pro Arg Tyr His Thr Val Gly Arg Ala
1               5                   10                  15

Ala Gly Leu Leu Met Gly
            20

<210> SEQ ID NO 97
<211> LENGTH: 21
<212> TYPE: PRT
<213> ORGANISM: Human

<400> SEQUENCE: 97

Trp Tyr Lys His Val Ala Ser Pro Arg Tyr His Thr Val Gly Arg Ala
1               5                   10                  15

Ala Gly Leu Leu Met
            20

<210> SEQ ID NO 98
<211> LENGTH: 20
<212> TYPE: PRT
<213> ORGANISM: Human

<400> SEQUENCE: 98

Trp Tyr Lys His Val Ala Ser Pro Arg Tyr His Thr Val Gly Arg Ala
1               5                   10                  15

Ala Gly Leu Leu
            20

<210> SEQ ID NO 99
<211> LENGTH: 19
<212> TYPE: PRT
<213> ORGANISM: Human

<400> SEQUENCE: 99

Trp Tyr Lys His Val Ala Ser Pro Arg Tyr His Thr Val Gly Arg Ala
1               5                   10                  15

Ala Gly Leu

<210> SEQ ID NO 100
<211> LENGTH: 18
<212> TYPE: PRT
<213> ORGANISM: Human

<400> SEQUENCE: 100

Trp Tyr Lys His Val Ala Ser Pro Arg Tyr His Thr Val Gly Arg Ala
1               5                   10                  15

Ala Gly
       18

<210> SEQ ID NO 101
<211> LENGTH: 17
<212> TYPE: PRT
<213> ORGANISM: Human
```

-continued

```
<400> SEQUENCE: 101

Trp Tyr Lys His Val Ala Ser Pro Arg Tyr His Thr Val Gly Arg Ala
1               5                   10                  15

Ala

<210> SEQ ID NO 102
<211> LENGTH: 16
<212> TYPE: PRT
<213> ORGANISM: Human

<400> SEQUENCE: 102

Trp Tyr Lys His Val Ala Ser Pro Arg Tyr His Thr Val Gly Arg Ala
1               5                   10                  15

<210> SEQ ID NO 103
<211> LENGTH: 23
<212> TYPE: PRT
<213> ORGANISM: Artificial Sequence
<220> FEATURE:
<221> NAME/KEY: misc_feature
<222> LOCATION: (21)..(21)
<223> OTHER INFORMATION: Xaa on the 21st position means Met(O)

<400> SEQUENCE: 103

Trp Tyr Lys His Thr Ala Ser Pro Arg Tyr His Thr Val Gly Arg Ala
1               5                   10                  15

Ala Gly Leu Leu Xaa Gly Leu
            20

<210> SEQ ID NO 104
<211> LENGTH: 23
<212> TYPE: PRT
<213> ORGANISM: Artificial Sequence
<220> FEATURE:
<221> NAME/KEY: misc_feature
<222> LOCATION: (21)..(21)
<223> OTHER INFORMATION: Xaa on the 21st position means Met(O)

<400> SEQUENCE: 104

Trp Tyr Lys His Val Ala Ser Pro Arg Tyr His Thr Val Gly Arg Ala
1               5                   10                  15

Ser Gly Leu Leu Xaa Gly Leu
            20

<210> SEQ ID NO 105
<211> LENGTH: 23
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: Xaa on the 1st position means Fmoc Trp

<400> SEQUENCE: 105

Xaa Tyr Lys His Val Ala Ser Pro Arg Tyr His Thr Val Gly Arg Ala
1               5                   10                  15

Ala Gly Leu Leu Met Gly Leu
            20

<210> SEQ ID NO 106
<211> LENGTH: 23
<212> TYPE: PRT
<213> ORGANISM: Artificial Sequence
<220> FEATURE:
<221> NAME/KEY: misc_feature
```

<222> LOCATION: (1)..(1)
<223> OTHER INFORMATION: Xaa on the 1st position means Ac Trp

<400> SEQUENCE: 106

Xaa Tyr Lys His Val Ala Ser Pro Arg Tyr His Thr Val Gly Arg Ala
1               5                   10                  15

Ala Gly Leu Leu Met Gly Leu
            20

<210> SEQ ID NO 107
<211> LENGTH: 22
<212> TYPE: PRT
<213> ORGANISM: Human

<400> SEQUENCE: 107

Tyr Lys His Val Ala Ser Pro Arg Tyr His Thr Val Gly Arg Ala Ala
1               5                   10                  15

Gly Leu Leu Met Gly Leu
            20

<210> SEQ ID NO 108
<211> LENGTH: 20
<212> TYPE: PRT
<213> ORGANISM: Human

<400> SEQUENCE: 108

His Val Ala Ser Pro Arg Tyr His Thr Val Gly Arg Ala Ala Gly Leu
1               5                   10                  15

Leu Met Gly Leu
            20

<210> SEQ ID NO 109
<211> LENGTH: 15
<212> TYPE: PRT
<213> ORGANISM: Human

<400> SEQUENCE: 109

Arg Tyr His Thr Val Gly Arg Ala Ala Gly Leu Leu Met Gly Leu
1               5                   10                  15

<210> SEQ ID NO 110
<211> LENGTH: 9
<212> TYPE: PRT
<213> ORGANISM: Human

<400> SEQUENCE: 110

Arg Ala Ala Gly Leu Leu Met Gly Leu
1               5

<210> SEQ ID NO 111
<211> LENGTH: 22
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: Xaa on the 1st position means Ac Tyr

<400> SEQUENCE: 111

Xaa Lys His Val Ala Ser Pro Arg Tyr His Thr Val Gly Arg Ala Ala
1               5                   10                  15

Gly Leu Leu Met Gly Leu
            20

<210> SEQ ID NO 112
<211> LENGTH: 23
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: Xaa on the 1st position means DTrp

<400> SEQUENCE: 112

Xaa Tyr Lys His Val Ala Ser Pro Arg Tyr His Thr Val Gly Arg Ala
 1               5                  10                  15

Ala Gly Leu Leu Met Gly Leu
            20

<210> SEQ ID NO 113
<211> LENGTH: 22
<212> TYPE: PRT
<213> ORGANISM: Human
    <213> Artificial Sequence
<220> FEATURE:
<221> NAME/KEY: misc_feature
<222> LOCATION: (1)..(1)
<223> OTHER INFORMATION: Xaa on the 1st position means 3-Indolepropanoyl
    Tyr

<400> SEQUENCE: 113

Xaa Lys His Val Ala Ser Pro Arg Tyr His Thr Val Gly Arg Ala Ala
 1               5                  10                  15

Gly Leu Leu Met Gly Leu
            20

<210> SEQ ID NO 114
<211> LENGTH: 66
<212> TYPE: DNA
<213> ORGANISM: Human

<400> SEQUENCE: 114
tggtacaagc acgtggcgag tccccgctac cacacggtgg gccgcgccgc tggcctgctc      60
atgggg                                                                66

<210> SEQ ID NO 115
<211> LENGTH: 63
<212> TYPE: DNA
<213> ORGANISM: Human

<400> SEQUENCE: 115
tggtacaagc acgtggcgag tccccgctac cacacggtgg gccgcgccgc tggcctgctc      60
atg                                                                   63

<210> SEQ ID NO 116
<211> LENGTH: 60
<212> TYPE: DNA
<213> ORGANISM: Human

<400> SEQUENCE: 116
tggtacaagc acgtggcgag tccccgctac cacacggtgg gccgcgccgc tggcctgctc      60

<210> SEQ ID NO 117
<211> LENGTH: 57
<212> TYPE: DNA
<213> ORGANISM: Human

<400> SEQUENCE: 117

```
tggtacaagc acgtggcgag tccccgctac cacacggtgg gccgcgccgc tggcctg      57

<210> SEQ ID NO 118
<211> LENGTH: 54
<212> TYPE: DNA
<213> ORGANISM: Human

<400> SEQUENCE: 118
tggtacaagc acgtggcgag tccccgctac cacacggtgg gccgcgccgc tggc         54

<210> SEQ ID NO 119
<211> LENGTH: 51
<212> TYPE: DNA
<213> ORGANISM: Human

<400> SEQUENCE: 119
tggtacaagc acgtggcgag tccccgctac cacacggtgg gccgcgccgc t            51

<210> SEQ ID NO 120
<211> LENGTH: 48
<212> TYPE: DNA
<213> ORGANISM: Human

<400> SEQUENCE: 120
tggtacaagc acgtggcgag tccccgctac cacacggtgg gccgcgcc               48

<210> SEQ ID NO 121
<211> LENGTH: 66
<212> TYPE: DNA
<213> ORGANISM: Human

<400> SEQUENCE: 121
tacaagcacg tggcgagtcc ccgctaccac acggtgggcc gcgccgctgg cctgctcatg   60
gggctg                                                             66

<210> SEQ ID NO 122
<211> LENGTH: 60
<212> TYPE: DNA
<213> ORGANISM: Human

<400> SEQUENCE: 122
cacgtggcga gtccccgcta ccacacggtg ggccgcgccg ctggcctgct catggggctg   60

<210> SEQ ID NO 123
<211> LENGTH: 45
<212> TYPE: DNA
<213> ORGANISM: Human

<400> SEQUENCE: 123
cgctaccaca cggtgggccg cgccgctggc ctgctcatgg ggctg                   45

<210> SEQ ID NO 124
<211> LENGTH: 27
<212> TYPE: DNA
<213> ORGANISM: Human

<400> SEQUENCE: 124
cgcgccgctg gcctgctcat ggggctg                                       27

<210> SEQ ID NO 125
<211> LENGTH: 51
<212> TYPE: DNA
```

-continued

```
<213> ORGANISM: Porcine

<400> SEQUENCE: 125
tggtacaagc acacggcgag tccccgctac cacacggtgg gccgcgccgc g         51
```